(12) United States Patent
Ehrenfels et al.

(10) Patent No.: US 8,074,861 B2
(45) Date of Patent: Dec. 13, 2011

(54) SURGICAL FASTENER APPLYING APPARATUS

(75) Inventors: Karl H. Ehrenfels, Cheshire, CT (US);
David Ivanko, San Diego, CA (US);
Randolph F. Lehn, Stratford, CT (US);
Roberto Pedros, Oxford, CT (US);
Csaba L. Rethy, Fairfield, CT (US);
Frank Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 86 days.

(21) Appl. No.: 12/619,829

(22) Filed: Nov. 17, 2009

(65) Prior Publication Data

US 2010/0193570 A1  Aug. 5, 2010

Related U.S. Application Data

(60) Continuation of application No. 12/115,612, filed on May 6, 2008, now Pat. No. 7,631,794, which is a continuation of application No. 11/699,686, filed on Jan. 29, 2007, now Pat. No. 7,631,793, which is a continuation of application No. 10/508,191, filed as application No. PCT/US03/08342 on Mar. 19, 2003, now Pat. No. 7,334,717, said application No. 10/508,191 is a continuation-in-part of application No. 10/490,517, filed as application No. PCT/US02/31963 on Oct. 4, 2002, application No. 12/619,829, which is a continuation-in-part of application No. 12/186,269, filed on Aug. 5, 2008, now Pat. No. 7,721,933, which is a continuation of application No. 12/011,419, filed on Jan. 24, 2008, now Pat. No. 7,568,604, which is a continuation of application No. 11/699,620, filed on Jan. 29, 2007, now Pat. No. 7,419,081, which is a continuation of application No. 11/356,912, filed on Feb. 16, 2006, now Pat. No. 7,293,685, which is a division of application No. 11/292,736, filed on Dec. 2, 2005, now Pat. No. 7,140,527, which is a division of application No. 10/399,071, filed as application No. PCT/US01/32213 on Oct. 15, 2001, now Pat. No. 7,055,730.

(60) Provisional application No. 60/365,761, filed on Mar. 19, 2002, provisional application No. 60/416,371, filed on Oct. 4, 2002, provisional application No. 60/327,369, filed on Oct. 5, 2001, provisional application No. 60/240,461, filed on Oct. 13, 2000.

(51) Int. Cl.
*A61B 17/10* (2006.01)

(52) U.S. Cl. ............... 227/180.1; 227/175.1; 227/176.1; 227/19; 227/175.2

(58) Field of Classification Search ............... 227/175.1, 227/175.2, 180.1, 19, 182.1
See application file for complete search history.

(56) References Cited

U.S. PATENT DOCUMENTS 960,300 A    6/1910   Fischer
(Continued)

FOREIGN PATENT DOCUMENTS

EP    0514185    11/1992
(Continued)

OTHER PUBLICATIONS

International Search Report dated Dec. 12, 2001.
(Continued)

*Primary Examiner* — Brian D Nash

(57) ABSTRACT

The present disclosure relates to surgical fastener applying apparatus for sequentially applying a plurality of surgical fasteners to body tissue. The surgical fastener applying apparatus includes a replaceable cartridge assembly receivable in a distal end portion of a cartridge receiving half-section, the cartridge assembly including a safety lockout pivotably disposed along the upper surface of the cartridge assembly and movable from an unlocked orientation permitting assembly of an anvil half-section to the cartridge receiving half-section, to a locked orientation preventing assembly of the anvil half-section to the cartridge receiving-half section.

9 Claims, 60 Drawing Sheets

U.S. PATENT DOCUMENTS

| | | |
|---|---|---|
| 2,301,622 A | 11/1942 | Hambrecht |
| 2,853,074 A | 9/1958 | Olson |
| 2,874,384 A | 2/1959 | Krone |
| 2,891,250 A | 6/1959 | Hirata |
| 3,079,606 A | 3/1963 | Bobrov et al. |
| 3,080,564 A | 3/1963 | Strekopov et al. |
| 3,252,643 A | 5/1966 | Strekopov et al. |
| 3,269,630 A | 8/1966 | Fleischer |
| 3,275,211 A | 9/1966 | Hirsch et al. |
| 3,278,107 A | 10/1966 | Rygg |
| 3,315,863 A | 4/1967 | O'Dea |
| 3,490,675 A | 1/1970 | Green et al. |
| 3,499,591 A | 3/1970 | Green |
| 3,589,589 A | 6/1971 | Akopov et al. |
| 3,598,299 A | 8/1971 | Johnson |
| 3,692,224 A | 9/1972 | Astafiev et al. |
| 3,795,034 A | 3/1974 | Strekopytov et al. |
| 3,889,683 A | 6/1975 | Kapitanov et al. |
| 3,935,981 A | 2/1976 | Akopov et al. |
| 3,949,923 A | 4/1976 | Akopov et al. |
| 3,973,709 A | 8/1976 | Akopov et al. |
| 4,047,654 A | 9/1977 | Alvarado |
| 4,111,206 A | 9/1978 | Vishnevsky et al. |
| 4,162,678 A | 7/1979 | Fedotov et al. |
| 4,216,890 A | 8/1980 | Akopov et al. |
| 4,216,891 A | 8/1980 | Vehlke |
| 4,272,002 A | 6/1981 | Moshofsky |
| 4,290,542 A | 9/1981 | Fedotov et al. |
| 4,296,881 A | 10/1981 | Lee |
| 4,316,468 A | 2/1982 | Llieman et al. |
| 4,317,105 A | 2/1982 | Sinha et al. |
| 4,325,376 A | 4/1982 | Klieman et al. |
| 4,378,901 A | 4/1983 | Akopov et al. |
| 4,397,311 A | 8/1983 | Kanshin et al. |
| 4,429,695 A * | 2/1984 | Green ........................ 227/176.1 |
| 4,442,964 A | 4/1984 | Becht |
| 4,453,661 A | 6/1984 | Genyk et al. |
| 4,470,533 A | 9/1984 | Schuler |
| 4,477,007 A | 10/1984 | Foslien |
| 4,485,811 A | 12/1984 | Chernousov et al. |
| 4,520,817 A * | 6/1985 | Green ........................ 227/176.1 |
| 4,527,724 A | 7/1985 | Chow et al. |
| 4,550,870 A | 11/1985 | Krumme et al. |
| 4,568,009 A * | 2/1986 | Green ........................... 227/19 |
| 4,570,633 A | 2/1986 | Golden |
| 4,585,153 A | 4/1986 | Failla et al. |
| 4,596,351 A | 6/1986 | Fedotov et al. |
| 4,605,001 A | 8/1986 | Rothfuss et al. |
| 4,607,636 A | 8/1986 | Kula et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,648,542 A | 3/1987 | Fox et al. |
| 4,684,051 A | 8/1987 | Akopov et al. |
| 4,741,336 A | 5/1988 | Failla et al. |
| 4,784,137 A | 11/1988 | Kulik et al. |
| 4,805,823 A | 2/1989 | Rothfuss |
| 4,848,637 A | 7/1989 | Pruitt |
| 4,863,088 A | 9/1989 | Redmond et al. |
| 4,892,244 A | 1/1990 | Fox et al. |
| 4,930,503 A | 6/1990 | Pruitt |
| 4,991,764 A | 2/1991 | Mericle |
| 5,005,754 A | 4/1991 | Van Overloop |
| 5,018,657 A | 5/1991 | Pedlick et al. |
| 5,065,929 A | 11/1991 | Schulze et al. |
| 5,071,052 A * | 12/1991 | Rodak et al. ................ 227/175.2 |
| 5,074,454 A | 12/1991 | Peters |
| 5,083,695 A | 1/1992 | Foslien et al. |
| 5,111,987 A | 5/1992 | Moeizadeh et al. |
| 5,129,570 A | 7/1992 | Schulze et al. |
| 5,137,198 A | 8/1992 | Nobis et al. |
| 5,141,144 A | 8/1992 | Foslien et al. |
| 5,170,925 A | 12/1992 | Madden et al. |
| 5,172,845 A | 12/1992 | Tejeiro |
| 5,180,092 A | 1/1993 | Crainich |
| 5,188,274 A | 2/1993 | Moeinzadeh et al. |
| 5,205,459 A | 4/1993 | Brinkerhoff et al. |
| 5,240,163 A | 8/1993 | Stein et al. |
| 5,263,629 A | 11/1993 | Trumbull et al. |
| RE34,519 E | 1/1994 | Fox et al. |
| 5,275,322 A | 1/1994 | Brinkerhoff et al. |
| 5,292,053 A | 3/1994 | Bilotti et al. |
| 5,307,976 A | 5/1994 | Olson et al. |
| 5,312,024 A | 5/1994 | Grant et al. |
| 5,332,142 A | 7/1994 | Robinson et al. |
| 5,344,061 A | 9/1994 | Crainich |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,324 A | 3/1995 | Carroll et al. |
| 5,405,073 A | 4/1995 | Porter |
| 5,415,334 A | 5/1995 | Williamson, IV et al. |
| 5,415,335 A | 5/1995 | Knodell, Jr. |
| 5,417,361 A | 5/1995 | Williamson, IV |
| 5,431,232 A | 7/1995 | Kirsch |
| 5,433,721 A | 7/1995 | Hooven et al. |
| 5,439,156 A | 8/1995 | Grant et al. |
| 5,445,304 A | 8/1995 | Plyley et al. |
| 5,447,265 A | 9/1995 | Vidal et al. |
| 5,452,836 A | 9/1995 | Huiteman et al. |
| 5,452,837 A | 9/1995 | Williamson, IV et al. |
| 5,458,279 A | 10/1995 | Plyley |
| 5,464,144 A | 11/1995 | Guy et al. |
| 5,465,894 A | 11/1995 | Clark et al. |
| 5,465,895 A | 11/1995 | Knodel et al. |
| 5,470,007 A | 11/1995 | Plyley et al. |
| 5,470,010 A | 11/1995 | Rothfuss et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,497,934 A | 3/1996 | Brady et al. |
| 5,503,320 A | 4/1996 | Webster et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,937 A | 7/1996 | Boiarski et al. |
| 5,547,117 A | 8/1996 | Hamblin et al. |
| 5,549,628 A | 8/1996 | Cooper et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,564,615 A | 10/1996 | Bishop et al. |
| 5,575,803 A | 11/1996 | Cooper et al. |
| 5,580,067 A | 12/1996 | Hamblin et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,630,541 A | 5/1997 | Williamson, IV et al. |
| 5,632,432 A | 5/1997 | Schulze et al. |
| 5,632,433 A | 5/1997 | Grant et al. |
| 5,634,584 A | 6/1997 | Okorocha et al. |
| 5,641,111 A | 6/1997 | Ahrenis et al. |
| 5,655,698 A | 8/1997 | Yoon |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,665,085 A | 9/1997 | Nardella et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |

| | | | | | | |
|---|---|---|---|---|---|---|
| 5,676,674 A | 10/1997 | Bolanos et al. | | 5,988,479 A | 11/1999 | Palmer |
| 5,678,748 A | 10/1997 | Plyley et al. | | 6,010,054 A | 1/2000 | Johnson et al. |
| 5,680,982 A | 10/1997 | Schulze et al. | | 6,045,560 A | 4/2000 | McKean et al. |
| 5,692,668 A | 12/1997 | Schulze et al. | | 6,099,551 A | 8/2000 | Gavvay |
| 5,697,542 A | 12/1997 | Knodel et al. | | 6,131,789 A | 10/2000 | Schulze et al. |
| 5,697,543 A | 12/1997 | Burdorff | | 6,131,790 A | 10/2000 | Piraka |
| 5,702,409 A | 12/1997 | Rayburn et al. | | 6,264,087 B1 | 7/2001 | Whitman |
| 5,704,534 A | 1/1998 | Huitema et al. | | 6,315,183 B1 | 11/2001 | Piraka |
| 5,716,366 A | 2/1998 | Yates | | 6,325,810 B1 | 12/2001 | Hamilton et al. |
| 5,725,554 A | 3/1998 | Simon et al. | | 7,032,799 B2 | 4/2006 | Viola et al. |
| 5,732,871 A | 3/1998 | Clark et al. | | 7,055,730 B2 * | 6/2006 | Ehrenfels et al. .......... 227/175.4 |
| 5,735,848 A | 4/1998 | Yates et al. | | 7,334,717 B2 * | 2/2008 | Rethy et al. ................ 227/175.1 |
| 5,752,965 A | 5/1998 | Francis et al. | | 2005/0082336 A1 | 4/2005 | Ivanko |
| 5,762,255 A | 6/1998 | Chrisman et al. | | 2006/0273135 A1 | 12/2006 | Beetel |
| 5,769,303 A | 6/1998 | Knodel et al. | | | | |
| 5,769,892 A | 6/1998 | Kingwell | | | | |
| 5,779,131 A | 7/1998 | Knodel et al. | | | | |
| 5,779,132 A | 7/1998 | Knodel et al. | | | | |
| 5,785,232 A | 7/1998 | Vidal et al. | | | | |
| 5,794,834 A | 8/1998 | Hamblin et al. | | | | |
| 5,797,537 A | 8/1998 | Oberlin et al. | | | | |
| 5,810,240 A | 9/1998 | Robertson | | | | |
| 5,810,811 A | 9/1998 | Yates et al. | | | | |
| 5,810,855 A | 9/1998 | Rayburn et al. | | | | |
| 5,820,009 A | 10/1998 | Melling et al. | | | | |
| 5,826,776 A | 10/1998 | Schulze et al. | | | | |
| 5,855,311 A | 1/1999 | Hamblin et al. | | | | |
| 5,871,135 A | 2/1999 | Williamson, IV et al. | | | | |
| 5,878,938 A | 3/1999 | Bittner et al. | | | | |
| 5,919,198 A | 7/1999 | Graves, Jr. et al. | | | | |

FOREIGN PATENT DOCUMENTS

| | | |
|---|---|---|
| EP | 0625335 | 11/1994 |
| EP | 0639349 | 2/1995 |
| WO | WO 02/30297 | 4/2002 |

OTHER PUBLICATIONS

U.S. Patent Application for "Surgical Stapling Apparatus and Method" filed Mar. 23, 2004.

U.S. Patent Application for "Directionally Biased Staple and Method of Manufacturing" filed Oct. 20, 2000.

U.S. Patent Application for Directionally Biased Staple and Anvil Assembly for Forming the Staple filed Mar. 28, 2003.

* cited by examiner

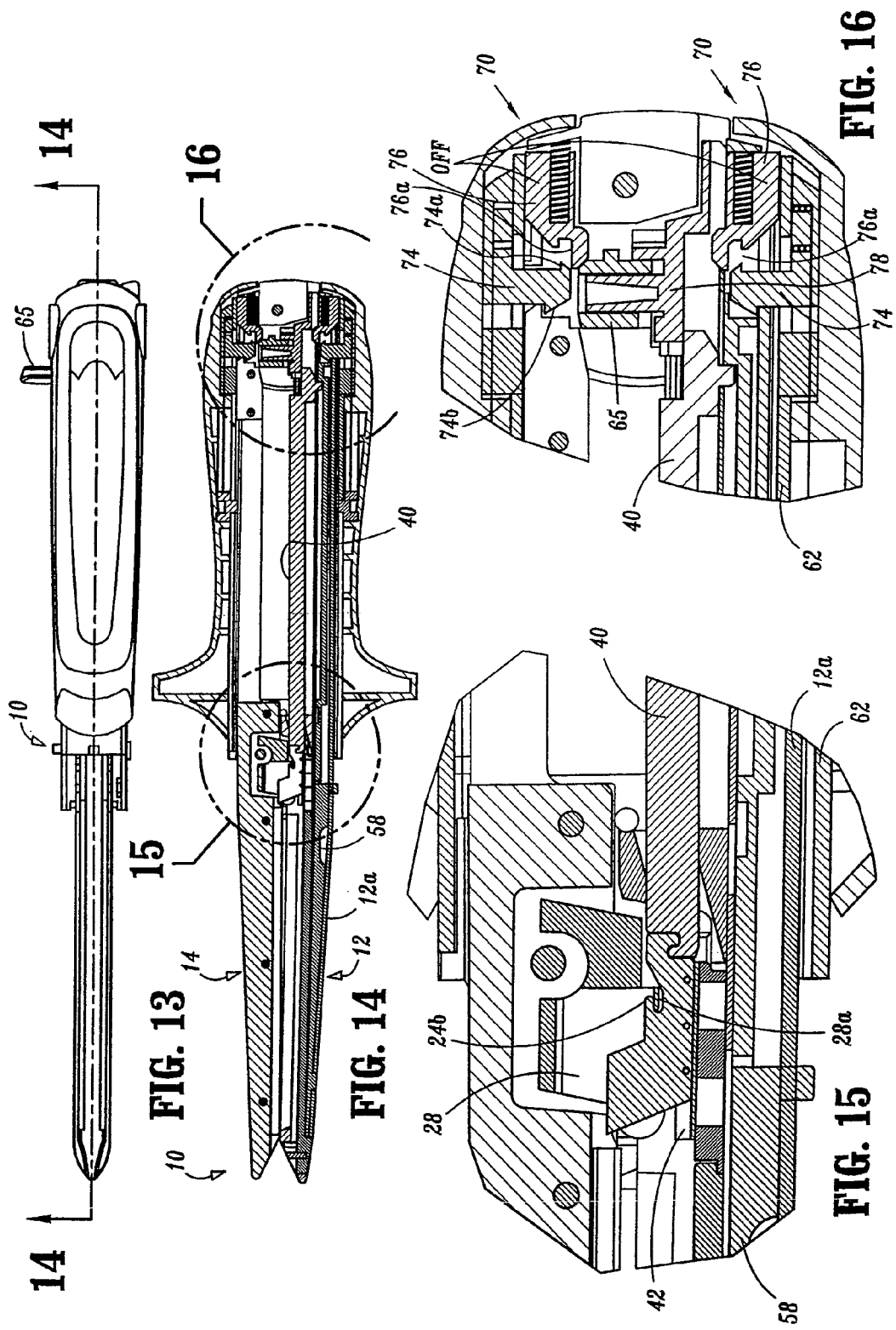

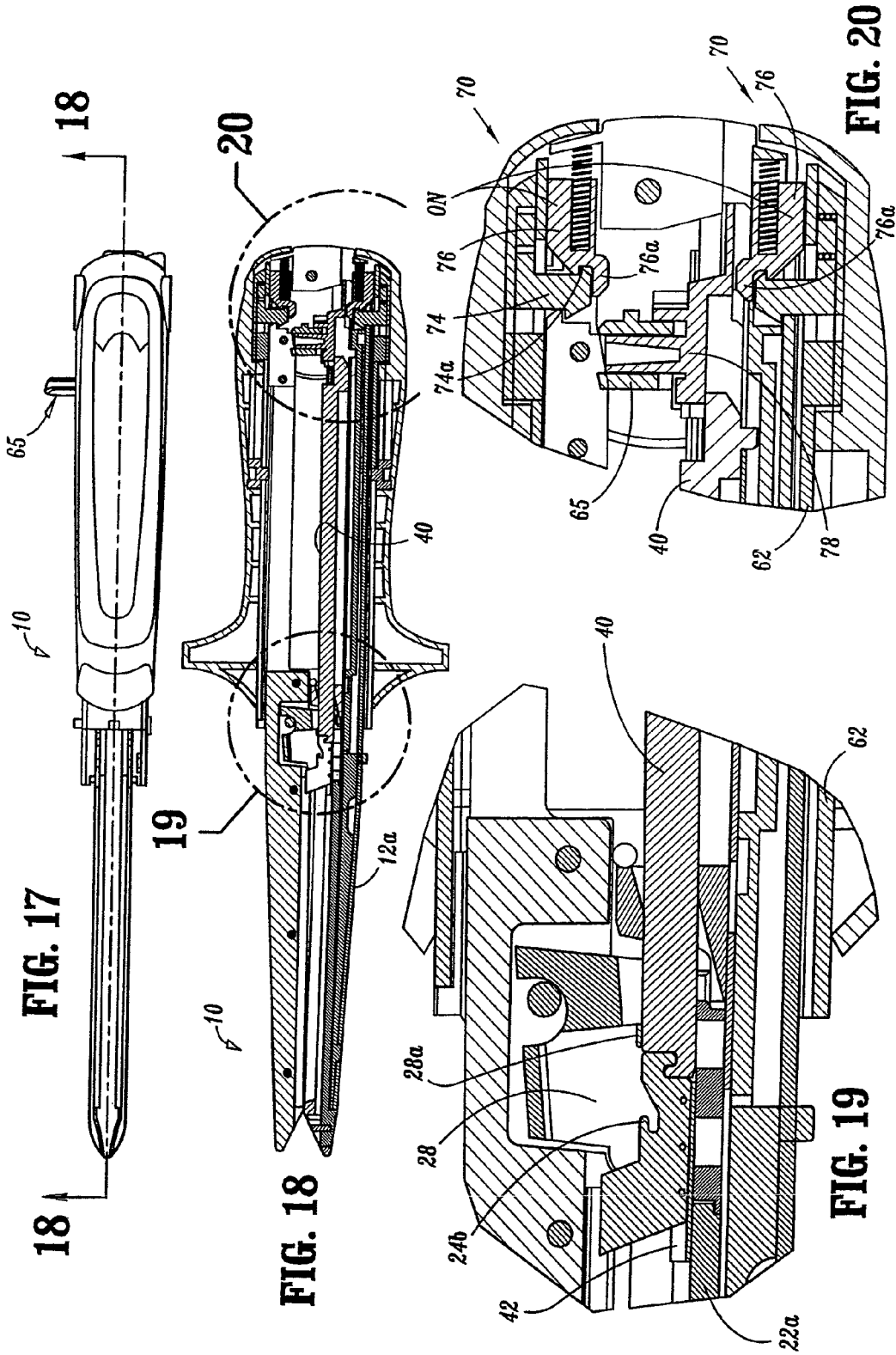

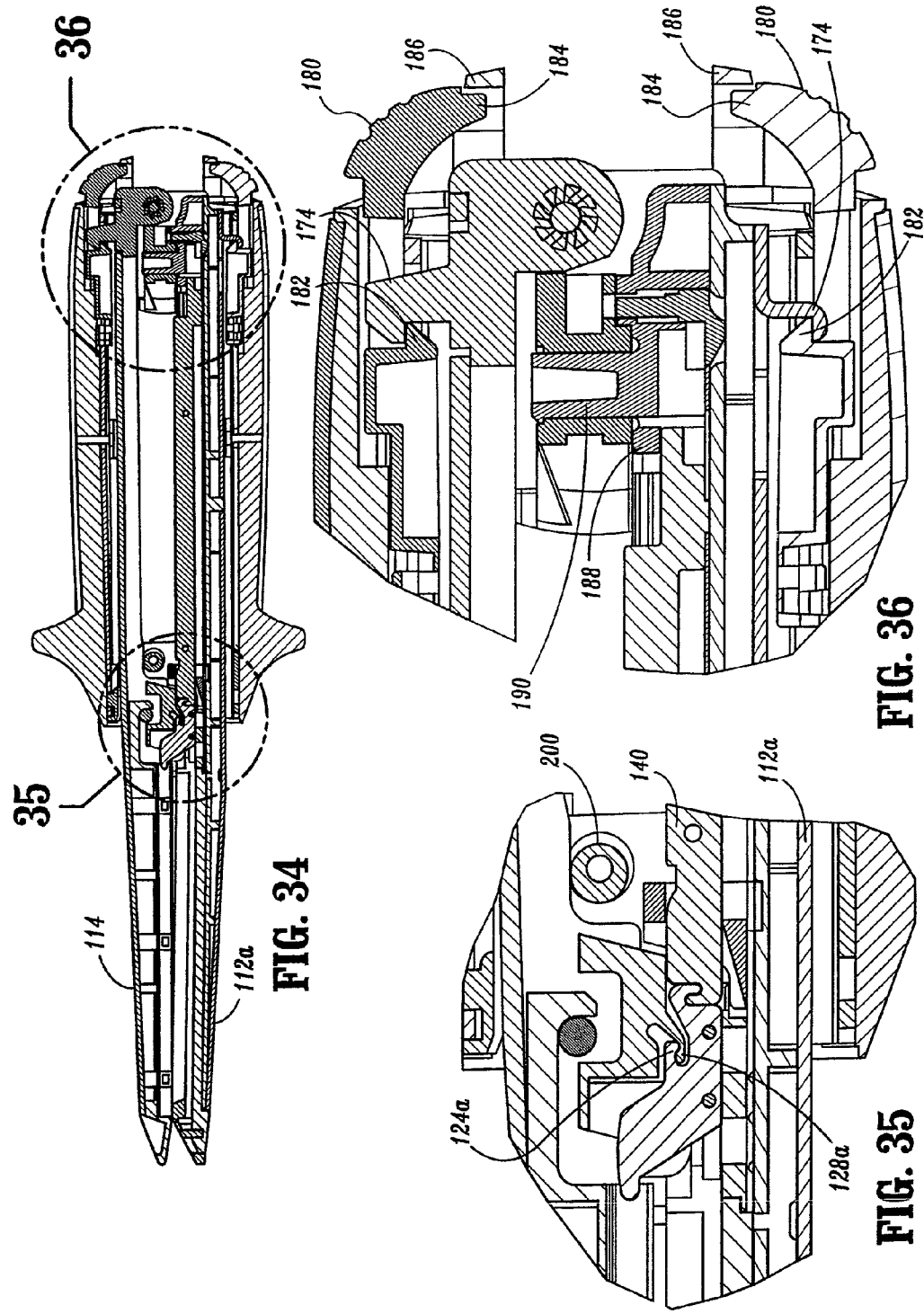

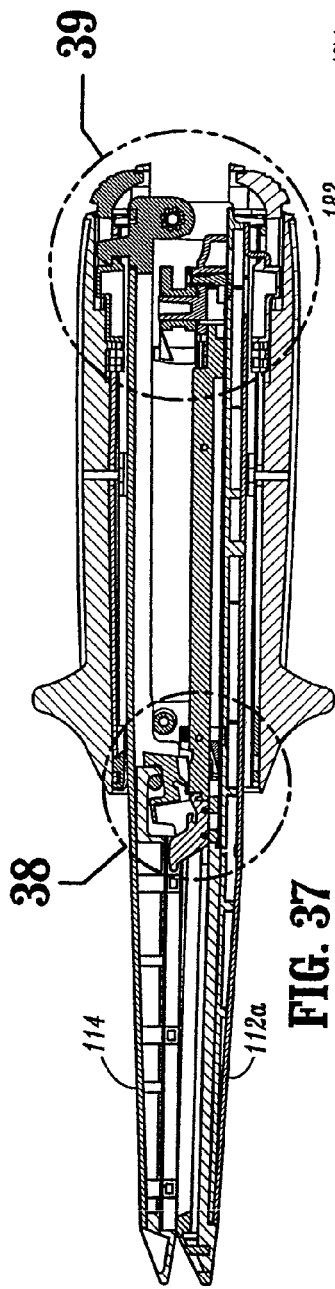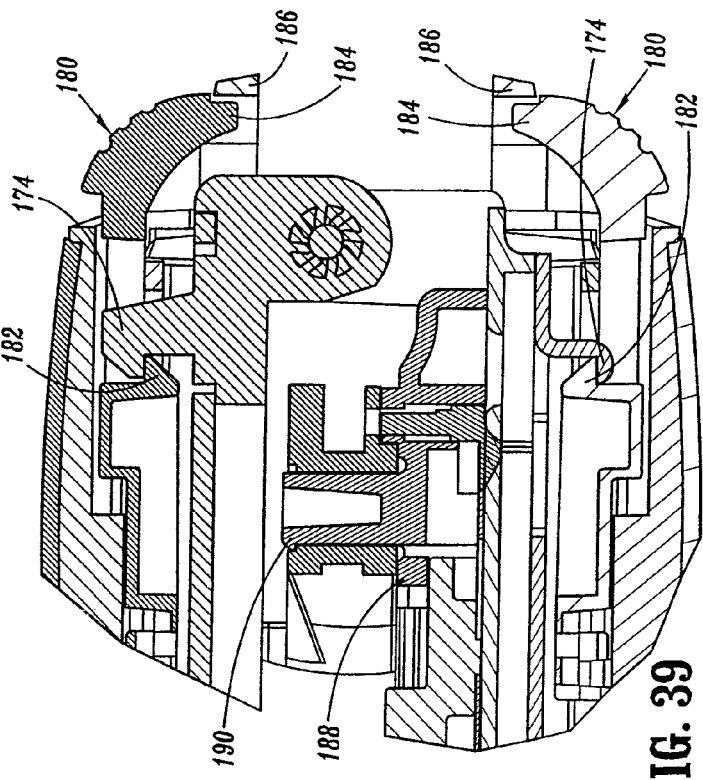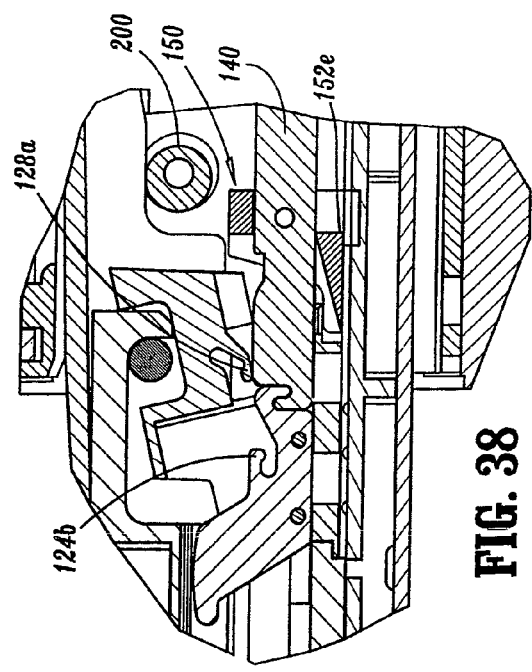

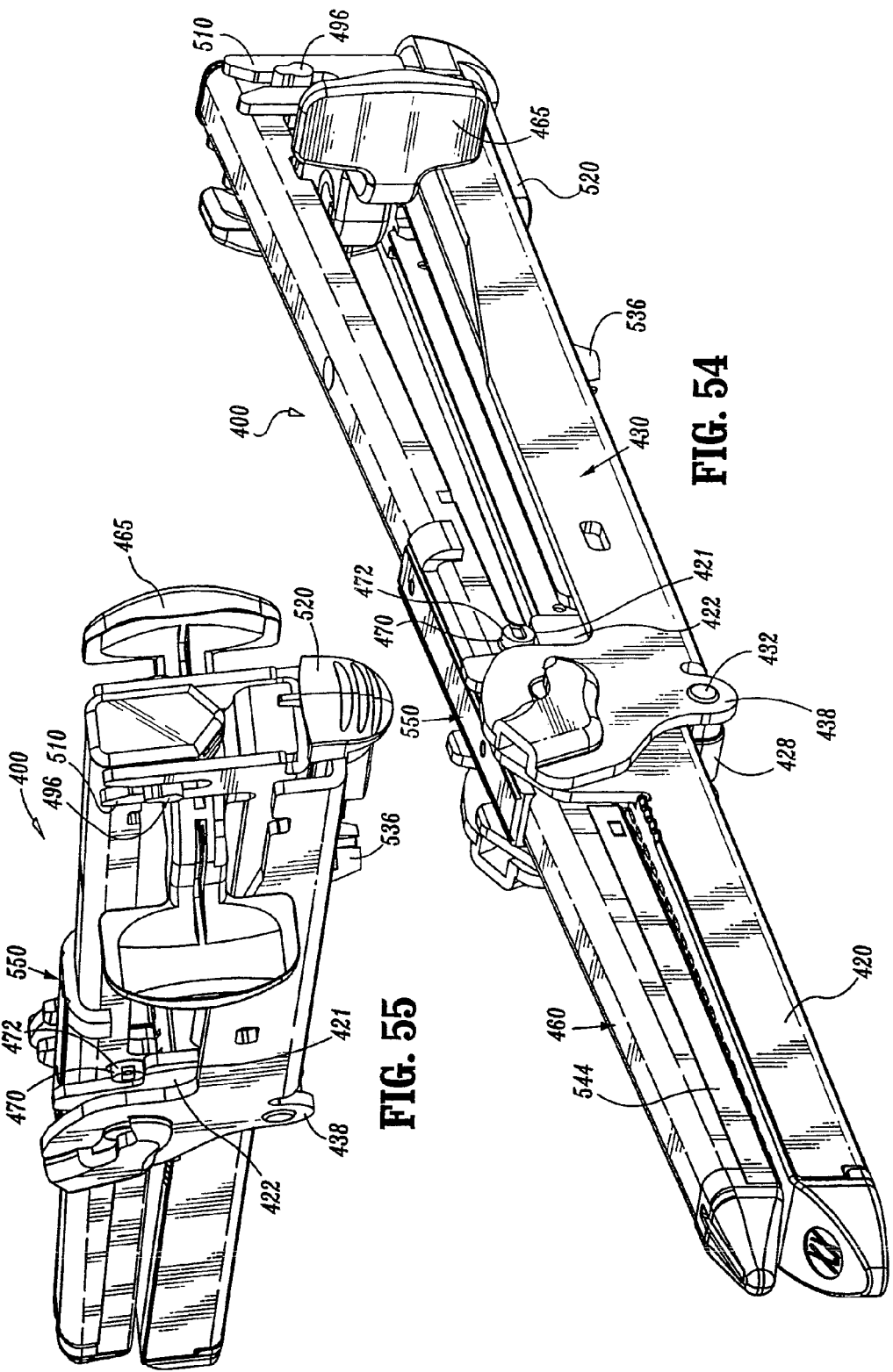

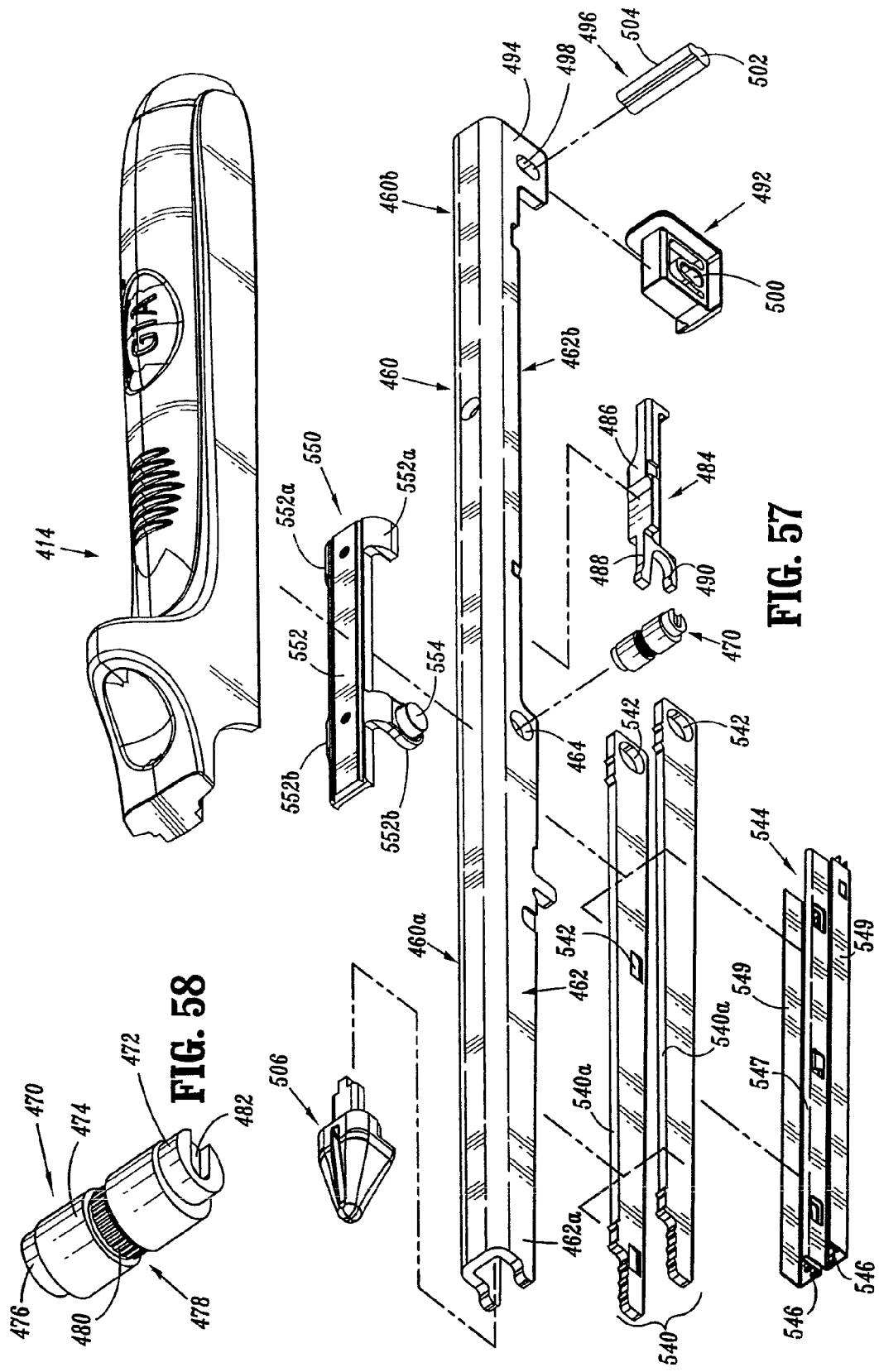

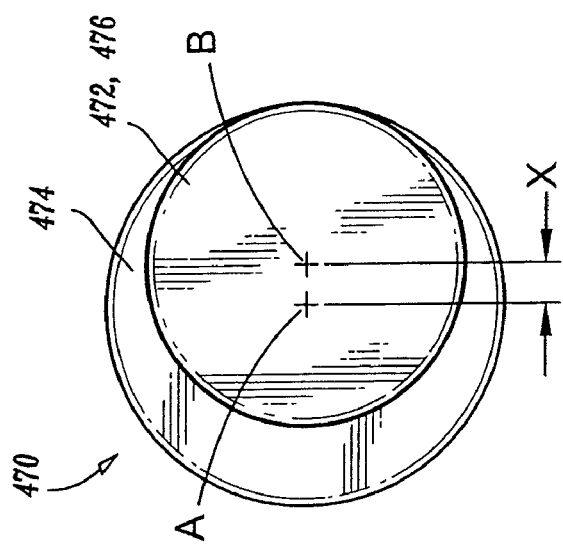
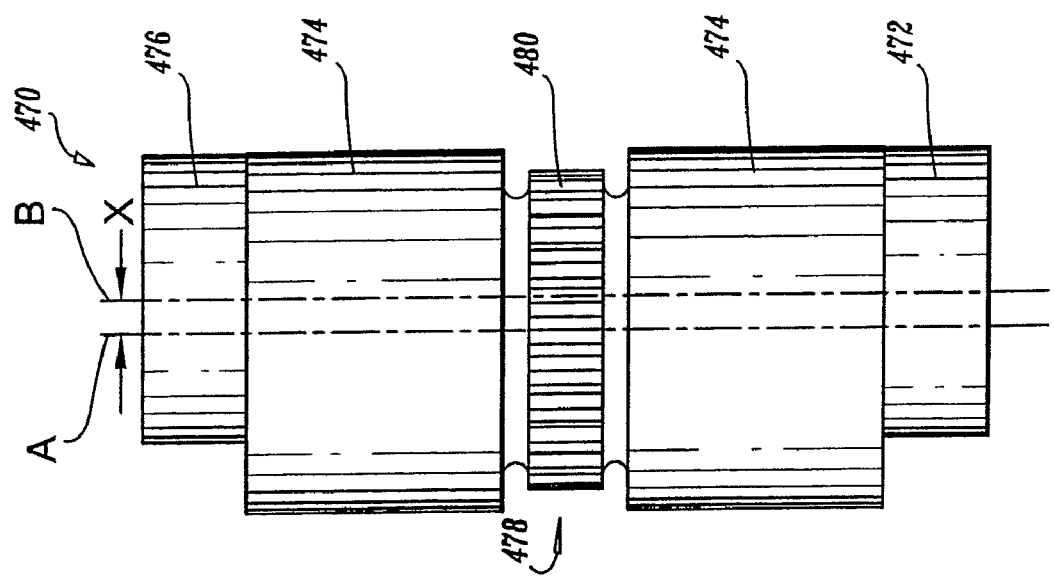
FIG. 58b
FIG. 58a

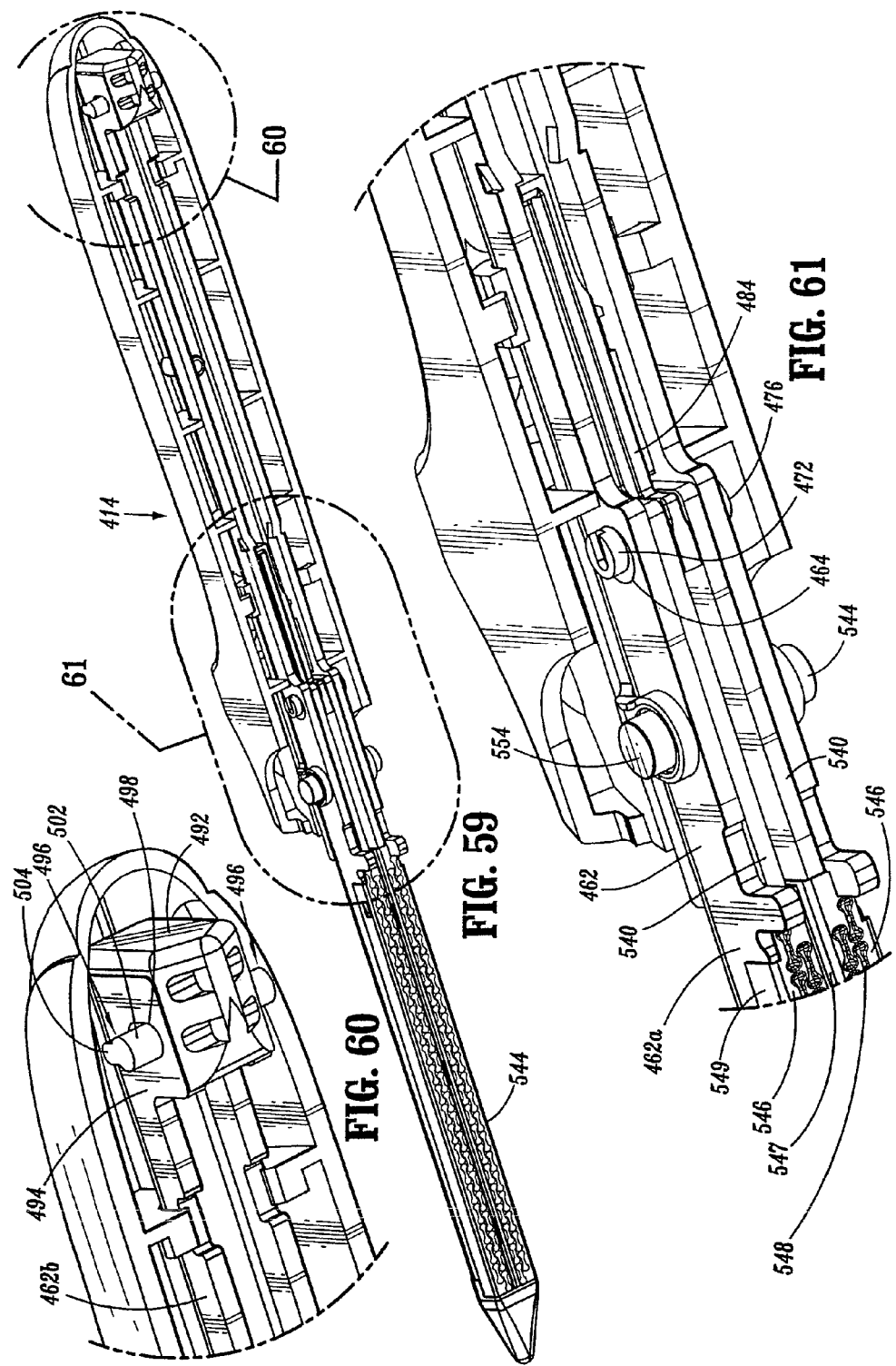

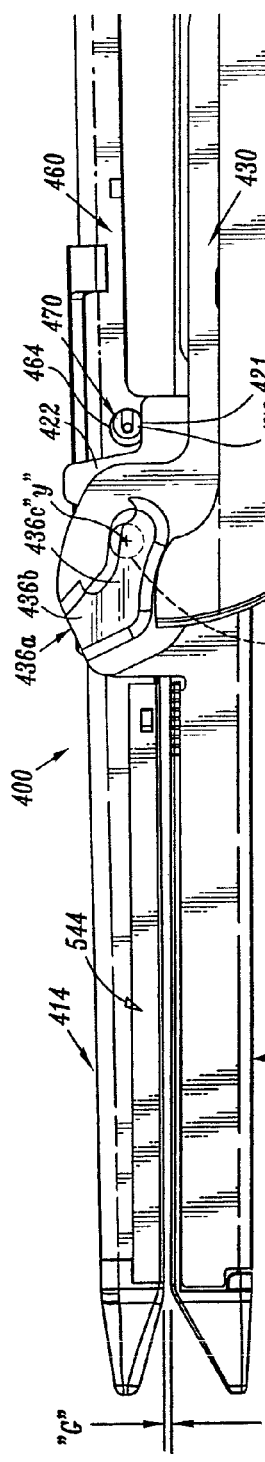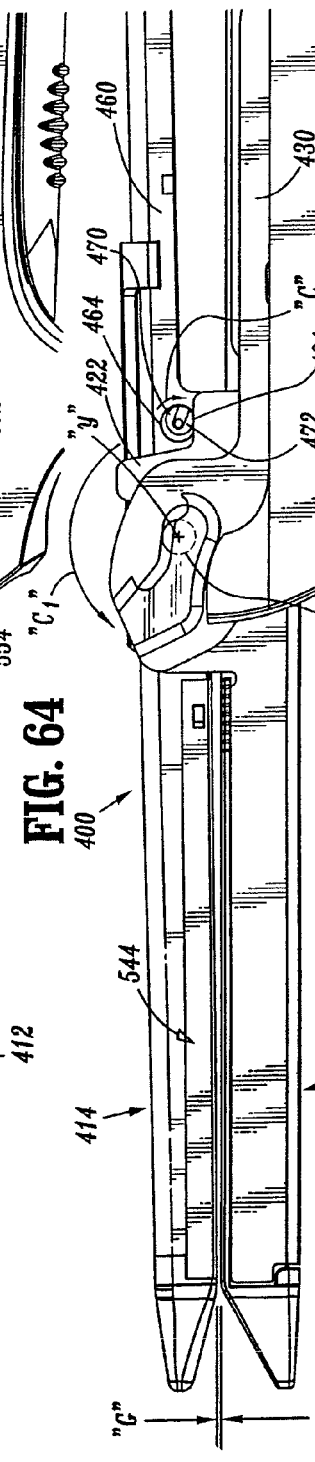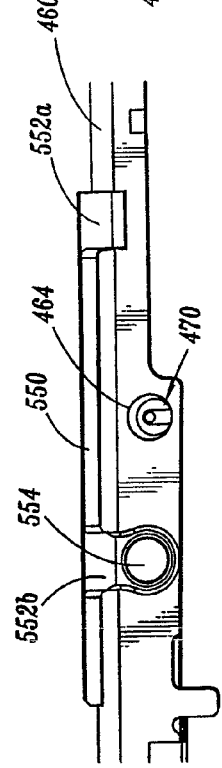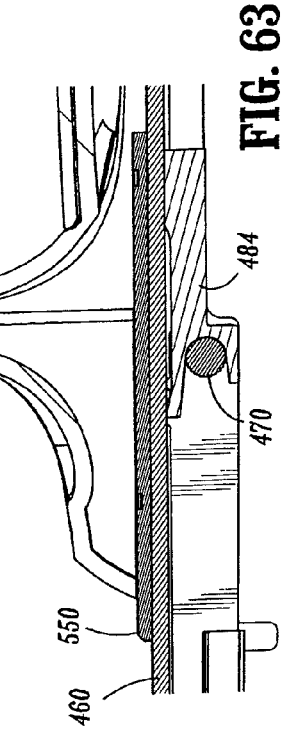

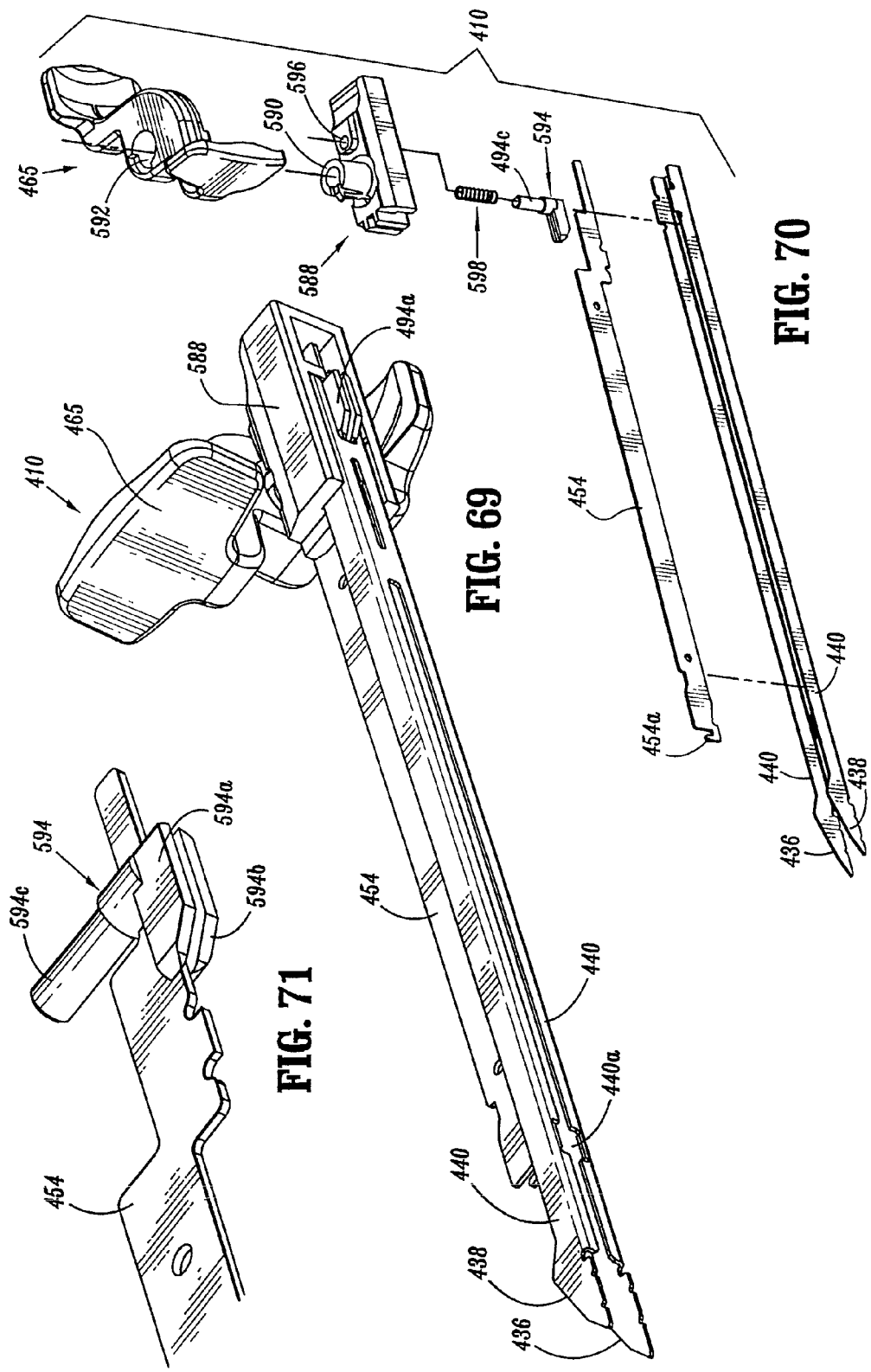

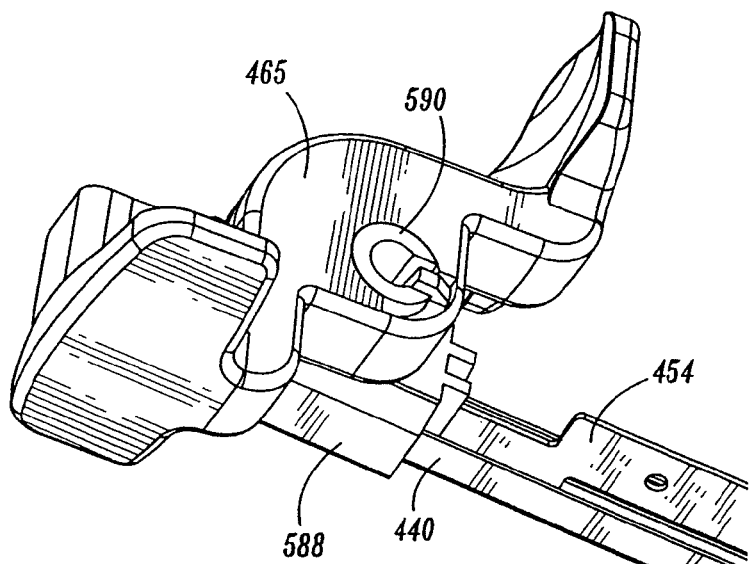
FIG. 72
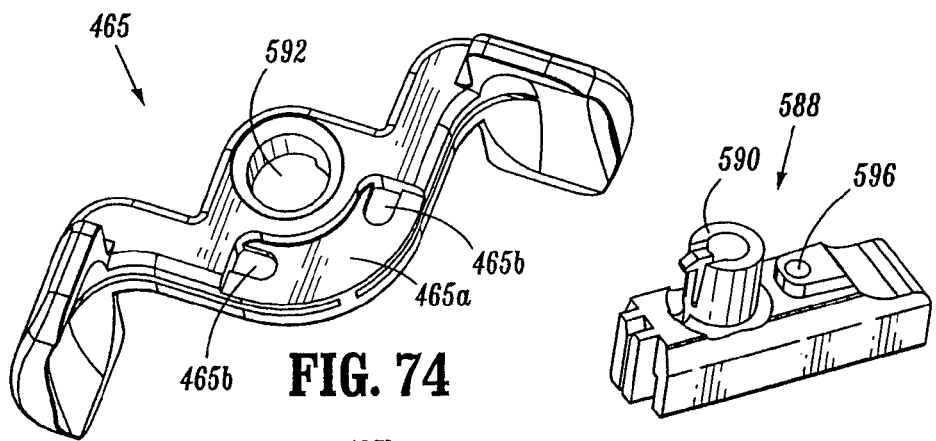
FIG. 74
FIG. 73
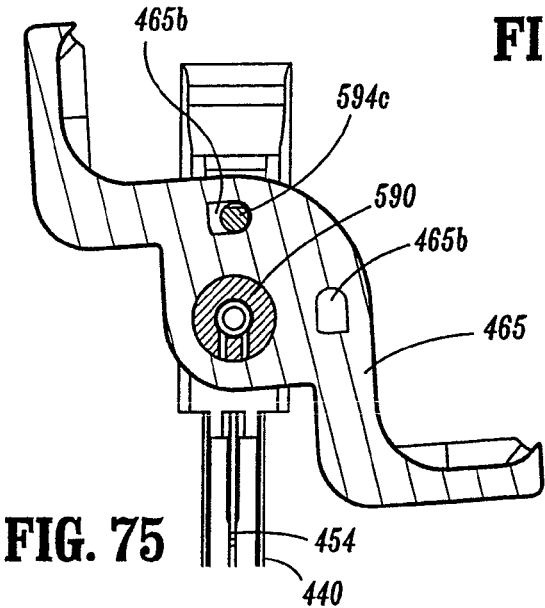
FIG. 75

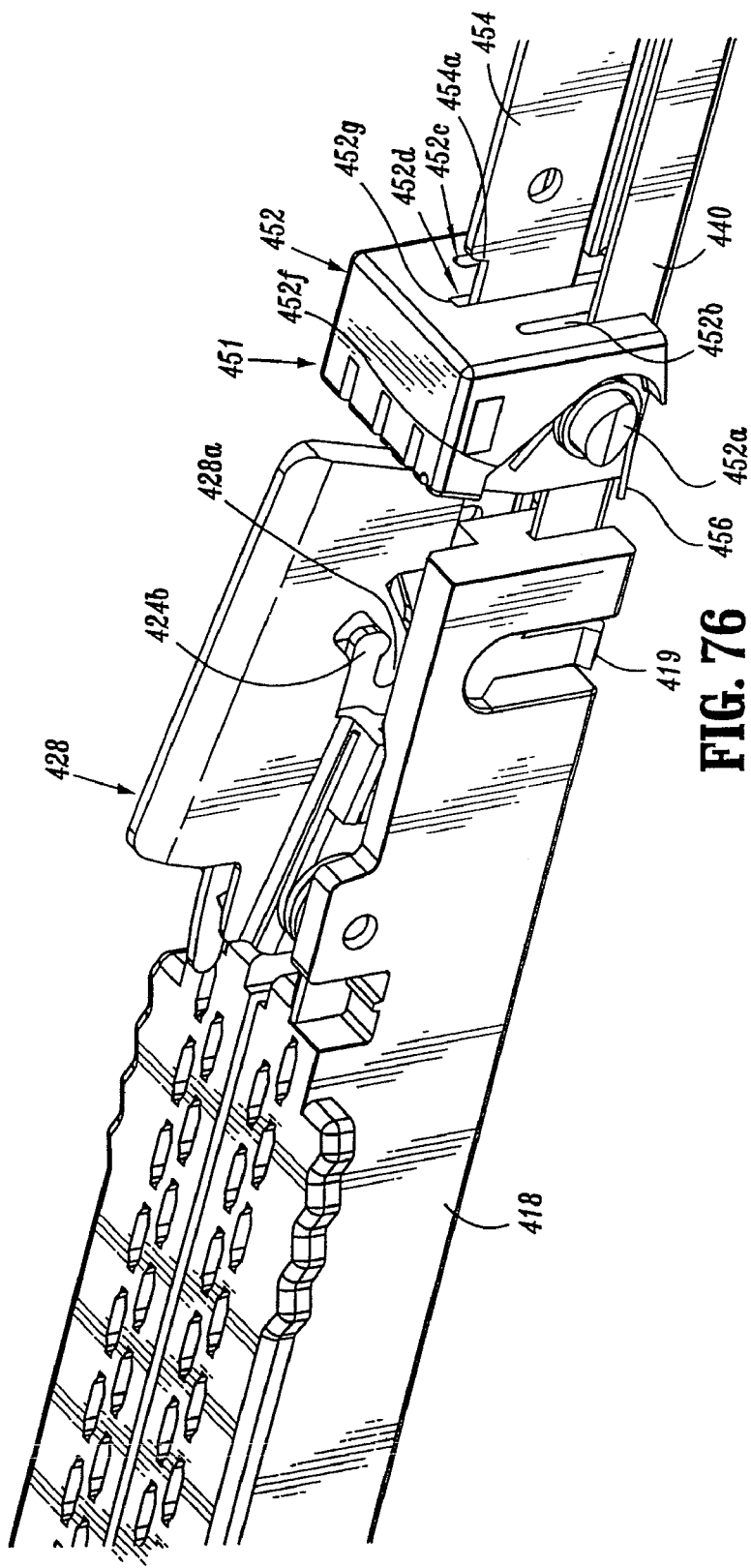

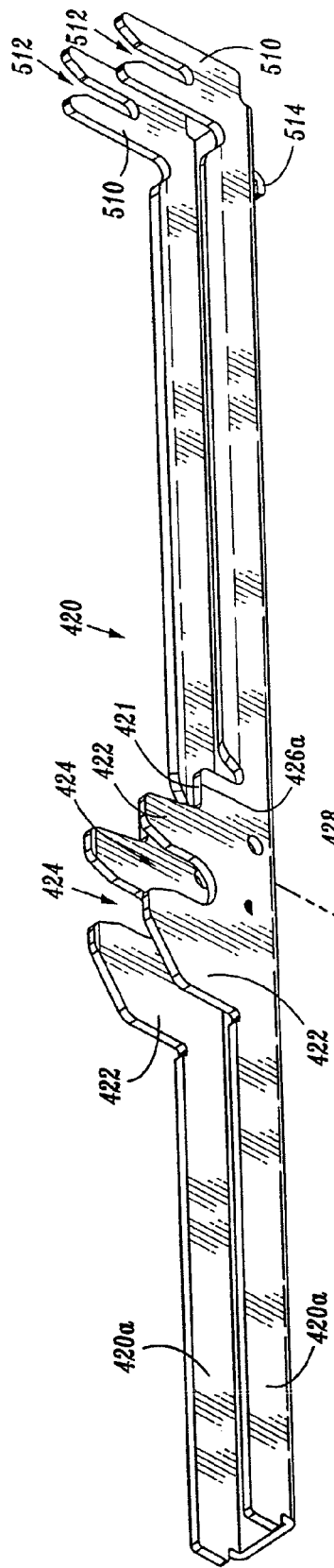
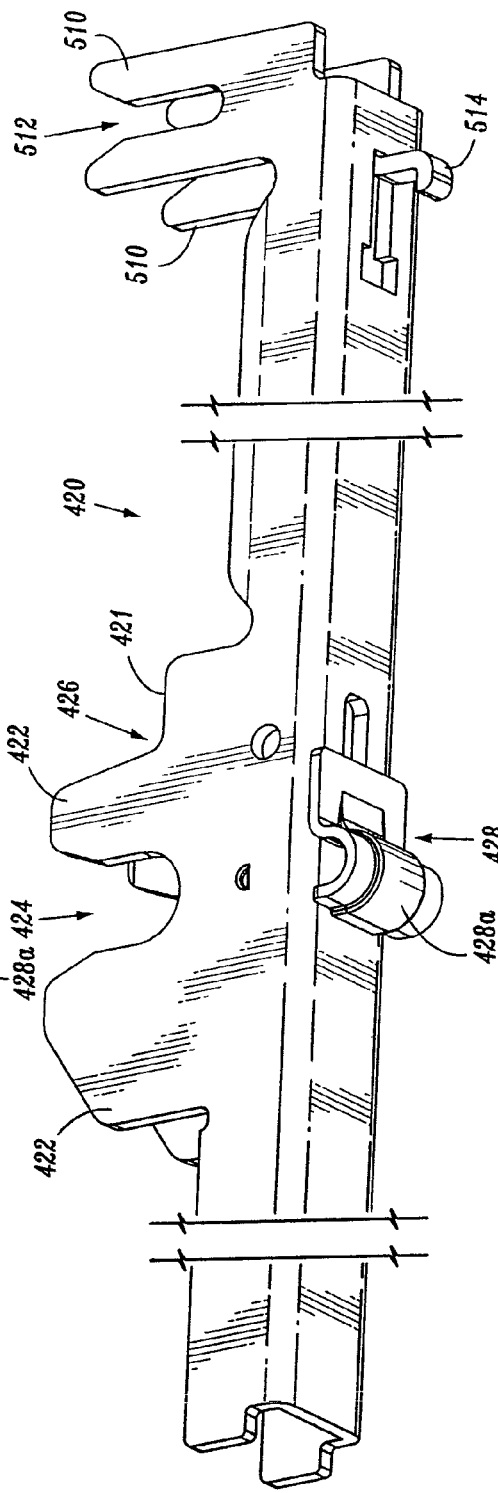

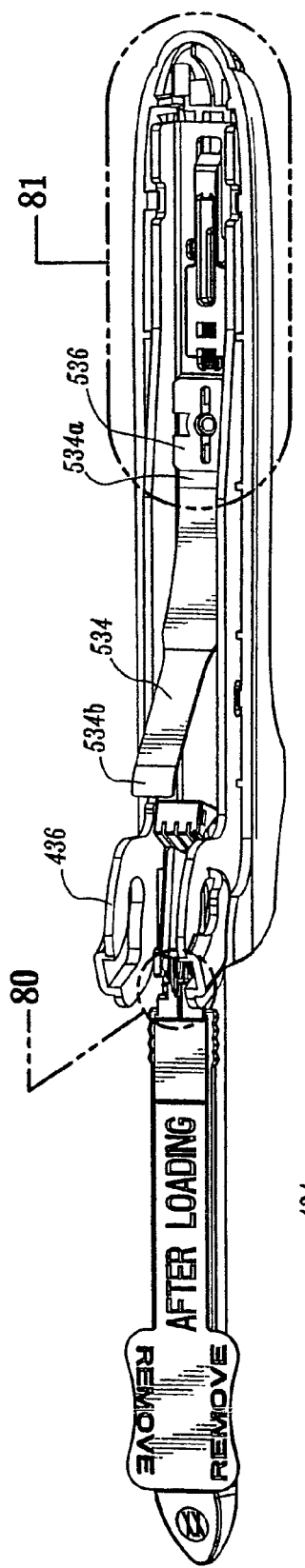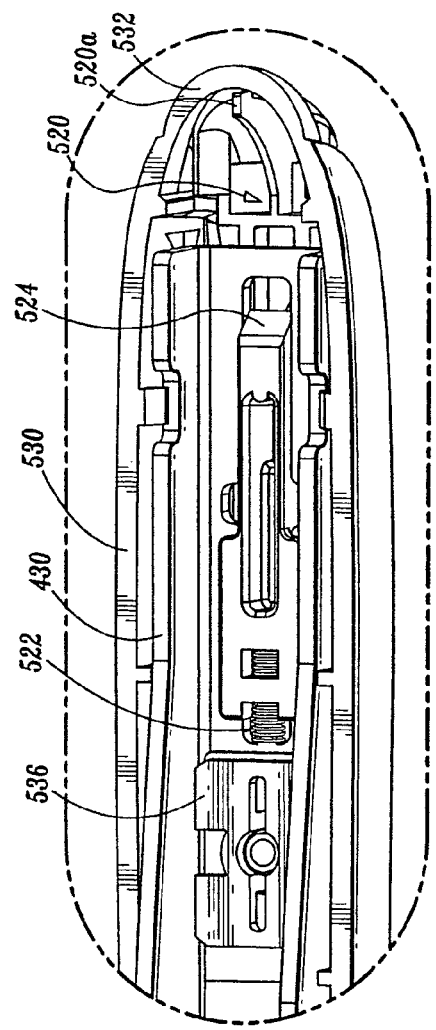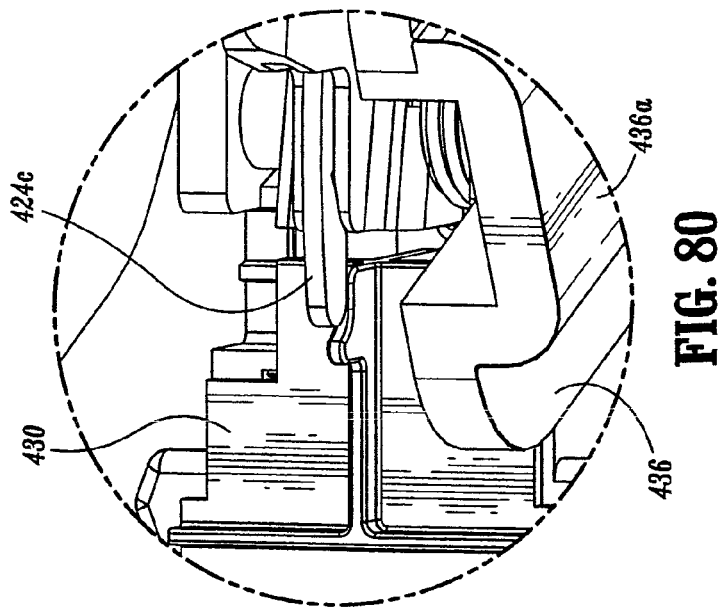
FIG. 79
FIG. 81
FIG. 80

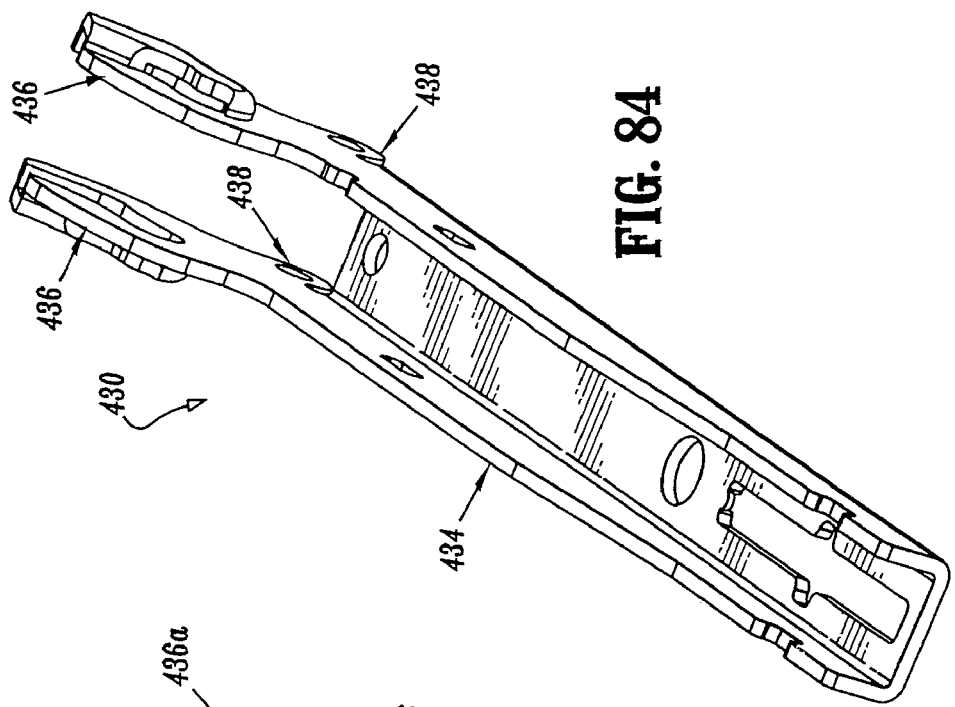
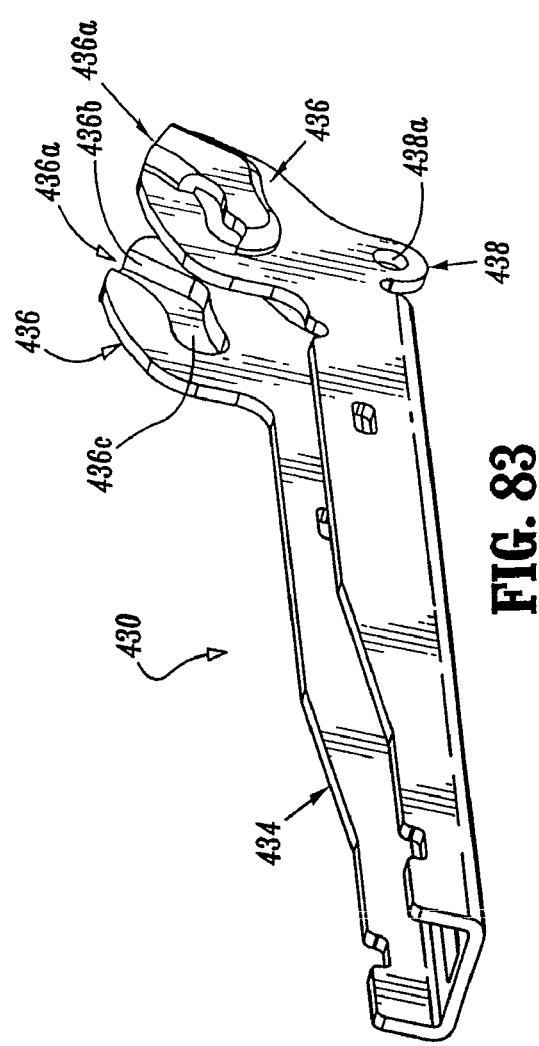
FIG. 84
FIG. 83

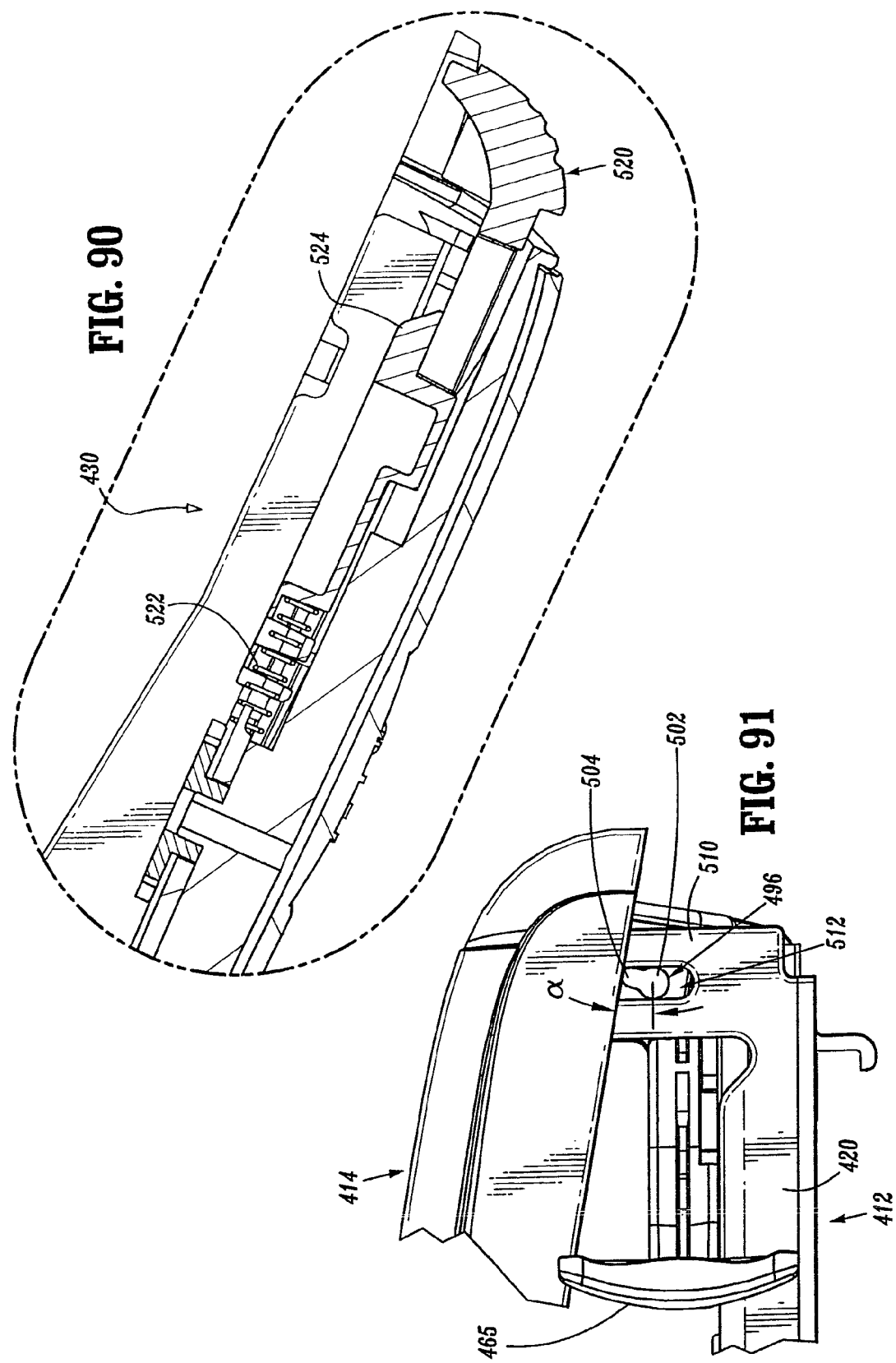

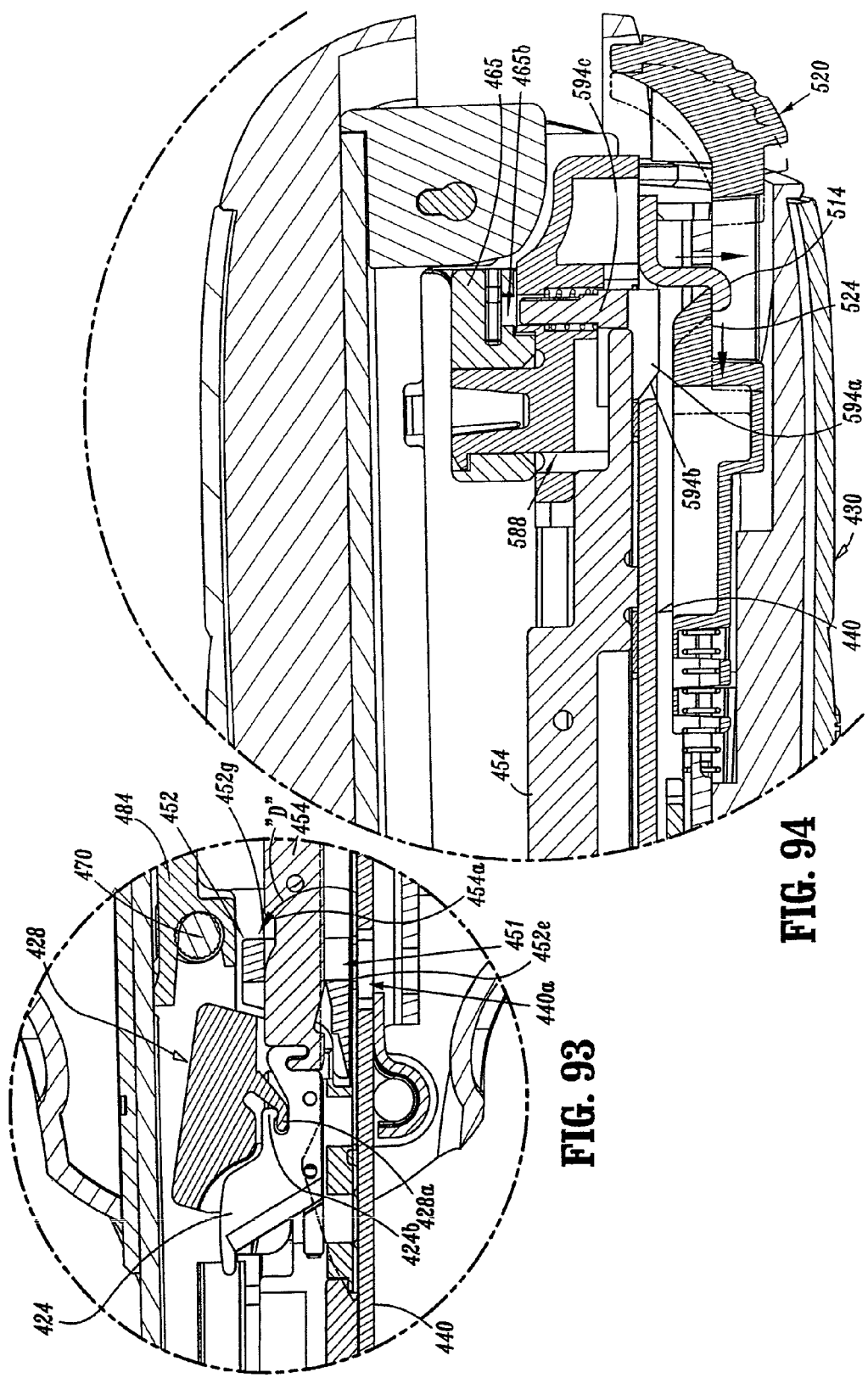

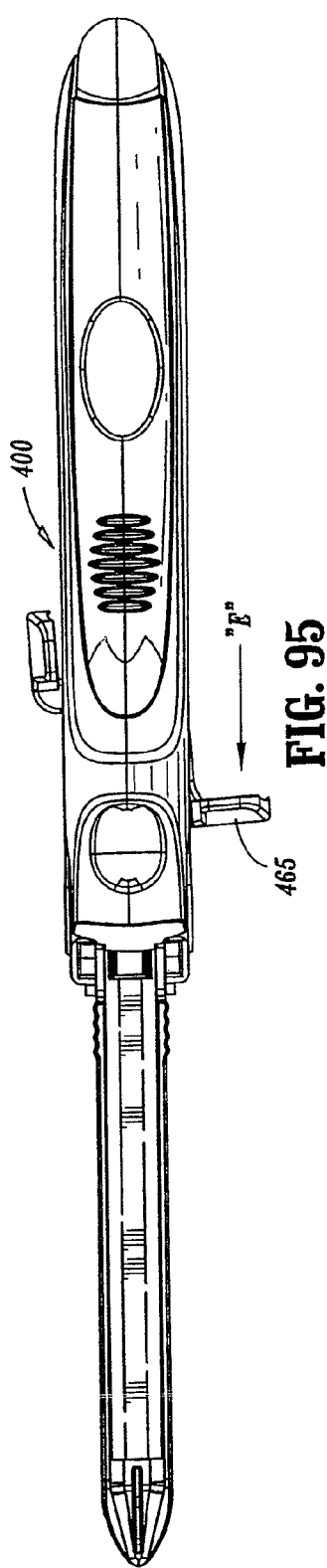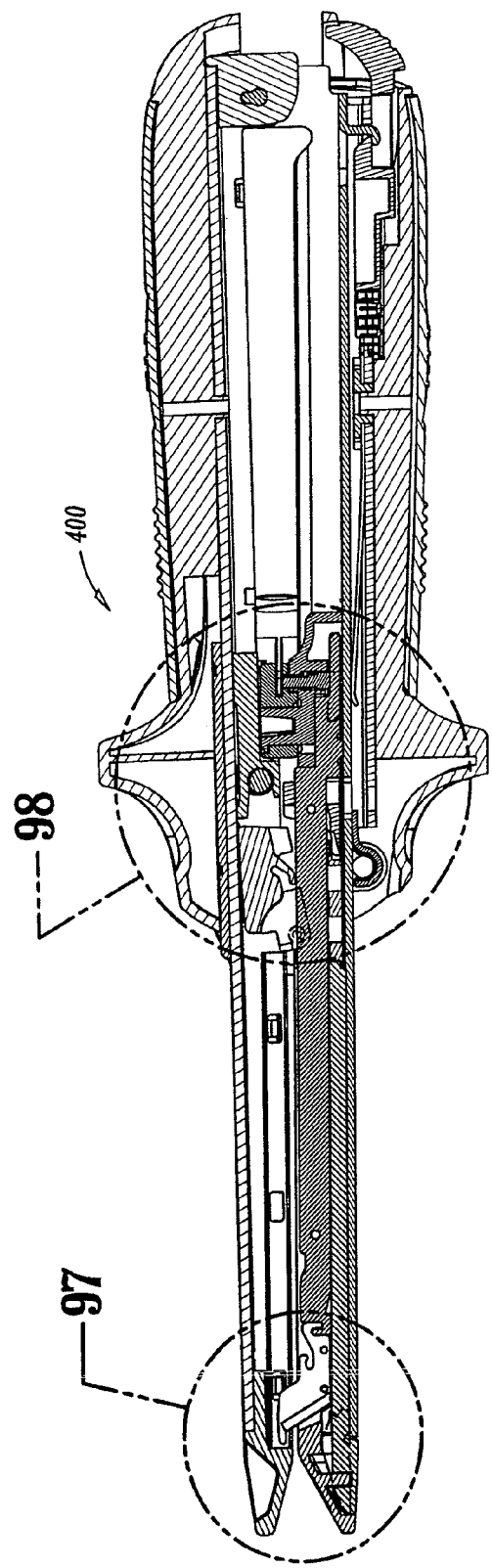
FIG. 95
FIG. 96

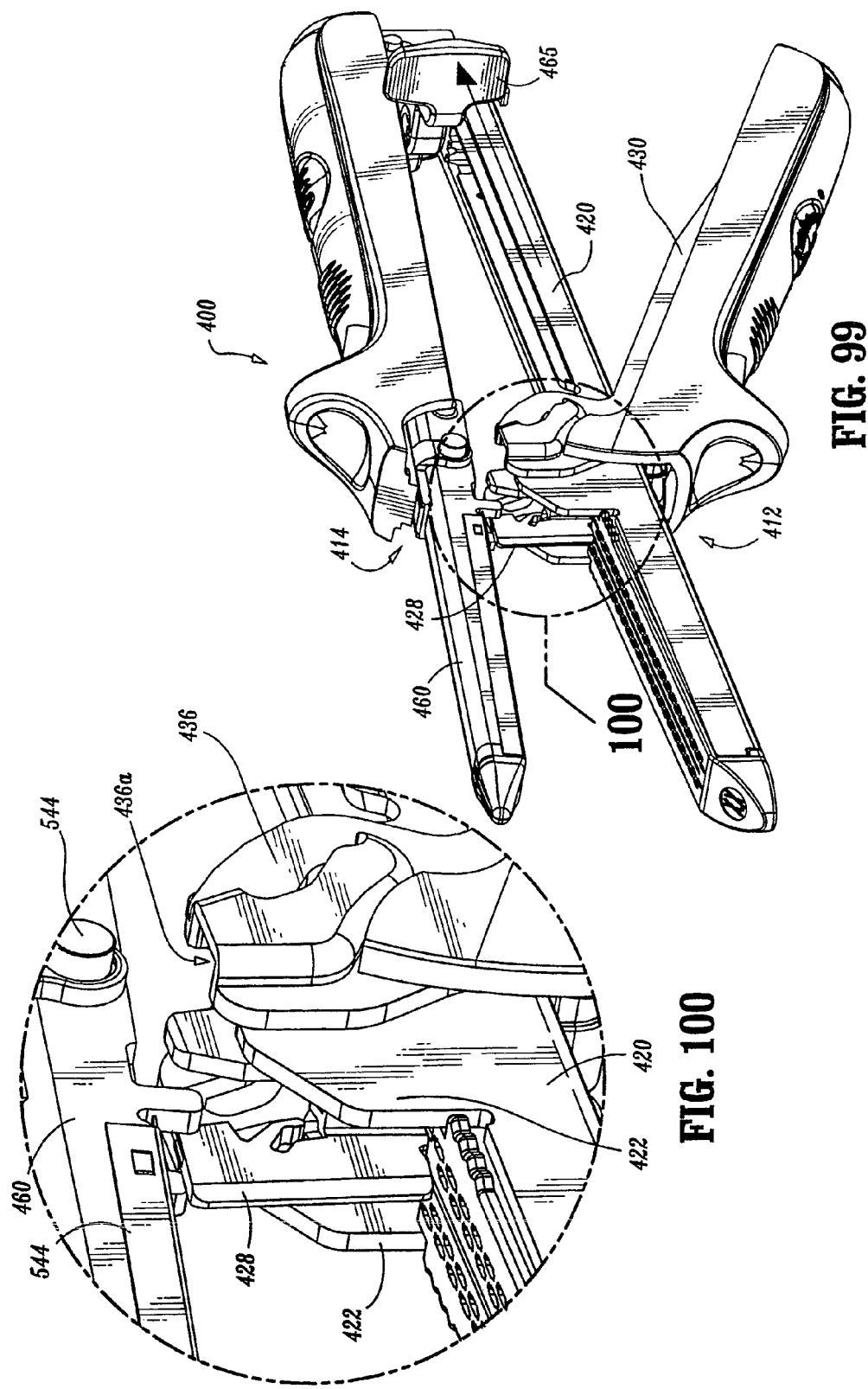

SURGICAL FASTENER APPLYING APPARATUS

CROSS-REFERENCE TO RELATED APPLICATIONS

The present application is a Continuation Application claiming the benefit of and priority to U.S. patent application Ser. No. 12/115,612, filed on May 6, 2008, now U.S. Pat. No. 7,631 794, which is a Continuation Application claiming the benefit of and priority to U.S. patent application Ser. No. 11/699,686, filed on Jan. 29, 2007, now U.S. Pat. No. 7,631, 793, which is a Continuation Application claiming the benefit of and priority to U.S. patent application Ser. No. 10/508,191, filed on Apr. 22, 2005, now U.S. Pat. No. 7,334,717, which is a 35 U.S.C. §371 National Filing of International Application Serial No. PCT/US03/08342, filed on Mar. 19, 2003, which, in turn, claims the benefit of and priority to U.S. Provisional Application Ser. No. 60/356,761, filed on Mar. 19, 2002and U.S. Provisional Application Ser. No. 60/416,371, filed on Oct. 4, 2002, the entire contents of each of which being incorporated herein by reference.

U.S. patent application Ser. No. 10/508,191, filed on Apr. 22, 2005, is also a Continuation-in-Part Application claiming the benefit of and priority to U.S. patent application Ser. No. 10/490,517, filed on Mar. 23, 2004, now U.S. Pat. No. 7,032, 799, which is a 35 U.S.C. §371 National Filing of International Application Serial No. PCT/US02/31963, filed on Oct. 4, 2002, which, in turn, claims the benefit of and priority to U.S. Provisional Application Ser. No. 60/327,369, filed on Oct. 5, 2001, the benefit of which is claimed herein, and the entire contents of each of which being incorporated herein by reference.

The present application is also a Continuation-in-Part Application claiming the benefit of and priority to U.S. patent application Ser. No. 12/186,269, filed on Aug. 5, 2008, now U.S. Pat. No. 7,721,933which is a Continuation Application claiming the benefit of and priority to U.S. patent application Ser. No. 12/011,419, filed on Jan. 24, 2008, now U.S. Pat. No. 7,568,604, which is a Continuation Application claiming the benefit of and priority to U.S. patent application Ser. No. 11/699,620, filed on Jan. 29, 2007, now U.S. Pat. No. 7,419, 081, which is a Continuation Application claiming the benefit of and priority to U.S. patent application Serial No. 11/356, 912, filed on Feb. 16, 2006, now U.S. Pat. No. 7,293,685, which is a Divisional Application claiming the benefit of and priority to U.S. patent application Ser. No. 11/292,736, filed on Dec. 2, 2005, now U.S. Pat. No. 7,140,527, which is a Divisional Application claiming the benefit of and priority to U.S. patent application Ser. No. 10/399,071, filed on Apr. 10, 2003, now U.S. Pat. No. 7,055,730, which is a 35 U.S.C. §371National Filing of International Application No. PCT/US01/32213, filed Oct. 15, 2001, which claims the benefit of and priority to U.S. Provisional Application Ser. No. 60/240, 461, filed on Oct. 13, 2000, the entire contents of each of which being incorporated herein by this reference.

BACKGROUND

1. Technical Field

The present disclosure relates to surgical fastener applying apparatus and, more particularly, to surgical fastener applying apparatus for applying a plurality of surgical fasteners to body tissue.

2. Discussion of Related Art

Surgical apparatus or instruments, wherein tissue is first grasped or clamped between opposing jaw structures and then joined by means of surgical fasteners are well known in the art. In some such instruments a knife is provided to cut the tissue which has been joined by the fasteners. The fasteners are typically in the form of surgical staples, although, other surgical fasteners may also be utilized, such as, for example, clips or two part polymeric surgical fasteners.

Instruments for applying surgical fasteners typically include two elongated beam members which are respectively used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the are driven from the cartridge assembly. Where two part fasteners are used, this beam member typically carries the mating part, e.g. the receiver, to the fasteners driven from the cartridge assembly. Generally, the staple formation process is affected by the interaction between one or more longitudinally moving camming members and a series of individual staple pushers. As the camming members travel longitudinally through the cartridge carrying beam member, the individual pusher members are biased laterally, thus acting upon the staples to sequentially eject the staples from the cartridge. A knife may travel with the camming members or the individual pusher members between the staple rows to cut the tissue between the rows of formed staples. Examples of such instruments are disclosed in U.S. Pat. Nos. 3,079,606 and 3,490,675, each of which is incorporated herein in its entirety by reference.

A later surgical apparatus or instrument, disclosed in U.S. Pat. No. 3,499,591, incorporated herein in its entirety by reference, applies a double row of staples on each side of the incision. This is accomplished by providing a cartridge assembly in which at least one camming member moves through an elongate guide path between two sets of staggered staple carrying grooves. Staple pushers are located within the grooves and are positioned in such a manner so as to be contacted by the longitudinally moving camming member to effect ejection of the staples.

A need exists for improved surgical fastener applying apparatus, and for improved mechanisms and methods for producing improved surgical fastener applying apparatus.

SUMMARY

The present disclosure relates to surgical fastener applying apparatus for sequentially applying a plurality of surgical fasteners to body tissue.

According to one aspect of the present disclosure, a surgical fastener applying apparatus is disclosed including an anvil half-section having a proximal end portion and a distal end portion including an anvil which defines a fastener forming surface against which surgical fasteners are driven; a cartridge receiving half-section having a proximal end portion and a distal end portion, the cartridge receiving half-section being configured and adapted to releasably mate with the anvil half-section, the surgical fastener applying apparatus having an assembled configuration wherein the anvil half-section and the cartridge receiving half-section are positioned in juxtaposed alignment with each other, the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position; and a replaceable cartridge assembly receivable in the distal end portion of the cartridge receiving half-section. The cartridge assembly includes an upper surface and a plurality of surgical staples and surgical staple pushers, the surgical staples being ejectable by the pusher members from the cartridge assembly through openings in the upper surface, the cartridge assembly defining at least one slot for receiving at least one knife therein, the cartridge assembly including a safety lockout pivotably disposed along the upper surface of the cartridge assembly and movable from an unlocked orientation permitting assembly of the anvil half-section, to the cartridge receiving half-section to a locked orientation preventing assembly of the anvil half-section to the cartridge receiving-half section.

In one embodiment, the safety lockout is biased from the unlocked orientation to the locked orientation. Preferably, the safety lockout is biased by a spring. It is envisioned that the safety lockout includes a transverse horizontal surface formed on the underside thereof and which is configured and adapted to engage a member formed on a surface of the at least one knife. The transverse horizontal surface and the member of the at least one knife are configured and dimensioned such that when the at least one knife is displaced in a distal direction, the member of the at least one knife disengages from the transverse horizontal surface. It is envisioned that the member of the at least one knife is a hook.

In another embodiment, the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly assembled with cartridge receiving half-section. It is envisioned that the loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, the rocker defining a downwardly extending blocking surface which, when in the locked-out position, the rocker engages a cam bar and prevents displacement of the cam bar in a distal direction and when in the firing position the rocker disengages the cam bar and allows the cam bar to be displaced distally.

It is envisioned that the rocker defines an upper edge blocking surface, wherein when the rocker is in the locked-out position the upper edge blocking surface engages a knife actuating bar and prevents displacement of the knife actuating bar in a distal direction, and when the rocker is in the firing position the upper edge blocking surface disengages the knife actuating bar and allows the knife actuating bar to be displaced distally. The rocker is preferably biased to the locked-out position. The rocker is preferably adapted to be pivoted to the firing position when the anvil half-section is coupled to the cartridge receiving half-section.

In yet another embodiment, the surgical fastener applying apparatus further includes a gap adjustment mechanism operatively associated between the anvil half-section and the cartridge receiving half-section, wherein the gap adjustment mechanism is configured and adapted to vary the size of a gap between the distal end portions of the anvil half-section and the cartridge receiving half-section. It is envisioned that the gap adjustment mechanism includes a cam positioned between the anvil half-section and the cartridge receiving half-section when in the assembled condition, wherein manipulation of the cam results in the variation of the size of the gap between the distal ends of the anvil half-section and the cartridge receiving half-section.

Preferably, the cam includes a forward portion, a body portion and a rearward portion, wherein the body portion of the cam defines a central rotational axis and wherein the forward and rearward portions share a common axis which is spaced a distance from the central rotational axis. It is envisioned that body portion is rotationally disposed within apertures formed in the anvil half section and the forward and rearward portions rest against respective surfaces of opposed hinge plates extending from the cartridge receiving half-section, wherein rotation of the cam about the central rotational axis results in the forward and rearward portions of the cam to displace the cartridge receiving half-section.

It is envisioned that the gap adjustment mechanism includes a cam lock configured and adapted to engage the body portion of the cam and to prevent rotation of the cam after adjustment of the gap.

In another embodiment, the clamping lever includes a body portion having a pair of juxtaposed hinge plates each defining an access channel formed therein, each access channel being is configured and dimensioned to receive a respective mounting boss extending laterally from the anvil half-section, such that as the clamping lever is approximated toward the cartridge receiving half-section, the access channels guide the mounting bosses therethrough to properly assemble the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

In yet another embodiment, the proximal end of the cartridge receiving half-section includes a pair of upstanding juxtaposed pivot plates each including a pin receiving slot formed therein. The proximal end of the anvil half-section includes a pin extending laterally from either side thereof, the pin being positionable within the pin receiving slots formed in the pivot plates of the cartridge receiving half-section. The pin preferably extends laterally from the proximal end of the anvil half-section is non-round in cross-section, and wherein the shape of the pin cooperates with the pin receiving slot to limit the angle at which the anvil half-section can be approximated to the cartridge receiving half-section in order to effectuate proper assembly. It is envisioned that the angle is less than about 15°. Preferably, the pin has a pear shape cross-section defined by a larger lower portion and a smaller upper portion.

In another embodiment, the surgical fastener applying apparatus includes a firing slide operatively associated with the cartridge receiving half-section, the firing slide including a firing lever pivotably coupled thereto, wherein the firing lever is adapted to enable the surgical fastener applying apparatus to be fired from either side thereof. The firing slide includes, in one embodiment, a pair of cam bars configured and adapted to sequentially expel the plurality of fasteners in a direction transverse to the direction of movement of the pair of cam bars, and a knife actuating bar positioned between the pair of cam bars for displacing the knife in the direction of movement of the cam bars.

The firing slide includes, in another embodiment, a slide block having a hub extending therefrom for receipt in a pivot hole formed in the firing lever; and a pedal having a pin reciprocally received in and extending from a hole formed in the slide block, such that as the firing slide is displaced in a distal direction the pin from the pedal extends into a recess formed in the firing lever to thereby prevent the firing lever from thereafter pivoting about the hub of the slide block.

In another aspect of the present disclosure, a surgical fastener applying apparatus is disclosed including an anvil half-section; a cartridge receiving half-section configured and adapted to releasably mate with the anvil half-section; and a gap adjustment mechanism operatively associated between the anvil half-section and the cartridge receiving half-section, wherein the gap adjustment mechanism is configured and adapted to vary the size of the gap between the distal end portions of the anvil half-section and the cartridge receiving half-section.

In one embodiment, the gap adjustment mechanism includes a cam positioned between the anvil half-section and the cartridge receiving half-section when in the assembled condition, wherein manipulation of the cam results in the variation of the size of the gap between the distal ends of the anvil half-section and the cartridge receiving half-section. It is envisioned that the cam includes a forward portion, a body portion and a rearward portion, wherein the body portion of the cam defines a central rotational axis and wherein the forward and rearward portions share a common axis which is spaced a distance from the central rotational axis. The body portion is rotationally disposed within apertures formed in the anvil half section and the forward and rearward portions rest against respective surfaces of opposed hinge plates extending from the cartridge receiving half-section, wherein rotation of the cam about the central rotational axis results in the forward and rearward portions of the cam to displace the cartridge receiving half-section.

It is envisioned that the gap adjustment mechanism includes a cam lock configured and adapted to engage the body portion of the cam and to prevent rotation of the cam after adjustment of the gap.

In another embodiment, the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly loaded onto cartridge receiving half-section. The loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, when in the locked-out position, the rocker engages a cam bar and prevents displacement of the cam bar in a distal direction and when in the firing position the rocker disengages the cam bar and allows the cam bar to be displaced distally.

It is envisioned that the rocker defines an upper edge blocking surface, wherein when the rocker is in the locked-out position the upper edge blocking surface engages a knife actuating bar and prevents displacement of the knife actuating bar in a distal direction and when the rocker is in the firing position the upper edge blocking surface disengages the knife actuating bar and allows the knife actuating bar to be displaced distally. Preferably, the rocker is biased to the locked-out position. It is contemplated that the rocker is pivoted to the firing position when the anvil half-section is coupled to the cartridge receiving half-section.

In another embodiment, the clamping lever includes a body portion having a pair of juxtaposed hinge plates each defining an access channel formed therein, wherein each access channel is configured and dimensioned to receive a respective mounting boss extending laterally from the anvil half-section, wherein as the clamping lever is approximated toward the cartridge receiving half-section, the access channels guide the mounting bosses therethrough to properly mate the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

In another embodiment, the proximal end of the cartridge receiving half-section includes a pair of upstanding juxtaposed pivot plates each including a pin receiving slot formed therein. The proximal end of the anvil half-section includes a pin extending laterally from either side thereof, wherein the pin at the proximal end of the anvil half-section is positionable within the pin receiving slots formed in the pivot plates of the cartridge receiving half-section.

The pin extending laterally from the proximal end of the anvil half-section is non-round, and wherein the pin limits the angle at which the anvil half-section can be approximated to the cartridge receiving half-section in order to effectuate proper assembly. Preferably, the angle is less than about 15°. It is envisioned that the pin has a pear shape cross-section defined by a larger lower portion and a smaller upper portion.

In another embodiment, the surgical fastener applying apparatus includes a firing slide operatively associated with the cartridge receiving half-section, the firing slide including a firing lever pivotably coupled thereto, wherein the firing lever enables the surgical fastener applying apparatus to be fired from either side thereof. It is envisioned that the firing slide includes, in one embodiment, a pair of cam bars configured and adapted to sequentially expel the plurality of fasteners in a direction transverse to the direction of movement of the pair of cam bars, a knife actuating bar positioned between the pair of cam bars for displacing the knife in the direction of movement of the cam bars.

It is envisioned that the firing slide includes, in another embodiment, a slide block having a hub extending therefrom for receipt in a pivot hole formed in the firing lever, and a pedal having a pin reciprocally received in a hole formed in the slide block, wherein as the firing slide is displaced in a distal direction the pin from the pedal extends into a recess formed in the firing lever to thereby prevent the firing lever from thereafter pivoting about the hub of the slide block.

According to another aspect of the present disclosure, a surgical fastener applying apparatus is disclosed which includes an anvil half-section; and a cartridge receiving half-section configured and adapted to releasably mate with the anvil half-section, wherein the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly loaded onto cartridge receiving half-section.

It is envisioned that the loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, when in the locked-out position, the rocker engages a cam bar and prevents displacement of the cam bar in a distal direction and when in the firing position the rocker disengages the cam bar and allows the cam bar to be displaced distally.

The rocker defines an upper edge blocking surface, wherein when the rocker is in the locked-out position the upper edge blocking surface engages a knife actuating bar and prevents displacement of the knife actuating bar in a distal direction and when the rocker is in the firing position the upper edge blocking surface disengages the knife actuating bar and allows the knife actuating bar to be displaced distally. It is envisioned that the rocker is biased to the locked-out position. Preferably, the rocker is pivoted to the firing position when the anvil half-section is coupled to the cartridge receiving half-section.

It is envisioned that the clamping lever includes a body portion having a pair of juxtaposed hinge plates each defining an access channel formed therein, wherein each access channel is configured and dimensioned to receive a respective mounting boss extending laterally from the anvil half-section, wherein as the clamping lever is approximated toward the cartridge receiving half-section, the access channels guide the mounting bosses therethrough to properly mate the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

In another embodiment, the proximal end of the cartridge receiving half-section includes a pair of upstanding juxtaposed pivot plates each including a pin receiving slot formed therein. The proximal end of the anvil half-section includes a pin extending laterally from either side thereof, and wherein the pin at the proximal end of the anvil half-section is positionable within the pin receiving slots formed in the pivot plates of the cartridge receiving half-section.

It is envisioned that the pin extending laterally from the proximal end of the anvil half-section is non-round, wherein the pin limits the angle at which the anvil half-section can be approximated to the cartridge receiving half-section in order to effectuate proper assembly. Preferably, the angle is less than about 15°. It is envisioned that the pin has a pear shape cross-section defined by a larger lower portion and a smaller upper portion.

In another embodiment, the surgical fastener applying apparatus includes a firing slide operatively associated with the cartridge receiving half-section, the firing slide including a firing lever pivotably coupled thereto, wherein the firing lever enables the surgical fastener applying apparatus to be fired from either side thereof.

The firing slide includes, in one embodiment, a pair of cam-ears configured and adapted to sequentially expel the plurality of fasteners in a direction transverse to the direction of movement of the pair of cam bars, a knife actuating bar positioned between the pair of cam bars for displacing the knife in the direction of movement of the cam bars.

The firing slide includes, in another embodiment, a slide block having a hub extending therefrom for receipt in a pivot hole formed in the firing lever; and a pedal having a pin reciprocally received in a hole formed in the slide block, wherein as the firing slide is displaced in a distal direction the pin from the pedal extends into a recess formed in the firing lever to thereby prevent the firing lever from thereafter pivoting about the hub of the slide block.

It is envisioned that the surgical fastener applying apparatus further includes a replaceable cartridge assembly receivable in the distal end portion of the cartridge receiving half-section, the cartridge assembly having an upper surface and a plurality of surgical staples and surgical staple pushers, the surgical staples being ejectable by the pusher members from the cartridge assembly through openings in the upper surface, the cartridge assembly defining at least one slot for receiving at least one knife therein, the cartridge assembly including a safety lockout pivotably disposed along the upper surface of cartridge assembly and movable from an unlocked orientation permitting assembly of the anvil half-section to the cartridge receiving half-section to a locked orientation preventing assembly of the anvil half-section to the cartridge receiving-half section.

The safety lockout is biased from the unlocked orientation to the locked orientation. Preferably, the safety lockout is biased by a spring. The safety lockout includes a transverse horizontal surface formed on the underside thereof which transverse horizontal surface is configured and adapted to engage a hook formed on an upper surface of the at least one knife. The transverse horizontal surface and the hook are configured and dimensioned such that when the at least one knife is displaced in a distal direction, the hook disengages from the transverse horizontal surface.

In yet another aspect of the present disclosure, a surgical fastener applying apparatus is disclosed which includes an anvil half-section; and a cartridge receiving half-section configured and adapted to releasably mate with the anvil half-section, the cartridge half-section including a pivotable clamping lever, wherein movement of the clamping lever from a first position to a second position moves the cartridge receiving and anvil half-sections to the fully clamped position, and wherein the clamping lever includes a body portion having a pair of juxtaposed hinge plates each defining an access channel formed therein, wherein each access channel is configured and dimensioned to receive a respective mounting boss extending laterally from the anvil half-section, wherein as the clamping lever is approximated toward the cartridge receiving half-section, the access channels guide the mounting bosses therethrough to properly mate the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

It is envisioned that the proximal end of the cartridge receiving half-section includes a pair of upstanding juxtaposed pivot plates each including a pin receiving slot formed therein. The proximal end of the anvil half-section includes a pin extending laterally from either side thereof, and wherein the pin at the proximal end of the anvil half-section is positionable within the pin receiving slots formed in the pivot plates of the cartridge receiving half-section. The pin preferably extends laterally from the proximal end of the anvil half-section is non-round, wherein the pin limits the angle at which the anvil half-section can be approximated to the cartridge receiving half-section in order to effectuate proper assembly. It is envisioned that the angle is less than about 15°. Preferably, the pin has a pear shape cross-section defined by a larger lower portion and a smaller upper portion.

It is further envisioned that the surgical fastener applying apparatus includes a firing slide operatively associated with the cartridge receiving half-section, the firing slide including a firing lever pivotably coupled thereto, wherein the firing lever enables the surgical fastener applying apparatus to be fired from either side thereof.

It is contemplated that the firing slide includes, in one embodiment, a pair of cam bars configured and adapted to sequentially expel the plurality of fasteners in a direction transverse to the direction of movement of the pair of cam bars, a knife actuating bar positioned between the pair of cam bars for displacing the knife in the direction of movement of the cam bars.

It is further contemplated that the firing slide includes, in another embodiment, a slide block having a hub extending therefrom for receipt in a pivot hole formed in the firing lever; and a pedal having a pin reciprocally received in a hole formed in the slide block, wherein as the firing slide is displaced in a distal direction the pin from the pedal extends into a recess formed in the firing lever to thereby prevent the firing lever from thereafter pivoting about the hub of the slide block.

It is envisioned that the surgical fastener applying apparatus includes a replaceable cartridge assembly receivable in the distal end portion of the cartridge receiving half-section, the cartridge assembly having an upper surface and a plurality of surgical staples abutting surgical staple pushers, the surgical staples being ejectable from the cartridge assembly through openings in the upper surface, the cartridge assembly defining at least one slot for receiving at least one knife therein, the cartridge assembly including a safety lockout pivotably disposed along the upper surface of cartridge assembly and movable from an unlocked orientation permitting assembly of the anvil half-section to the cartridge receiving half-section to a locked orientation preventing assembly of the anvil half-section to the cartridge receiving-half section.

The safety lockout is biased from the unlocked orientation to the locked orientation. Preferably, the safety lockout is biased by a spring. The safety lockout includes a transverse horizontal surface formed on the underside thereof which transverse horizontal surface is configured and adapted to engage a hook formed on an upper surface of the at least one knife. It is envisioned that the transverse horizontal surface and the hook are configured and dimensioned such that when the at least one knife is displaced in a distal direction, the hook disengages from the transverse horizontal surface.

It is envisioned that the surgical fastener applying apparatus further includes a replaceable cartridge assembly receivable in the distal end portion of the cartridge receiving half-section, the cartridge assembly having an upper surface and a plurality of surgical staples and surgical staple pushers, the surgical staples being ejectable by the pusher members from the cartridge assembly through openings in the upper surface, the cartridge assembly defining at least one slot for receiving at least one knife therein, the cartridge assembly including a safety lockout pivotably disposed along the upper surface of the cartridge assembly and movable from an unlocked orientation permitting assembly of the anvil half-section, to the cartridge receiving half-section to a locked orientation preventing assembly of the anvil half-section to the cartridge receiving-half section.

It is envisioned that the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly loaded onto cartridge receiving half-section.

The loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, when in the locked-out position, the rocker engages a cam bar and prevents displacement of the cam bar in a distal direction and when in the firing position the rocker disengages the cam bar and allows the cam bar to be displaced distally. The rocker defines an upper edge blocking surface, wherein when the rocker is in the locked-out position the upper edge blocking surface engages a knife actuating bar and prevents displacement of the knife actuating bar in a distal direction and when the rocker is in the firing position the upper edge blocking surface disengages the knife actuating bar and allows the knife actuating bar to be displaced distally. Preferably, the rocker is biased to the locked-out position. The rocker is pivoted to the firing position when the anvil half-section is coupled to the cartridge receiving half-section.

It is envisioned that surgical fastener applying apparatus further includes a gap adjustment mechanism operatively associated between the anvil half-section and the cartridge receiving half-section, wherein the gap adjustment mechanism is configured and adapted to vary the size of a gap between the distal end portions of the anvil half-section and the cartridge receiving half-section.

The gap adjustment mechanism includes a cam positioned between the anvil half-section and the cartridge receiving half-section when in the mated condition, wherein manipulation of the cam results in the variation of the size of the gap between the distal ends of the anvil half-section and the cartridge receiving half-section. It is envisioned that the cam includes a forward portion, a body portion and a rearward portion, wherein the body portion of the cam defines a central rotational axis and wherein the forward and rearward portions share a common axis which is spaced a distance from the central rotational axis. The body portion is rotationally disposed within apertures formed in the anvil half section and the forward and rearward portions rest against respective shoulders of opposed hinge plates extending from the cartridge receiving half-section, wherein rotation of the cam about the central rotational axis results in the forward and rearward portions of the cam to displace the cartridge receiving half-section.

According to still another aspect of the present disclosure, a surgical fastener applying apparatus is disclosed which includes an anvil half-section; and a cartridge receiving half-section configured and adapted to releasably mate with the anvil half-section, wherein the proximal end of the cartridge receiving half-section includes a pair of upstanding juxtaposed pivot plates each including a pin receiving slot formed therein.

It is envisioned that the proximal end of the anvil half-section includes a pin extending laterally from either side thereof, wherein the pin at the proximal end of the anvil half-section is positionable within the pin receiving slots formed in the pivot plates of the cartridge receiving half-section. Preferably, the pin extending laterally from the proximal end of the anvil half-section is non-round, and wherein the pin limits the angle at which the anvil half-section can be approximated to the cartridge receiving half-section in order to effectuate proper assembly. The angle is preferably less than about 15°. Preferably, the pin has a pear shape cross-section defined by a larger lower portion and a smaller upper portion.

It is envisioned that the surgical fastener applying apparatus includes a firing slide operatively associated with the cartridge receiving half-section, the firing slide including a firing lever pivotably coupled thereto, wherein the firing lever enables the surgical fastener applying apparatus to be fired from either side thereof.

It is further envisioned that, the firing slide includes, in one embodiment, a pair of cam bars configured and adapted to sequentially expel the plurality of fasteners in a direction transverse to the direction of movement of the pair of cam bars, a knife actuating bar positioned between the pair of cam bars for displacing the knife in the direction of movement of the cam bars.

It is envisioned that, the firing slide includes, in yet another embodiment, a slide block having a hub extending therefrom for receipt in a pivot hole formed in the firing lever; and a pedal having a pin reciprocally received in a hole formed in the slide block, wherein as the firing slide is displaced in a distal direction the pin from the pedal extends into a recess formed in the firing lever to thereby prevent the firing lever from thereafter pivoting about the hub of the slide block.

In one embodiment, the surgical fastener applying apparatus further includes a replaceable cartridge assembly receivable in the distal end portion of the cartridge receiving half-section, the cartridge assembly having an upper surface and a plurality of surgical staples and surgical staple pushers, the surgical staples being ejectable by the pusher members from the cartridge assembly through openings in the upper surface, the cartridge assembly defining at least one slot for receiving at least one knife therein, the cartridge assembly including a safety lockout pivotably disposed along the upper surface of cartridge assembly and movable from an unlocked orientation permitting assembly of the anvil half-section to the cartridge receiving half-section to a locked orientation preventing assembly of the anvil half-section to the cartridge receiving-half section.

The safety lockout is preferably biased from the unlocked orientation to the locked orientation. It is envisioned that the safety lockout is biased by a spring. The safety lockout includes a transverse horizontal surface formed on the underside thereof which transverse horizontal surface is configured and adapted to engage a hook formed on an upper surface of the at least one knife. The transverse horizontal surface and the hook are configured and dimensioned such that when the at least one knife is displaced in a distal direction, the hook disengages from the transverse horizontal surface.

It is envisioned that the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly loaded onto cartridge receiving half-section. The loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, when in the locked-out position, the rocker engages a cam bar and prevents displacement of the cam bar in a distal direction and when in the firing position the rocker disengages the cam bar and allows the cam bar to be displaced distally.

The rocker defines an upper edge blocking surface, wherein when the rocker is in the locked-out position the upper edge blocking surface engages a knife actuating bar and prevents displacement of the knife actuating bar in a distal direction and when the rocker is in the firing position the upper edge blocking surface disengages the knife actuating bar and allows the knife actuating bar to be displaced distally. The rocker is preferably biased to the locked-out position. Preferably, the rocker is pivoted to the firing position when the anvil half-section is coupled to the cartridge receiving half-section.

In another embodiment, the surgical fastener applying apparatus includes a gap adjustment mechanism operatively associated between the anvil half-section and the cartridge receiving half-section, wherein the gap adjustment mechanism is configured and adapted to vary the size of a gap between the distal end portions of the anvil half-section and the cartridge receiving half-section. The gap adjustment mechanism includes a cam positioned between the anvil half-section and the cartridge receiving half-section when in the mated condition, wherein manipulation of the cam results in the variation of the size of the gap between the distal ends of the anvil half-section and the cartridge receiving half-section.

The cam includes a forward portion, a body portion and a rearward portion, wherein the body portion of the cam defines a central rotational axis and wherein the forward and rearward portions share a common axis which is spaced a distance from the central rotational axis. The body portion is rotationally disposed within apertures formed in the anvil half section and the forward and rearward portions rest against respective shoulders of opposed hinge plates extending from the cartridge receiving half-section, wherein rotation of the cam about the central rotational axis results in the forward and rearward portions of the cam to displace the cartridge receiving half-section. Preferably, the gap adjustment mechanism includes a cam lock configured and adapted to engage the body portion of the cam and to prevent rotation of the cam after adjustment of the gap.

It is envisioned that the clamping lever includes a body portion having a pair of juxtaposed hinge plates each defining an access channel formed therein, wherein each access channel is configured and dimensioned to receive a respective mounting boss extending laterally from the anvil half-section, wherein as the clamping lever is approximated toward the cartridge receiving half-section, the access channels guide the mounting bosses therethrough to properly mate the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

In yet another aspect of the present disclosure, a surgical fastener applying apparatus is provided which includes an anvil half-section, a cartridge receiving half-section configured and adapted to releasably mate with the anvil half-section, a replaceable cartridge assembly receivable in the distal end portion of the cartridge receiving half-section, and a firing slide operatively associated with the cartridge receiving half-section, the firing slide including a firing lever pivotably coupled thereto, wherein the firing lever enables the surgical fastener applying apparatus to be fired from either side thereof.

It is envisioned that the firing slide includes a pair of cam bars configured and adapted to sequentially expel the plurality of fasteners in a direction transverse to the direction of movement of the pair of cam bars, a knife actuating bar positioned between the pair of cam bars for displacing the knife in the direction of movement of the cam bars.

The firing slide includes, in another embodiment, a slide block having a hub extending therefrom for receipt in a pivot hole formed in the firing lever; and a pedal having a pin reciprocally received in a hole formed in the slide block, wherein as the firing slide is displaced in a distal direction the pin from the pedal extends into a recess formed in the firing lever to thereby prevent the firing lever from thereafter pivoting about the hub of the slide block.

It is envisioned that the surgical fastener applying apparatus further includes a replaceable cartridge assembly receivable in the distal end portion of the cartridge receiving half-section, the cartridge assembly having an upper surface and a plurality of surgical staples and surgical staple pushers, the surgical staples being ejectable by the pusher members from the cartridge assembly through openings in the upper surface, the cartridge assembly defining at least one slot for receiving at least one knife therein, the cartridge assembly including a safety lockout pivotably disposed along the upper surface of the cartridge assembly and movable from an unlocked orientation permitting assembly of the anvil half-section, to the cartridge receiving half-section to a locked orientation preventing assembly of the anvil half-section to the cartridge receiving-half section.

Preferably, the safety lockout is biased by a spring. The safety lockout includes a transverse horizontal surface formed on the underside thereof which transverse horizontal surface is configured and adapted to engage a hook formed on an upper surface of the at least one knife. The transverse horizontal surface and the hook are configured and dimensioned such that when the at least one knife is displaced in a distal direction, the hook disengages from the transverse horizontal surface.

It is envisioned that the cartridge receiving half-section includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly loaded onto cartridge receiving half-section.

The loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, when in the locked-out position, the rocker engages a cam bar and prevents displacement of the cam bar in a distal direction and when in the firing position the rocker disengages the cam bar and allows the cam bar to be displaced distally.

The rocker defines an upper edge blocking surface, wherein when the rocker is in the locked-out position the upper edge blocking surface engages a knife actuating bar and prevents displacement of the knife actuating bar in a distal direction and when the rocker is in the firing position the upper edge blocking surface disengages the knife actuating bar and allows the knife actuating bar to be displaced distally. Preferably, the rocker is biased to the locked-out position. The rocker is pivoted to the firing position when the anvil half-section is coupled to the cartridge receiving half-section.

It is envisioned that the surgical fastener applying apparatus further includes a gap adjustment mechanism operatively associated between the anvil half-section and the cartridge receiving half-section, wherein the gap adjustment mechanism is configured and adapted to vary the size of a gap between the distal end portions of the anvil half-section and the cartridge receiving half-section. The gap adjustment mechanism includes a cam positioned between the anvil half-section and the cartridge receiving half-section when in the mated condition, wherein manipulation of the cam results in the variation of the size of the gap between the distal ends of the anvil half-section and the cartridge receiving half-section.

The cam includes a forward portion, a body portion and a rearward portion, wherein the body portion of the cam defines a central rotational axis and wherein the forward and rearward portions share a common axis which is spaced a distance from the central rotational axis. The body portion is rotationally disposed within apertures formed in the anvil half section and the forward and rearward portions rest against respective shoulders of opposed hinge plates extending from the cartridge receiving half-section, wherein rotation of the cam about the central rotational axis results in the forward and rearward portions of the cam to displace the cartridge receiving half-section. Preferably, the gap adjustment mechanism includes a cam lock configured and adapted to engage the body portion of the cam and to prevent rotation of the cam after adjustment of the gap.

It is envisioned that the clamping lever includes a body portion having a pair of juxtaposed hinge plates each defining an access channel formed therein, wherein each access channel is configured and dimensioned to receive a respective mounting boss extending laterally from the anvil half-section, wherein as the clamping lever is approximated toward the cartridge receiving half-section, the access channels guide the mounting bosses therethrough to properly mate the anvil half-section with the cartridge receiving half-section.

Preferably, when the anvil receiving half-section is oriented in the horizontal plane and the clamping lever is in the first position, the opening to each access channel can be vertically accessed. It is envisioned that each access channel is generally orthogonal to the cartridge receiving half-section. It is further envisioned that each access channel faces angularly relative to the cartridge receiving half-section.

In one embodiment, the proximal end of the cartridge receiving half-section includes a pair of upstanding juxtaposed pivot plates each including a pin receiving slot formed therein. The proximal end of the anvil half-section includes a pin extending laterally from either side thereof, and wherein the pin at the proximal end of the anvil half-section is positionable within the pin receiving slots formed in the pivot plates of the cartridge receiving half-section. The pin extending laterally from the proximal end of the anvil half-section is non-round, wherein the pin limits the angle at which the anvil half-section can be approximated to the cartridge receiving half-section in order to effectuate proper assembly. It is contemplated that the angle is less than about 15°. Preferably, the pin has a pear shape cross-section defined by a larger lower portion and a smaller upper portion.

In yet another aspect of the present disclosure, a staple cartridge assembly receivable in a distal end portion of cartridge receiving half-section of a surgical stapler is disclosed. The staple cartridge assembly includes a safety lockout pivotably disposed along an upper surface of the cartridge assembly and movable from an unblocked orientation permitting assembly of an anvil half-section to the cartridge receiving half-section, to a locked orientation preventing assembly of the anvil half-section with the cartridge receiving half-section.

The safety lockout is biased from the unlocked orientation to the locked orientation. The safety lockout is biased by a spring. The safety lockout includes a transverse horizontal surface formed on the underside thereof and which is configured and adapted to engage a member formed on a surface of the at least one knife. Preferably, the transverse horizontal surface and the member of the at least one knife are configured and dimensioned such that when the at least one knife is displaced in a distal direction, the member of the at least one knife disengages from the transverse horizontal surface. It is envisioned that the at least one knife is a hook.

It is envisioned that the staple cartridge assembly apparatus further includes a loading and lockout mechanism operatively associated therewith, the loading and lockout mechanism being configured and adapted to facilitate loading of the cartridge assembly to the to the cartridge receiving half-section and to prevent firing of the surgical fastener applying apparatus until the cartridge assembly is properly assembly with cartridge receiving half-section. The loading and lockout mechanism includes a rocker pivotably mounted to the cartridge receiving half-section, the rocker having a locked-out position which prevents firing of the surgical fastener applying apparatus and a firing position which permits firing of the surgical fastener applying apparatus, the rocker defining a downwardly extending blocking surface which, when in the locked-out position, the rocker engages a cam bar and prevents displacement of the cam bar in a distal direction and when in the firing position the rocker disengages the cam bar and allows the cam bar to be displaced distally.

The rocker defines an upper edge blocking surface, wherein when the rocker is in the locked-out position the upper edge blocking surface engages a knife actuating bar and prevents displacement of the knife actuating bar in a distal direction, and when the rocker is in the firing position the upper edge blocking surface disengages the knife actuating bar and allows the knife actuating bar to be displaced distally. Preferably, the rocker is biased to the locked-out position. The rocker is adapted to be pivoted to the firing position when the anvil half-section is coupled to the cartridge receiving half-section.

It is envisioned that the staple cartridge assembly includes a series of finger grips formed along an upper side surface near a proximal end thereof.

In yet another aspect of the present disclosure, a surgical fastener applying apparatus is disclosed which includes an anvil half-section; and a cartridge receiving half-section configured and adapted to releasably mate with the anvil half-section, the cartridge receiving half-section including a pivotable clamping lever, wherein the clamping lever includes a body portion having a pair of juxtaposed hinge plates each defining a reinforced access channel formed therein for receiving a respective mounting boss extending laterally froth either side of the anvil half-section. Preferably, the access channels are shaped to guide the mounting bosses therethrough to properly assemble the anvil half-section with the cartridge receiving half-section.

In yet another aspect of the present disclosure, a surgical fastener applying apparatus is disclosed including an anvil half-section; and a cartridge receiving half-section configured and adapted to releasably mate with the anvil half-section, the cartridge receiving half-section including a pivotable clamping lever, wherein the clamping lever includes a body portion having a pair of juxtaposed hinge plates each defining an access channel formed therein for receiving a respective mounting boss extending laterally from either side of the anvil half-section, wherein a portion of the respective access channels are covered by portions of the hinge plate.

These objects together with other objects of the disclosure, along with various features of novelty which characterize the disclosure, are pointed out with particularity in the claims annexed hereto and forming a part of this disclosure.

BRIEF DESCRIPTION OF THE DRAWINGS

Various embodiments of the presently disclosed surgical fastener applying apparatus will be described herein with reference to the accompanying drawing figures wherein:

FIG. 13 is a top plan view of the surgical fastener applying apparatus with a firing lever in the proximal-most position;

FIG. 14 is a cross-sectional view taken along section line 14-14 of FIG. 13;

FIG. 15 is an enlarged view of the indicated area of detail of FIG. 14;

FIG. 16 is an enlarged view of the indicated area of detail of FIG. 14;

FIG. 17 is a plan view similar to FIG. 13, which shows the firing lever advanced distally a short distance;

FIG. 18 is a cross-sectional view taken along section line 18-18 of FIG. 17;

FIG. 19 is an enlarged view of the indicated area of detail of FIG. 18;

FIG. 20 is an enlarged view of the indicated area of detail of FIG. 18;

FIG. 34 is a cross-sectional view of the surgical fastener applying apparatus of FIGS. 21-40, in a pre-fired condition, taken along the longitudinal center line thereof;

FIG. 35 is an enlarged view of the indicated area of detail of FIG. 34;

FIG. 36 is an enlarged view of the indicated area of detail of FIG. 34;

FIG. 37 is a cross-sectional view of the surgical fastener applying apparatus of FIGS. 21-40, in a post-fired condition, taken along the longitudinal center line thereof;

FIG. 38 is an enlarged view of the indicated area of detail of FIG. 37;

FIG. 39 is an enlarged view of the indicated area of detail of FIG. 37;

FIG. 54 is a distal side perspective view of the surgical fastener applying apparatus of FIG. 50 with the contoured handles removed therefrom;

FIG. 55 is a rear perspective view of the surgical fastener applying apparatus of FIG. 54;

FIG. 57 is a perspective view, with parts separated, of the anvil half-section side of the surgical fastener applying apparatus of FIG. 50;

FIG. 58 is an enlarged perspective view of an eccentric cam in accordance with the present disclosure;

FIG. 58A is a side elevational view of the eccentric cam as shown in FIG. 58;

FIG. 58B is a rear elevational view of the eccentric cam as shown in FIG. 58;

FIG. 59 is a perspective view of the anvil half-section side of the surgical fastener applying apparatus of FIG. 50, as seen from the bottom;

FIG. 60 is an enlarged view of the indicated area of FIG. 59;

FIG. 61 is an enlarged view of the indicated area of FIG. 59;

FIG. 62 is a side elevational view of the anvil half-section detailing the eccentric cam of FIG. 58;

FIG. 63 is a cross-sectional view, taken along the longitudinal axis, of the anvil half-section as seen in FIG. 62;

FIG. 64 is a side elevational view of the anvil and cartridge receiving half-sections coupled to one another detailing the operation of the eccentric cam of FIG. 58;

FIG. 65 is a side-elevational view of the anvil and cartridge receiving half-sections coupled to one another further detailing the operation of the eccentric cam of FIG. 58;

FIG. 69 is a perspective view of a firing slide, as seen from the bottom, of the surgical fastener applying apparatus of FIG. 50;

FIG. 70 is a perspective view, with parts separated, of the firing slide of FIG. 69;

FIG. 71 is a perspective view of a proximal end of the center bar of the firing slide of FIG. 69;

FIG. 72 is a top perspective view of a proximal end of the firing slide of FIG. 69;

FIG. 73 is a perspective view of a slide block of the firing slide of FIG. 69;

FIG. 74 is a bottom perspective view of a firing lever of the firing slide of FIG. 69;

FIG. 75 is across-sectional view of the proximal end of the firing slide of FIG. 69;

FIG. 76 is a perspective view of the lock out mechanism of the surgical fastener applying apparatus of FIG. 50;

FIG. 77 is a perspective view, with parts separated, of the cartridge receiving half-section frame of the surgical fastener applying apparatus of FIG. 50;

FIG. 78 is a bottom perspective view of the cartridge receiving half-section frame of FIG. 77;

FIG. 79 is a perspective view of a cartridge receiving half-section side of the surgical fastener applying apparatus of FIG. 50;

FIG. 80 is an enlarged view of the indicated area of detail of FIG. 79;

FIG. 81 is an enlarged view of the indicated area of detail of FIG. 79;

FIG. 83 is a perspective view of a cartridge receiving half-section clamp lever of the surgical fastener applying apparatus of FIG. 50;

FIG. 84 is another perspective view of the cartridge receiving half-section clamp lever of FIG. 50;

FIG. 90 is an enlarged view of the indicated area of detail of FIG. 87;

FIG. 91 is an enlarged side elevational view of the proximal end of anvil half-section being coupled to the cartridge receiving half-section;

FIG. 93 is an enlarged view of the indicated area of detail of FIG. 92;

FIG. 94 is an enlarged view of the indicated area of detail of FIG. 92;

FIG. 95 is a top plan view of the surgical fastener applying apparatus of FIG. 50, in a post-firing condition;

FIG. 96 is a cross-sectional view, taken along the longitudinal axis, of the surgical fastening applying apparatus of FIG. 50, in the post-firing condition;

FIG. 99 is a perspective view of the surgical fastener applying apparatus of FIG. 50, in an open post-firing condition;

FIG. 100 is an enlarged view of the indicated area of detail of FIG. 99;

DETAILED DESCRIPTION OF PREFERRED EMBODIMENTS

Figure 1:
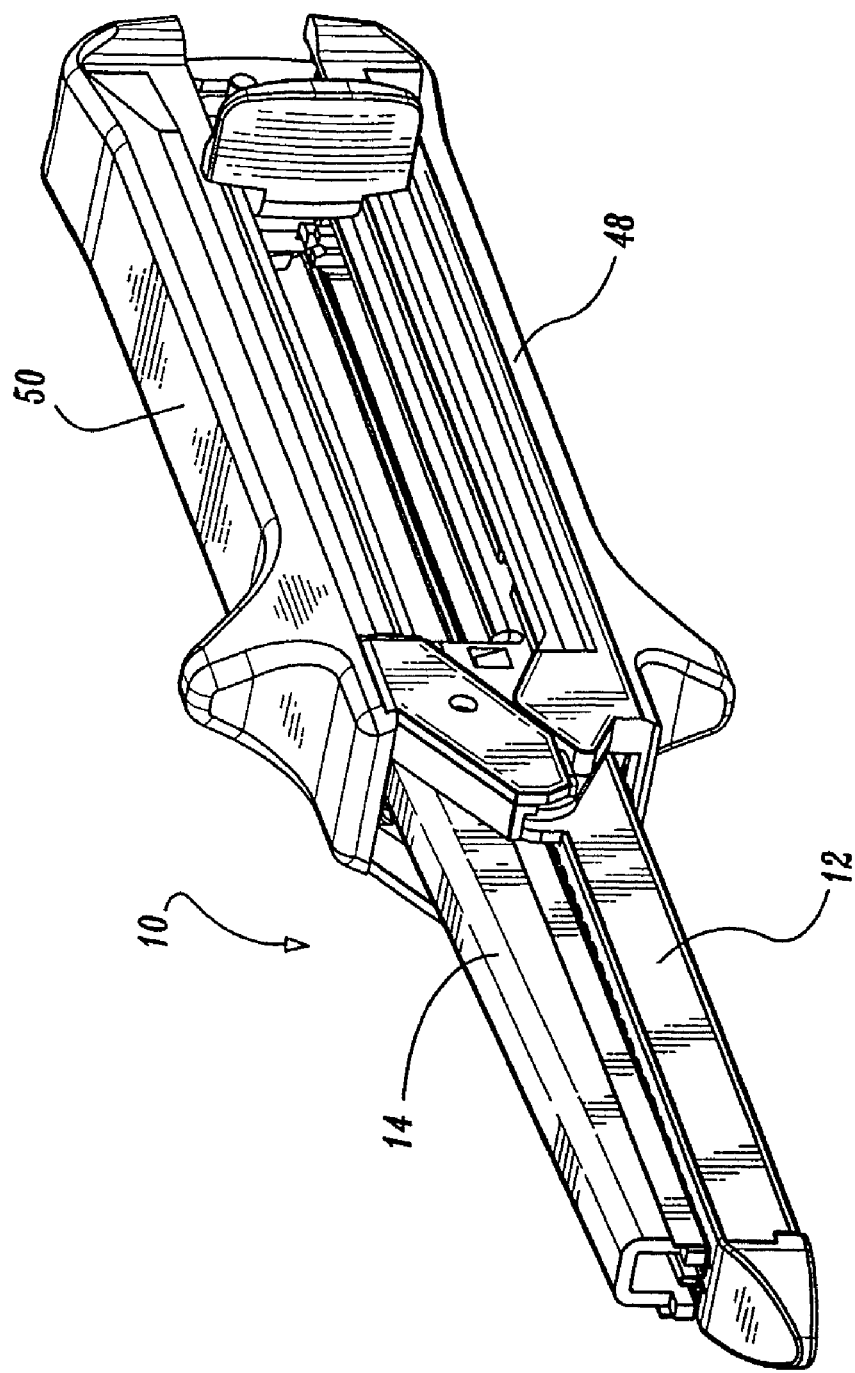
FIG. 1 is a perspective view of one embodiment of a surgical fastener applying apparatus constructed in accordance with the present disclosure.

Preferred embodiments of surgical fastener applying apparatus in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring initially to FIGS. 1-22, an illustrative embodiment of the presently disclosed surgical fastener applying apparatus is illustrated therein and designated generally as surgical stapler 10. Surgical stapler 10 is particularly adapted to apply a plurality of adjacent rows of staples to body tissue clamped in between the instrument's two principle sections, a cartridge receiving half-section 12 and an anvil half-section 14. Typical applications of the presently disclosed surgical fastener apparatus are, for example, creating a hemostatic seal in general, thoracic, and urologic surgery for resection, transection and creation of anastomoses. Specific tissue structures in which the instrument may be used are, for example, the stomach, the large and small bowels, lungs and the esophagus.

Figure 2:
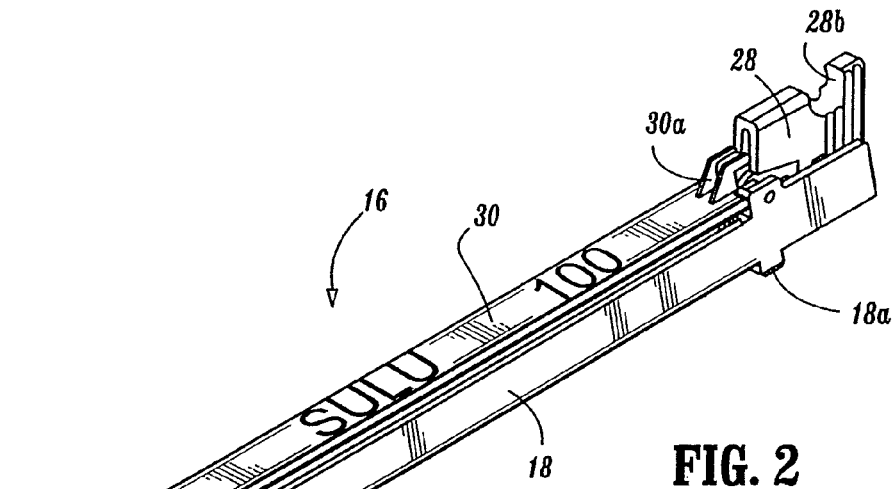
FIG. 2 is a perspective view of a disposable staple cartridge assembly for the surgical fastener applying apparatus shown in FIG. 1.
Figure 3:
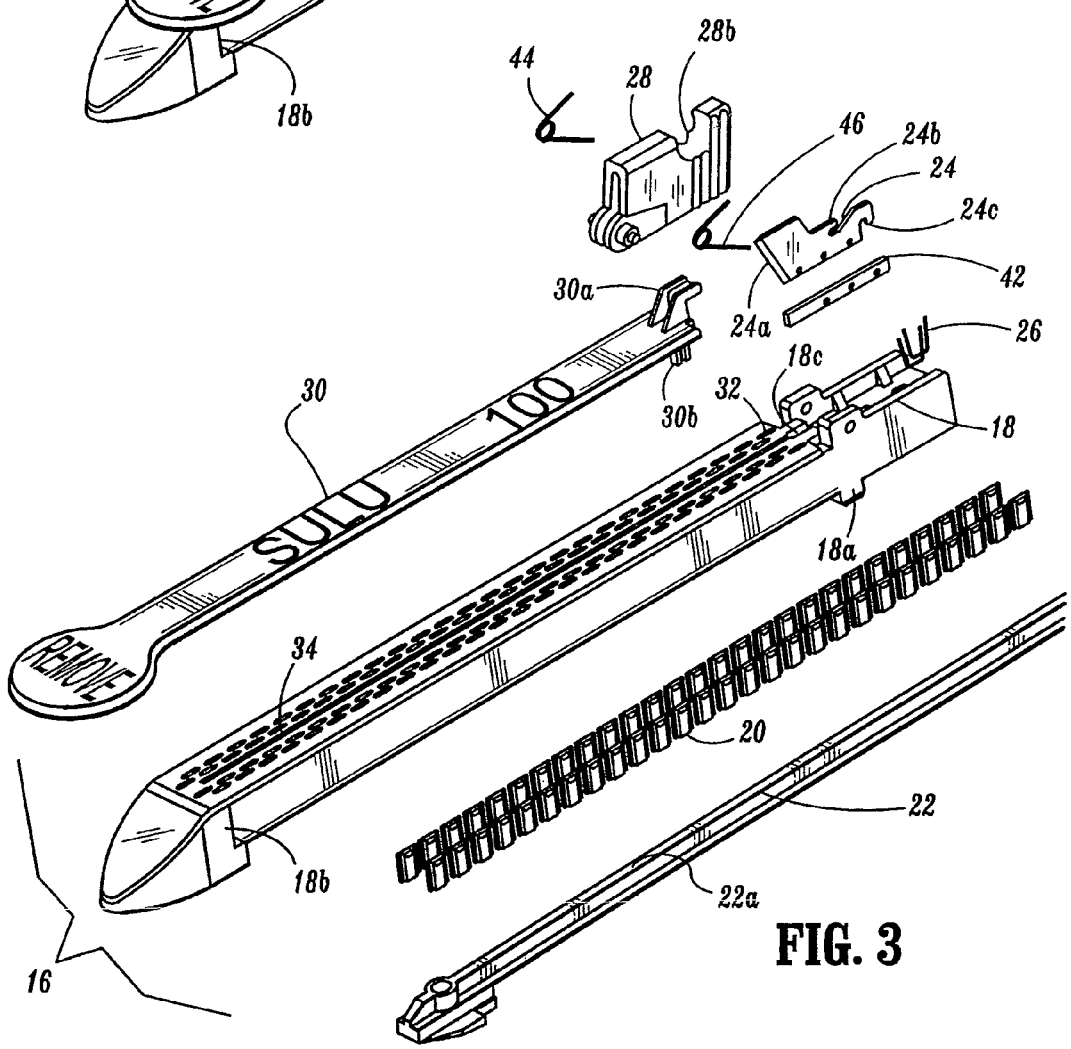
FIG. 3 is a perspective view, with parts separated, of the disposable staple cartridge assembly of FIG. 2.
Figure 4:
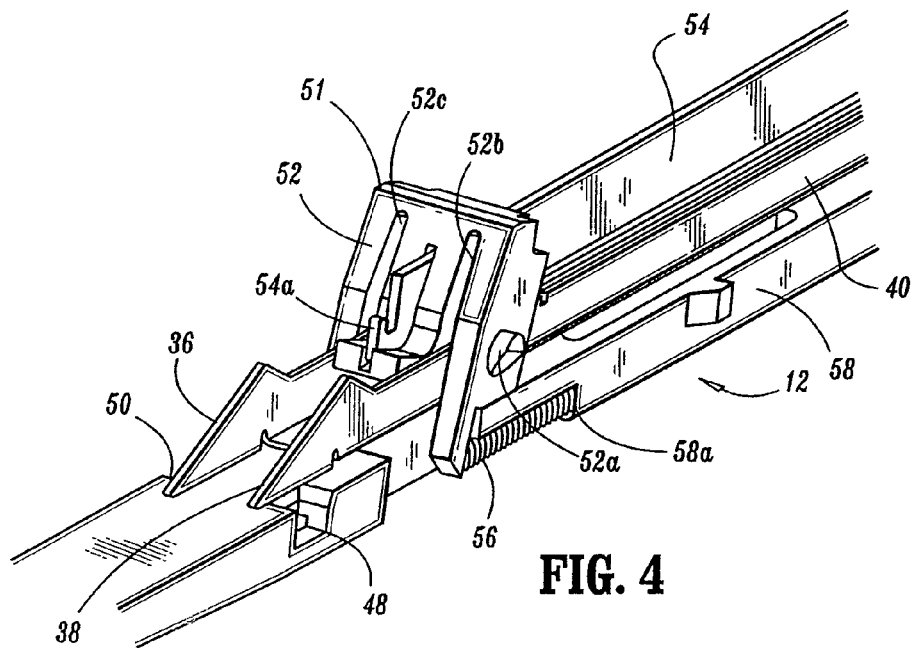
FIG. 4 is an enlarged left distal perspective view of an embodiment of a staple cartridge loading and lockout mechanism.

Turning now to FIGS. 2 and 3, surgical stapler 10 is designed for use with a disposable staple cartridge assembly 16, such as, for example, a single use disposable loading unit ("SULU"). Cartridge assembly 16 includes a cartridge body 18, a plurality of staple pushers 20, a bottom cover 22, a knife 24 having an angled sharpened leading edge 24a, a plurality of staples 26, a pivotably mounted safety lockout 28 and a removable shipping wedge 30. As with known staple cartridge designs, cartridge body 18 has a plurality of rows of staple retaining slots 32 formed therein. Surgical stapler 10 may be manufactured and assembled in different sizes to receive different size cartridge assemblies 16. For example, surgical stapler 10 can be made in different sizes to accept cartridge assemblies 16 having staple line lengths of approximately 60 mm, 80 mm, and 100 mm.

Alternatively, cartridge assemblies 16 may be adapted such that one common surgical stapler 10 will accept multiple different staple count cartridge assemblies. For example, cartridge assemblies 16 may be configured such that each different staple count cartridge assembly shares a common size cartridge body 18 to facilitate mounting on surgical stapler 10.

In the illustrated embodiment, there are two staggered rows of slots 32 formed on either side of a linear slotted track 34 which guides knife 24 during its longitudinal movement. A single staple 26 is positioned in each of slots 32. The staple rows preferably extend a distance distally beyond the distal end of knife track 34 to facilitate staple formation beyond the stroke length of knife 24.

Staple pushers 20 are aligned one each with slots 32 such that a single staple pusher member 20 is positioned under a respective staple 26 which is retained within slot 32. Staple pushers 20 are formed such that they are attached to each other in groups of two offset oriented pusher pairs and have an actuating surface (not shown) connecting each pair of pusher members 20.

Staple pushers 20 are arranged in two series, one on each side of slotted track 34, such that the actuating surfaces of each series of staple pushers 20 forms a line centered between the staggered rows of staples 26. The actuating surfaces act as cam followers and interact with a pair of staggered camming surfaces 36, 38 extending from a generally U-shaped cam bar 40 (see FIGS. 4 and 5) to expel the pairs of staples 26 on each side of knife track 34. As illustrated, camming surfaces 36, 38 form a single angle relative to horizontal. In certain applications, for example, with staples having an unformed leg height of about 4.5 mm, camming surfaces 36, 38 may be formed of a plurality of angles to facilitate optimal staple deformation with a given firing force, as cam bar 40 is moved distally. This sequence is repeated until the distal movement of cam bar 40 is either stopped intentionally by the user to form less than all of staples 26 or until all of staples 26 are expelled from cartridge assembly 16.

Bottom cover 22 partially encloses the bottom of a channel formed by the upper surface of the channel bottom wall and the side walls of cartridge body 18. A longitudinal ridge 22a is formed on an upper surface of bottom cover 22 and serves as a bearing surface for knife bearing channel 42, which is secured to the bottom edge of knife 24, as it travels in knife track 34. A pair of slots are formed, one on either side of longitudinal ridge 22a, the outer limit of each slot being defined by the outer side wall of cartridge body 18 on a respective side of ridge 22a. These slots facilitate reciprocating longitudinal movement of the extensions of camming surfaces 36, 38 of generally U-shaped cam bar 40. Knife bearing channel member 42 which is preferably wider than knife track 34, is secured to the bottom surface of the knife 24 such that knife bearing channel member 42 rides between knife track 34 and longitudinal ridge 22a of bottom cover 22. In this manner, knife 24 is prevented from undergoing substantial vertical movement during longitudinal translation in knife track 34.

Safety lockout 28 is pivotably disposed on the upper proximal end of cartridge body 18 and is movable from a locked orientation to an unlocked orientation. Preferably, safety lockout 28 is biased away from the unlocked orientation towards an orientation substantially perpendicular to the longitudinal axis of cartridge body 18. Any suitable bias member may be utilized such as, for example, springs 44, 46. To overcome the bias towards the perpendicular orientation, safety lockout 28 includes a transverse horizontal surface 28a, preferably a projection (see FIG. 15) formed on the underside thereof which engages a member, preferably a projection or a hook 24b formed on the upper edge surface of knife 24. This cooperative engagement serves to retain safety lockout 28 in the locked orientation wherein safety lockout 28 covers knife 24.

When surgical stapler 10 has been unclamped, as will be described in greater detail further herein, after either partial or complete firing of surgical stapler 10, safety lockout 28 is biased to the perpendicular orientation (see FIGS. 10 and 11), extending upwardly away from cartridge receiving half-section 12. In this manner, safety lockout 28 prevents surgical stapler 10 from being re-clamped until the partial or completely fired cartridge assembly 16 is removed and replaced with a new cartridge assembly 16. Safety lockout 28 also provides a cut-out grasping surface 28b with which cartridge assembly 16 may readily be removed from surgical stapler 10.

As previously noted, shipping wedge 30 is removably attachable to cartridge body 18. When installed on cartridge assembly 16, shipping wedge 30 covers the entire surface area of staple rows 26 and knife track 34. Additionally, shipping wedge 30 includes an abutment 30a extending upwardly and proximally from an upper proximal surface thereof. Abutment 30a in cooperation with safety lockout 28 covers sharpened distal edge 24a of knife 24. This feature prevents knife 24 from being exposed to the user during handling of cartridge assembly 16. Additionally, abutment 30a prevents premature pivotal movement of safety lockout 28 from the locked orientation. Thus, even if cartridge assembly 16 is properly loaded on surgical stapler 10, staples 26 cannot be fired until shipping wedge 30 is first removed.

Shipping wedge 30 also includes a post 30b extending downwardly from the underside thereof near the proximal end. Post 30b fits into a complementary shaped opening 18c formed in cartridge body 18 at the proximal end of knife track 34. With shipping wedge 30 in place, post 30b blocks potential distal movement of knife 26. In an alternative embodiment, cartridge assemblies 16 may also be provided without a knife in applications where it is desirable to perform stapling without transection. In such an embodiment, knife 26 is replaced with a blank element to substitute for the knife to interact with safety lockout 28.

Cartridge body 18 is provided with several shaped surfaces to facilitate mounting and alignment of cartridge assembly 16 with respect to cartridge receiving half-section 12 of surgical stapler 10. Such alignment facilitating surfaces may be formed at any suitable location on the various components of cartridge body 18 to correspond with complementary surfaces on cartridge receiving half-section 12. In the illustrated embodiment, locating/alignment feature surfaces 18a are formed extending downwardly on either side of cartridge assembly 16 near the proximal end thereof and molded surfaces 18b are formed on either side of cartridge body 18 near the distal end thereof. When cartridge assembly 16 is properly installed on surgical stapler 10, surfaces 18a seat in a pair of notches 48, 50 (see FIGS. 4, 5, 6 and 8) formed in cartridge receiving half-section 12.

Referring to FIGS. 4-9, a loading and lockout mechanism 50 for cartridge assembly 16 will now be described in detail. In these figures, a channel frame 12a (see FIG. 12) of cartridge receiving half-section 12 is not shown so that loading and lockout mechanism 50 can be illustrated more clearly. Loading and lockout mechanism 50 facilitates loading of cartridge assembly 16 and prevents firing of surgical stapler 10 until cartridge assembly 16 is properly loaded or assembled on cartridge receiving half-section 12 and surgical stapler 10 is properly clamped shut. Loading and lockout mechanism 50 includes a rocker 52 which is pivotably mounted to channel frame 12a (see FIG. 12) of cartridge receiving half-section 12 by way of transversely extending post portions 52a seating in openings formed through the sidewalls of channel frame 12a. Post portions 52a are provided with angled downwardly oriented surfaces to facilitate assembly of rocker 52 with channel frame 12a. Rocker 52 is preferably a molded plastic component and is provided with three slots, namely open bottomed slots 52b, 52c to permit longitudinal movement of cam bar 40 and a closed slot 52d to permit passage of a center bar 54 (see FIG. 4) therethrough.

Figure 5:
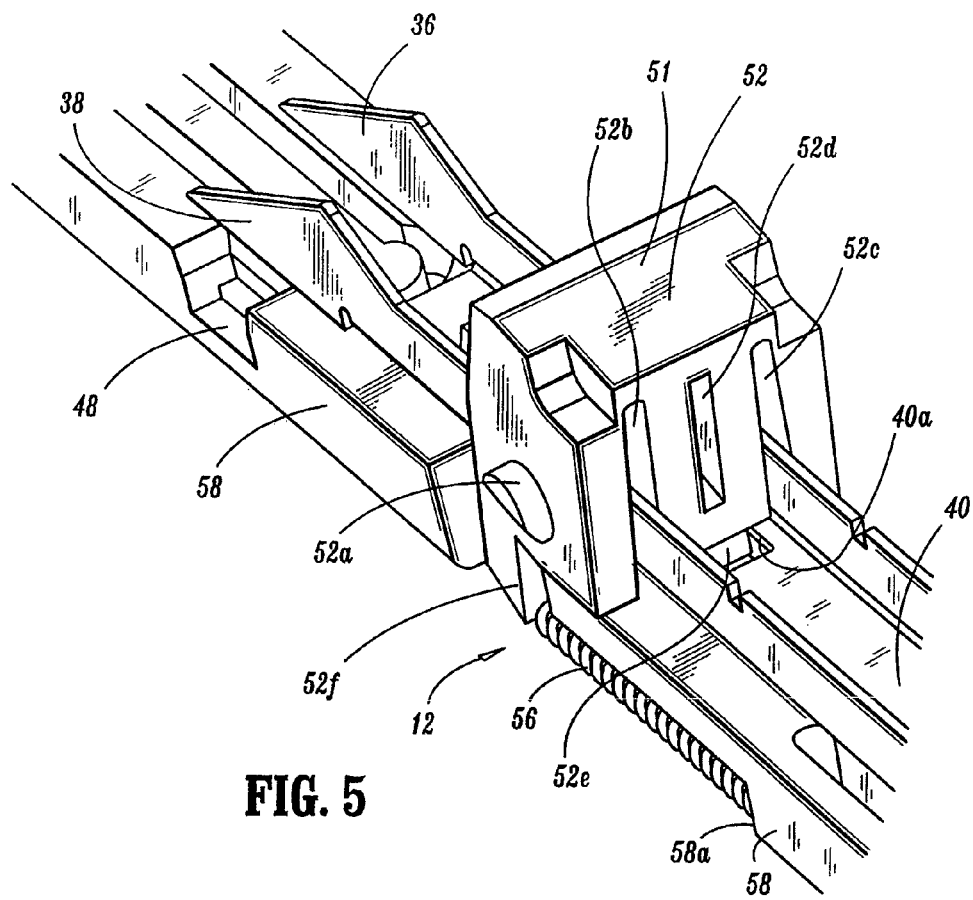
FIG. 5 is an enlarged right side proximal perspective view of the loading and lockout mechanism of FIG. 4.
Figure 6:
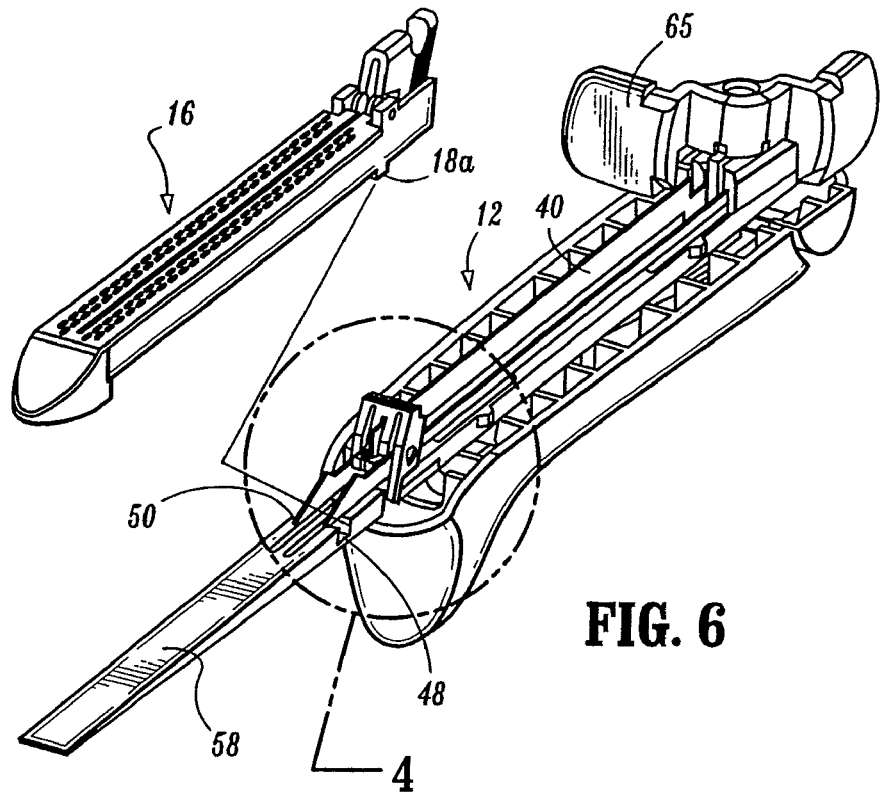
FIG. 6 is a perspective view, with parts separated, showing coupling of the staple cartridge assembly of FIG. 2 on a cartridge receiving half-section of the surgical fastener applying apparatus of FIG. 1.
Figure 7:
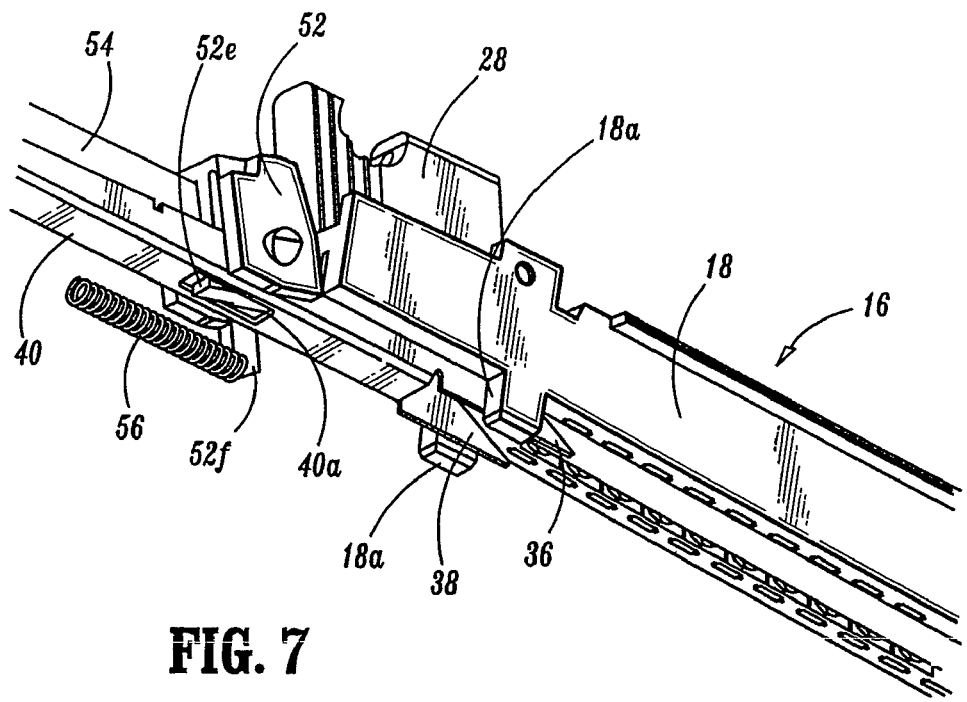
FIG. 7 is an enlarged perspective bottom view of the loading and lockout mechanism with the staple cartridge assembly of FIG. 2 operatively coupled thereto.

As best shown in FIGS. 5 and 7, rocker 52 is further provided with a downwardly extending blocking surface 52e which is in vertical alignment with an opening 40a formed through the bottom surface of cam bar channel 40 when cam bar channel 40 is in its proximal-most position. Rocker 52 is biased, by way of a spring 56 which is disposed between downwardly extending leg 52f and an end wall 58a of a beam member 58, toward a locked-out vertical or upstanding position wherein blocking surface 52e extends through opening 40a. In this manner, cam bar 40 is prevented from distal longitudinal movement. In versions of surgical stapler 10 using shorter cartridge assemblies 16, beam member 58 may be eliminated.

Figure 8:
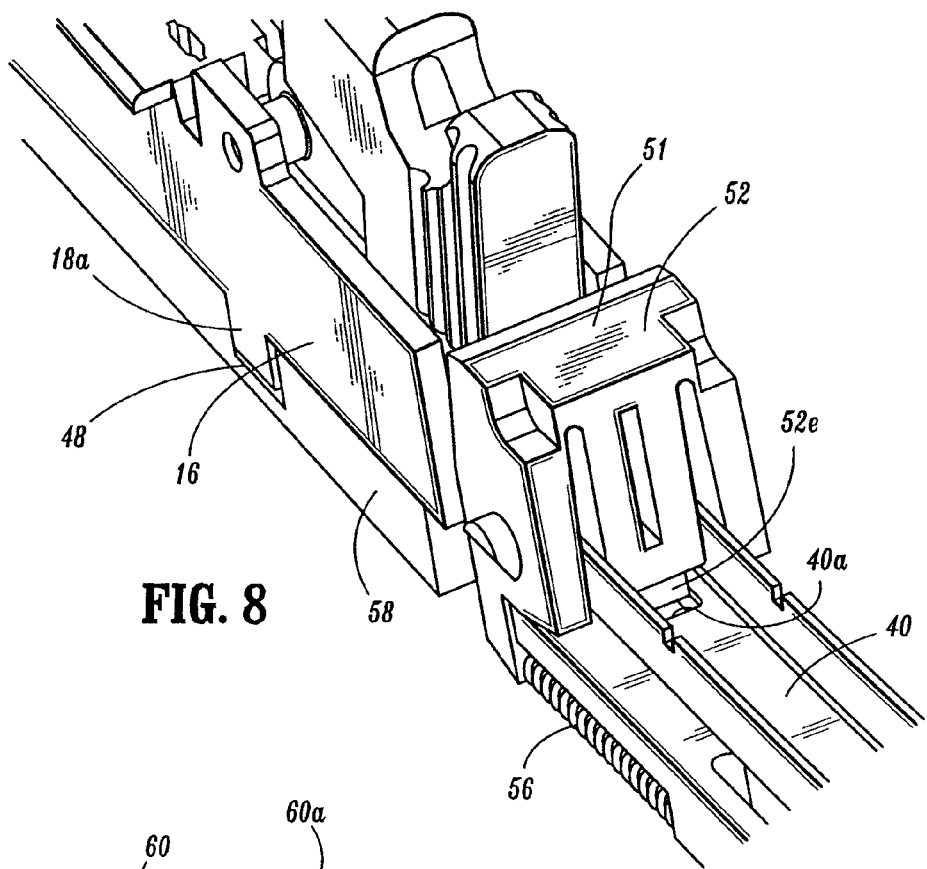
FIG. 8 is an enlarged perspective view similar to FIG. 5, with the staple cartridge assembly of FIG. 2 in place.
Figure 9:
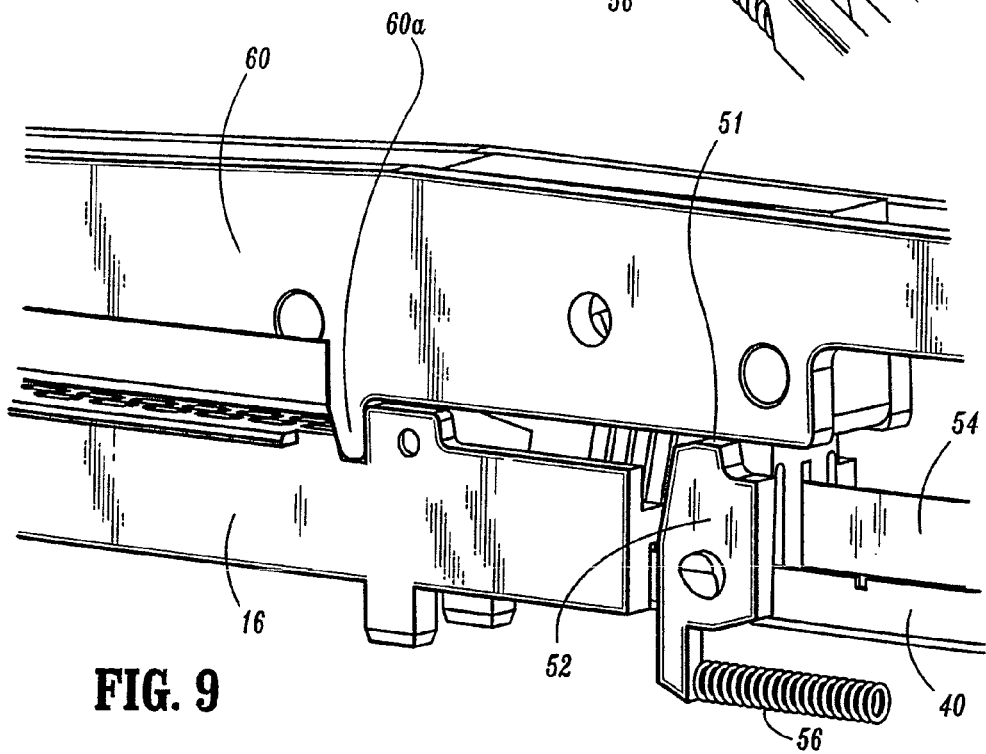
FIG. 9 is an enlarged side perspective view which shows the relative positioning of the loading and lockout mechanism with the staple cartridge assembly of FIG. 2 installed and with an anvil half-section in place in a clamped condition.

Upon loading of cartridge assembly 16 on cartridge receiving half-section 12, as shown in FIG. 8, the spring bias of spring 56 maintains rocker 52 in the locked-out position. It is only when anvil half-section 14 is joined with cartridge receiving half-section 12 and the half-sections clamped together, as seen in FIG. 9, thereby causing downwardly extending leg portions 60a formed on either side of anvil half-section channel member 60 to bias against cartridge assembly 16, that rocker 52 is urged to rotate by the camming action of proximal end surface of cartridge assembly 16 against the distal end surface 51 of rocker 52. In this manner, blocking surface 52e is moved out of (i.e., pivoted out of) longitudinal alignment with opening 40a of cam bar channel 40 thereby permitting a distal longitudinal movement of cam bar channel 40.

Figure 11:
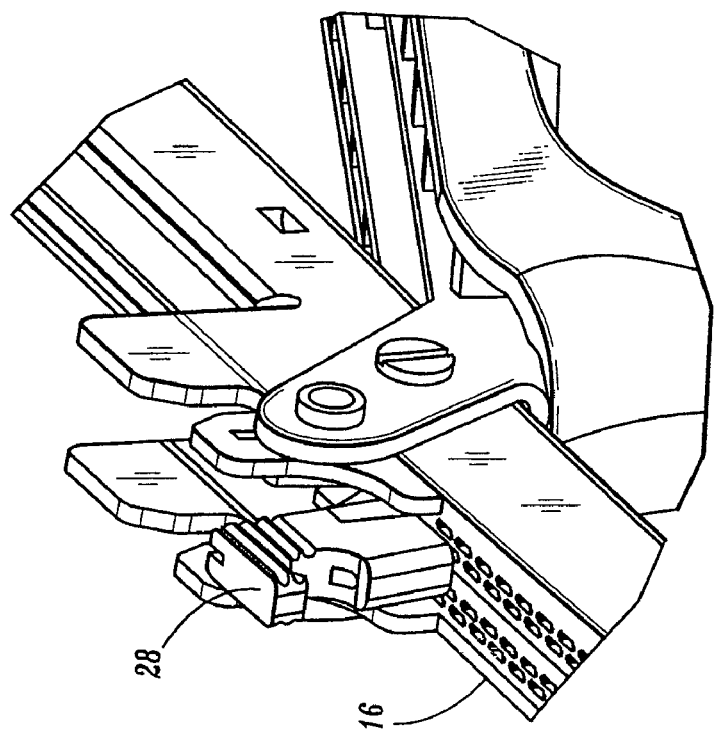
FIG. 11 is an enlarged view of the indicated area of detail of FIG. 10.
Figure 10:
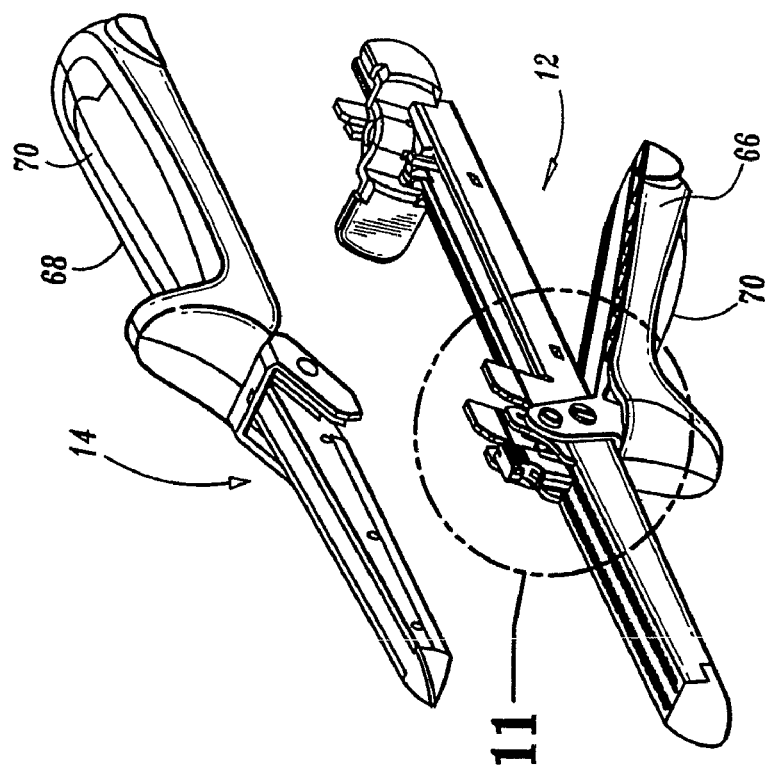
FIG. 10 is a perspective view which shows the surgical fastener applying apparatus of FIG. 1 after partial or complete firing and in an unclamped condition with a staple cartridge safety lockout in a locked out position.

Referring to FIGS. 10 and 11, once surgical stapler 10 has been at least partially fired, if the instrument is opened, safety lockout 28 of cartridge assembly 16 automatically moves to the perpendicular orientation due to the spring bias mounting thereof. With safety lockout 28 in this orientation, surgical stapler 10 cannot be re-clamped. Thus, if the user desires to apply further staples, partially or completely fired cartridge assembly 16 must first be removed and replaced with a non-fired cartridge assembly 16.

Figure 12:
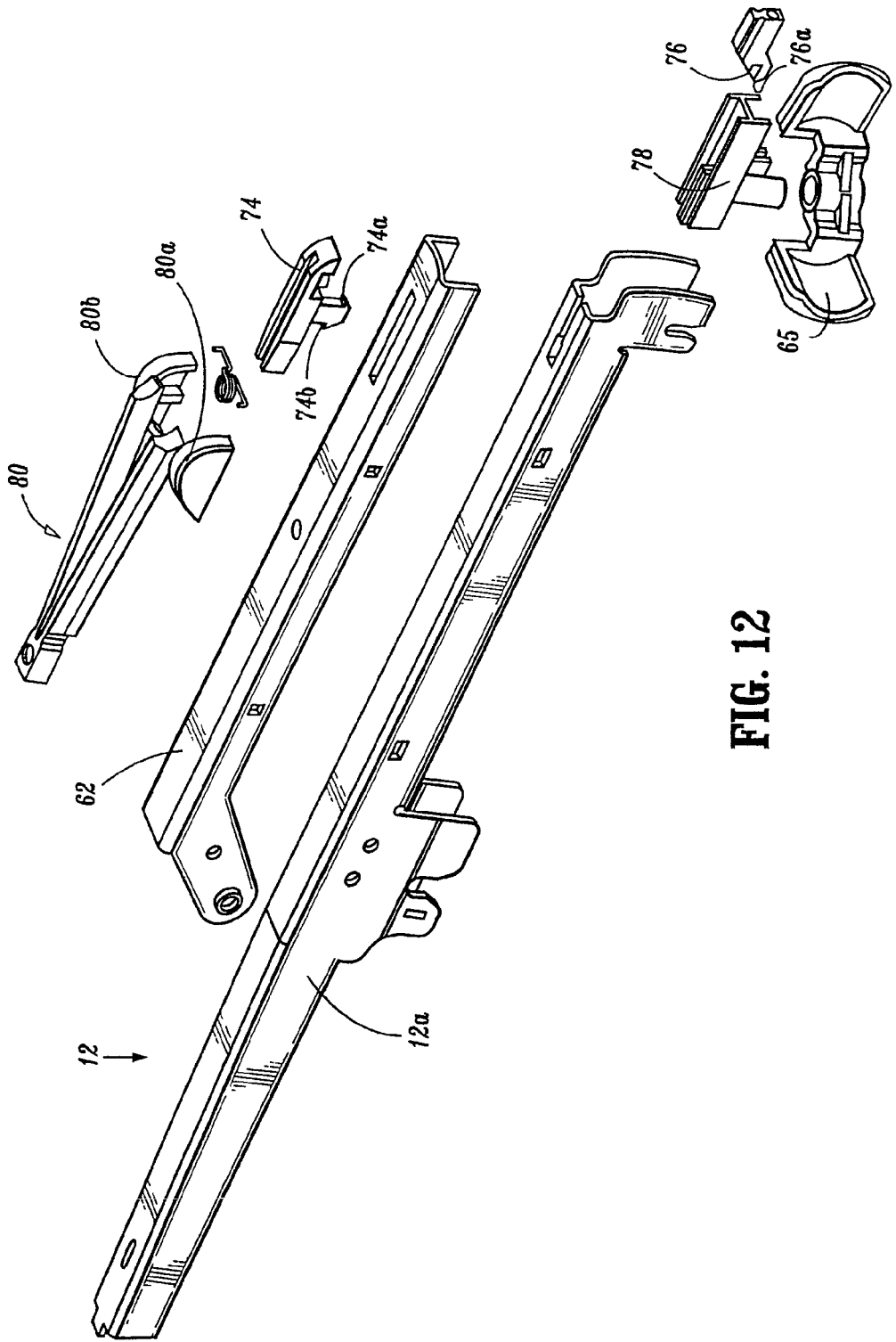
FIG. 12 is a perspective view with parts separated which shows the structural relationship of the various components of an embodiment of a clamp lever lockout and safety interlock mechanism of the present disclosure.
Figure 21:
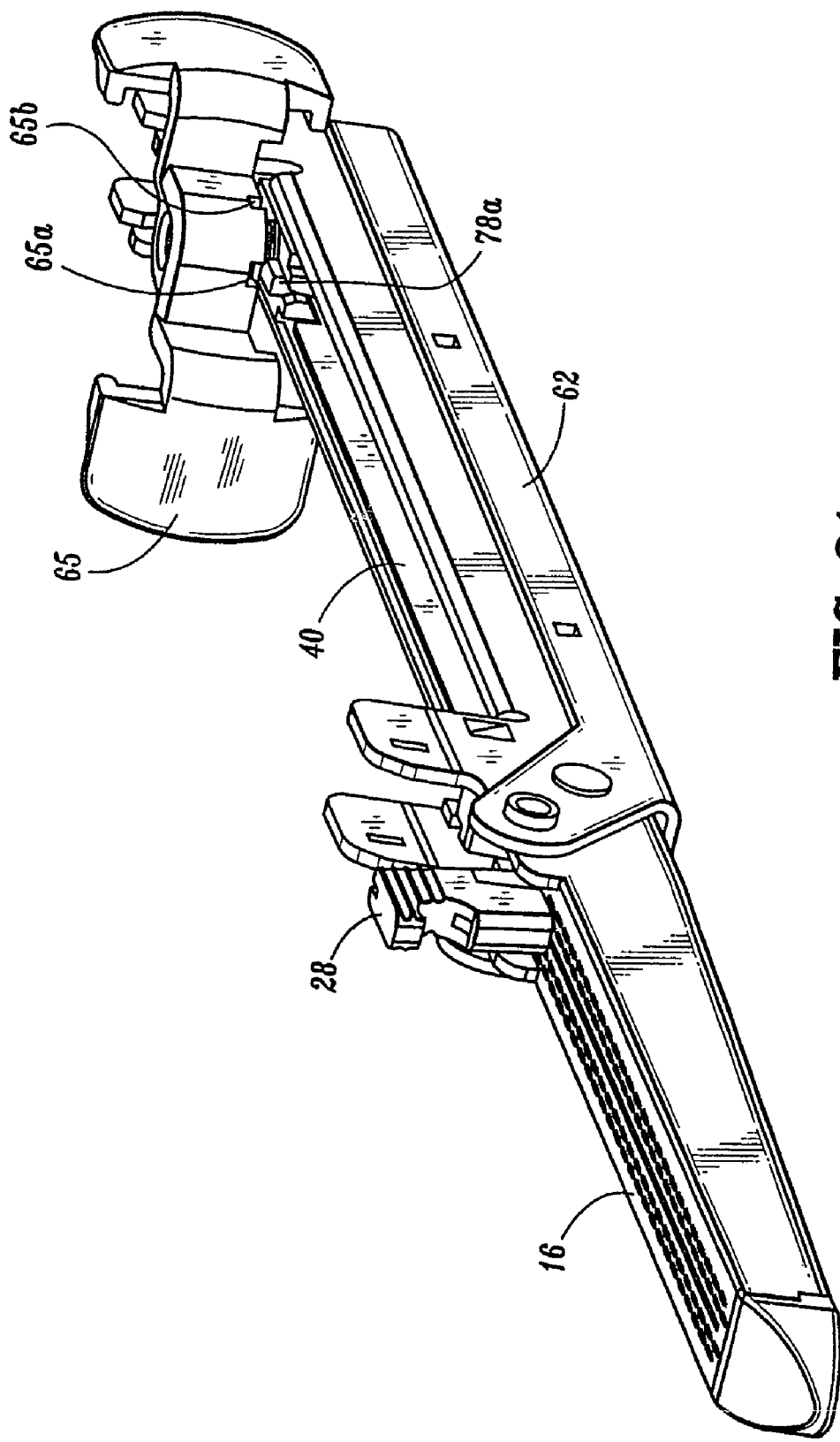
FIG. 21 is a perspective view of the cartridge receiving half-section of the surgical fastener applying apparatus of FIG. 1.

As will be described in greater detail below and as seen in FIGS. 12 and 21, surgical stapler 10 is provided with a pivotably mounted firing lever 65. Pivotally mounted firing lever 65 provides the user with the ability to fire surgical stapler 10 from either the left or right side.

Referring to FIG. 12, surgical stapler 10 is provided with a clamping lever 62 pivotably mounted to cartridge receiving half-section 12. An ergonomic contoured handle 66 (see FIG. 10) is secured to clamping lever 62 to provide the user with a convenient gripping handle. To further enhance the gripping of surgical stapler 10 by the user, a friction enhancing insert 70 (see FIG. 10) is secured to handles 66 and 68. Insert 70 may be formed of any suitable friction enhancing material, for example, rubber. As seen in FIG. 10, anvil half-section 14 is provided with an ergonomic contoured handle 68 secured to anvil half-section channel member 60 to provide the user with a convenient gripping handle. Half-sections 12 and 14 are preferably configured and dimensioned to provide the user with the ability to reach around both halves and comfortably close surgical stapler 10 with a one-handed operation in order to approximate the half-sections and clamp the captured tissue.

Referring also to FIGS. 14-16 and 18-20, a clamp latch and safety interlock mechanism 70 is provided at the proximal end of surgical stapler 10. Clamp latch and safety interlock mechanism 70 serves to retain clamp lever 62 in a clamped orientation as well as to provide a safety interlock which prevents opening of clamp lever 62 once firing lever 65 is moved distally. Cartridge receiving half-section 12 is provided with a clamp latch and safety interlock mechanism 70 which works to latch clamp lever 62 in a clamped configuration upon squeezing clamp lever 62 to the closed position. While a clamp lever 62 is shown and described as being pivotably mounted to cartridge receiving half-section 12, it is envisioned that a clamp lever can be pivotably mounted to anvil half-section 14 or a clamp lever can be pivotably mounted to each of cartridge receiving half-section 12 and anvil half-section 14. Accordingly, the following description of the various components which make up the assembly will be directed to that for the cartridge receiving half-section 12 as shown in FIG. 12.

Clamp latch and safety interlock mechanism 70 includes a distal clamp lever latch 74 and a proximal interlock latch 76 which is spring biased distally toward a latched position. As seen in FIG. 16, when surgical stapler 10 is in the clamped configuration with firing lever 65 in the proximal-most position, a firing slide block 78 biases latch 76 proximally to overcome the distal spring bias to position ledge 76a of latch 76 out of lateral alignment with proximal ledge 74a formed on latch 74 thereby positioning and maintaining latch 76 in an unlatched position. In this position, the user may unclamp clamp lever 62 by squeezing spring biased finger pad portions 80a, 80b of latch handle release member 80 (see FIG. 12) which urges latch 74 proximally such that distal ledge 74b is moved out of lateral alignment with the blocking structure formed on cartridge receiving half-section 12a (not shown).

Once firing lever 65 is moved distally to begin the firing sequence of surgical stapler 10, as shown in FIGS. 17, 18 and 20, slide block 78 is also moved distally thereby removing the biasing force which overcame the distal spring bias of latch 76. Thus, ledge 76a moves into lateral alignment with ledge 74a of latch 74 thereby preventing clamp lever 62 from being opened until firing lever 65 is once again moved to the proximal-most position. The instrument is thereby prevented from opening during the firing stroke.

Upon initial distal movement, firing lever 65 becomes locked-out from pivotal movement by way of firing lever 65 being caromed upwardly to overcome an upward spring bias, as shown in the operationally progressive views of FIGS. 16 and 20. In particular, as best shown in FIG. 21, recessed notches 65a, 65b are formed as keyways which engage a key 78a formed on slide block 78, respectively, depending upon which side of firing lever 65 is employed to actuate firing. Firing lever 65 can be returned to the proximal-most position at any time during the firing stroke. Firing lever 65 must be returned to the proximal-most position before the lever can be released and the instrument unclamped. As described previously, if the instrument is opened after firing, either partially or completely, safety lockout 28 on cartridge assembly 16 is configured to prevent the user from re-clamping the instrument.

Figure 22:
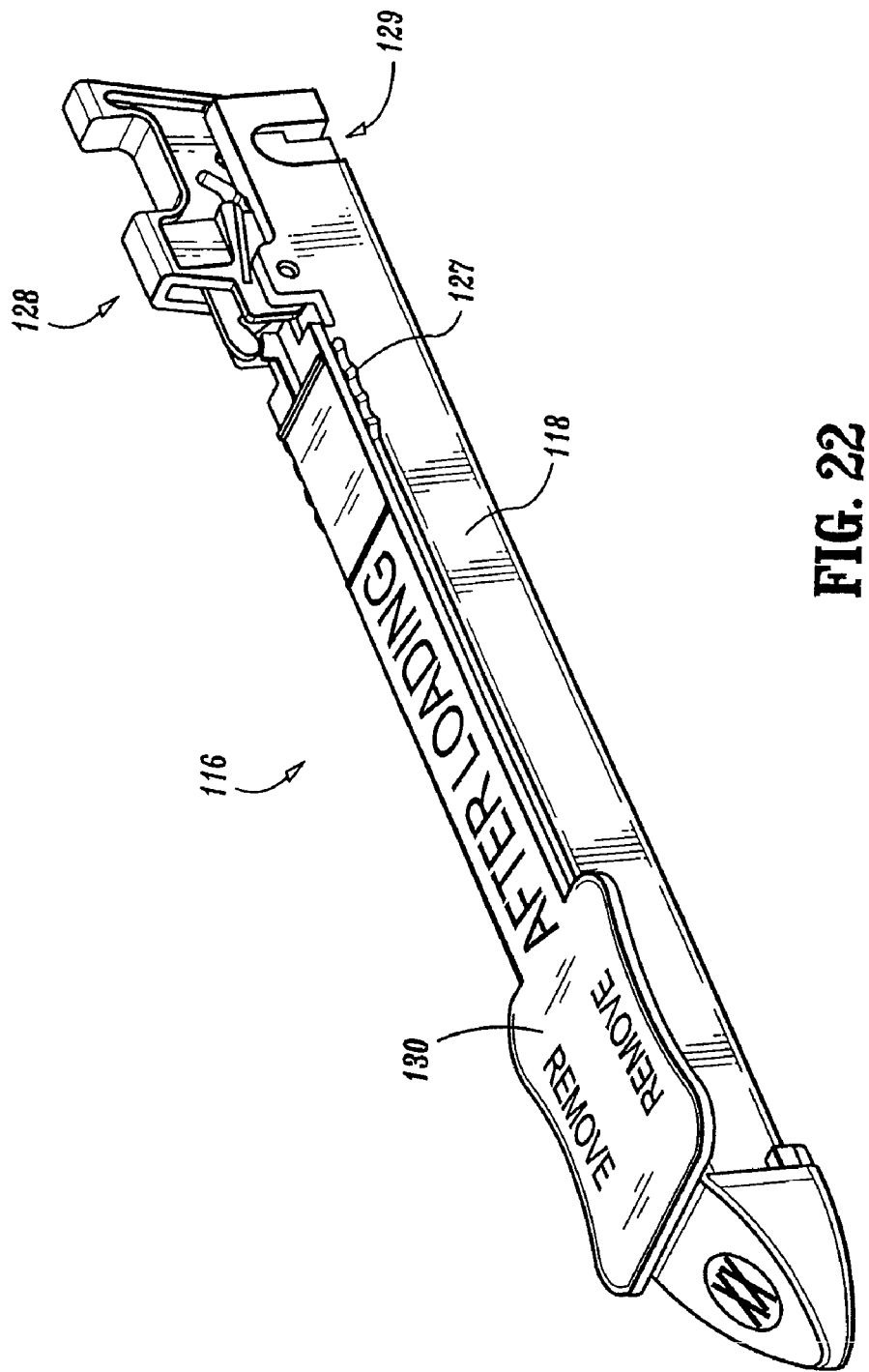
FIG. 22 is a perspective view of a disposable staple cartridge assembly according to an alternative embodiment of the present disclosure.
Figure 23:
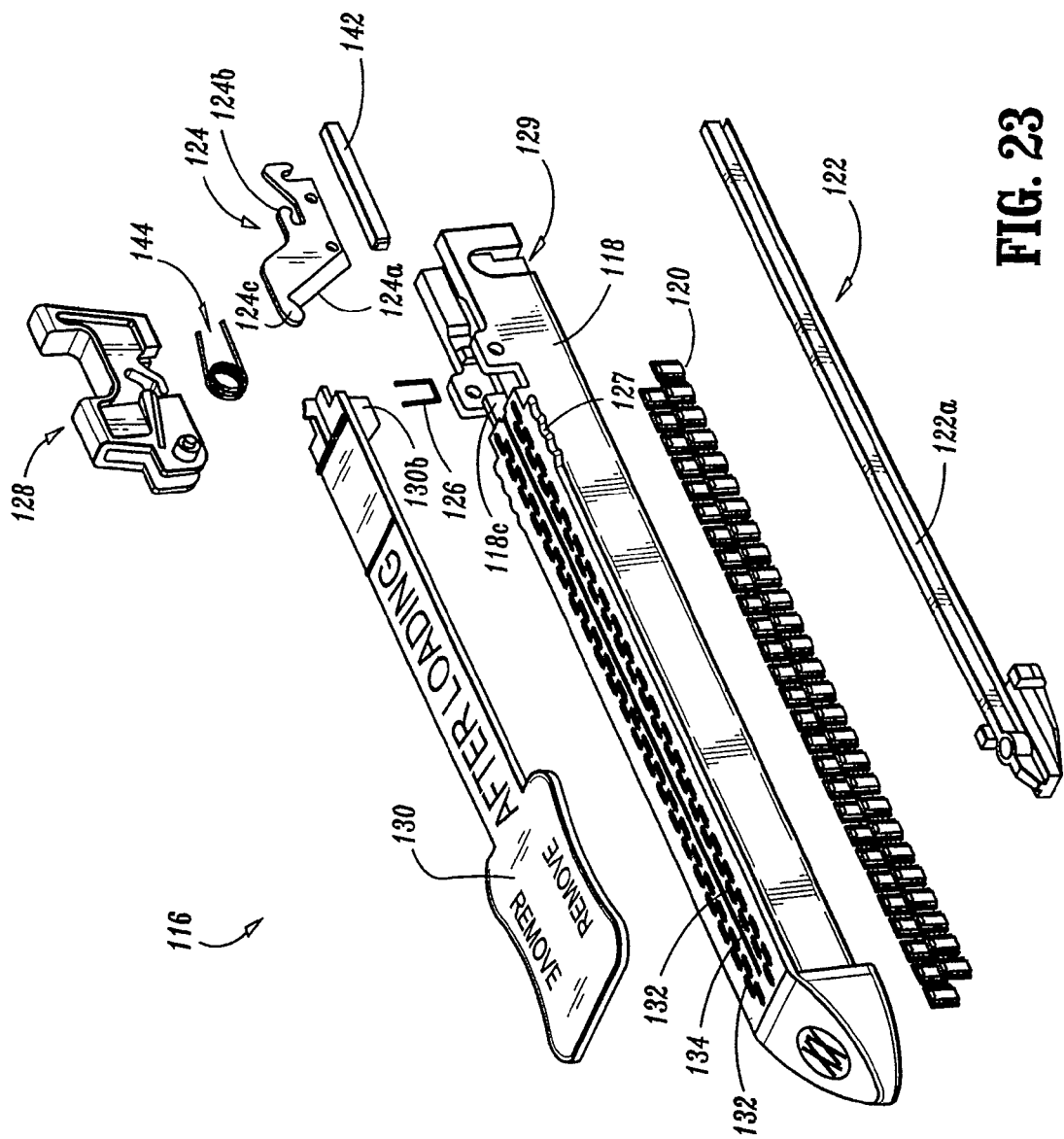
FIG. 23 is a perspective view, with parts separated, of the disposable staple cartridge assembly of FIG. 22.
Figure 24:
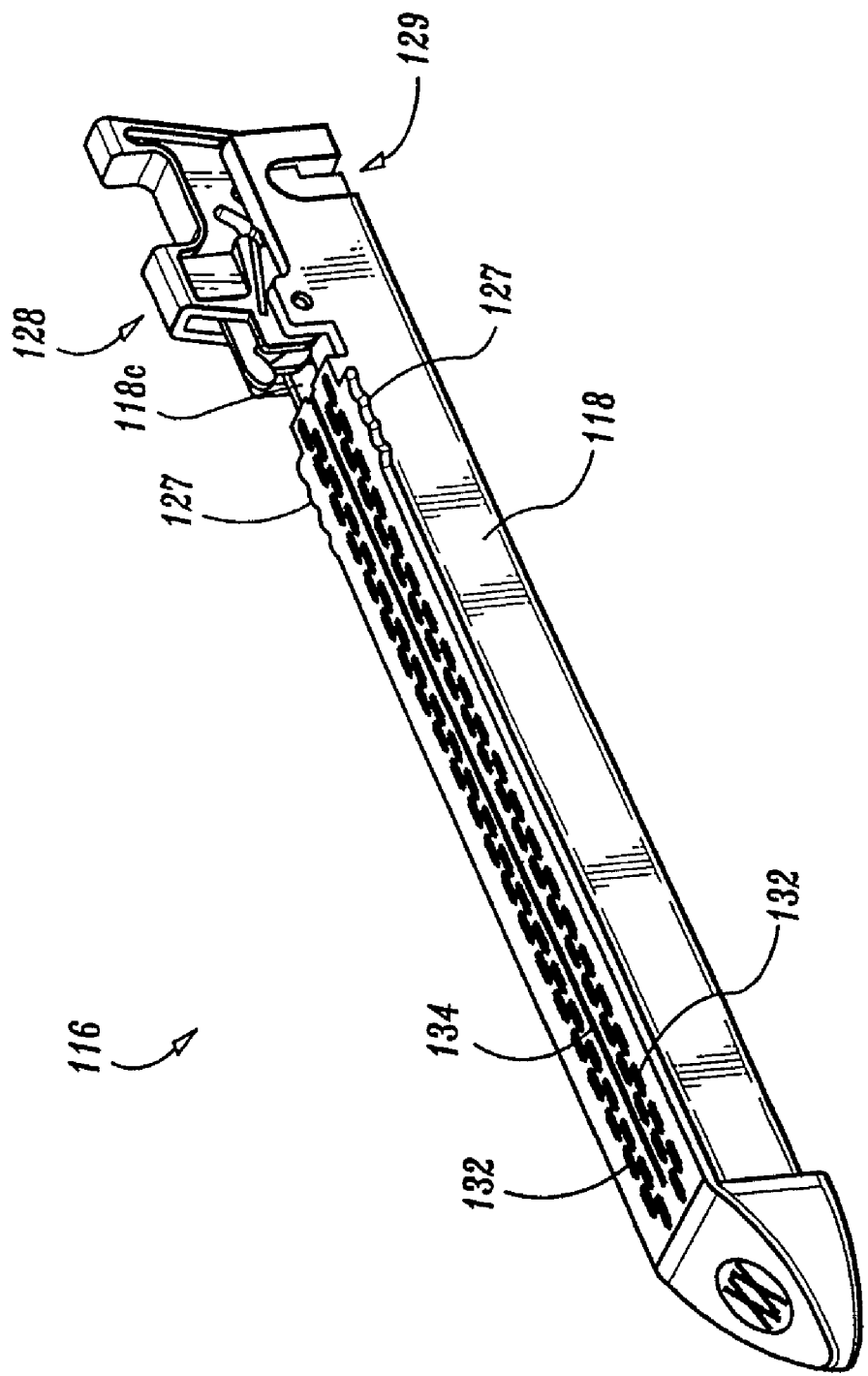
FIG. 24 is a perspective view of the disposable staple cartridge assembly as shown in FIG. 22 with the shipping wedge removed therefrom.
Figure 25:
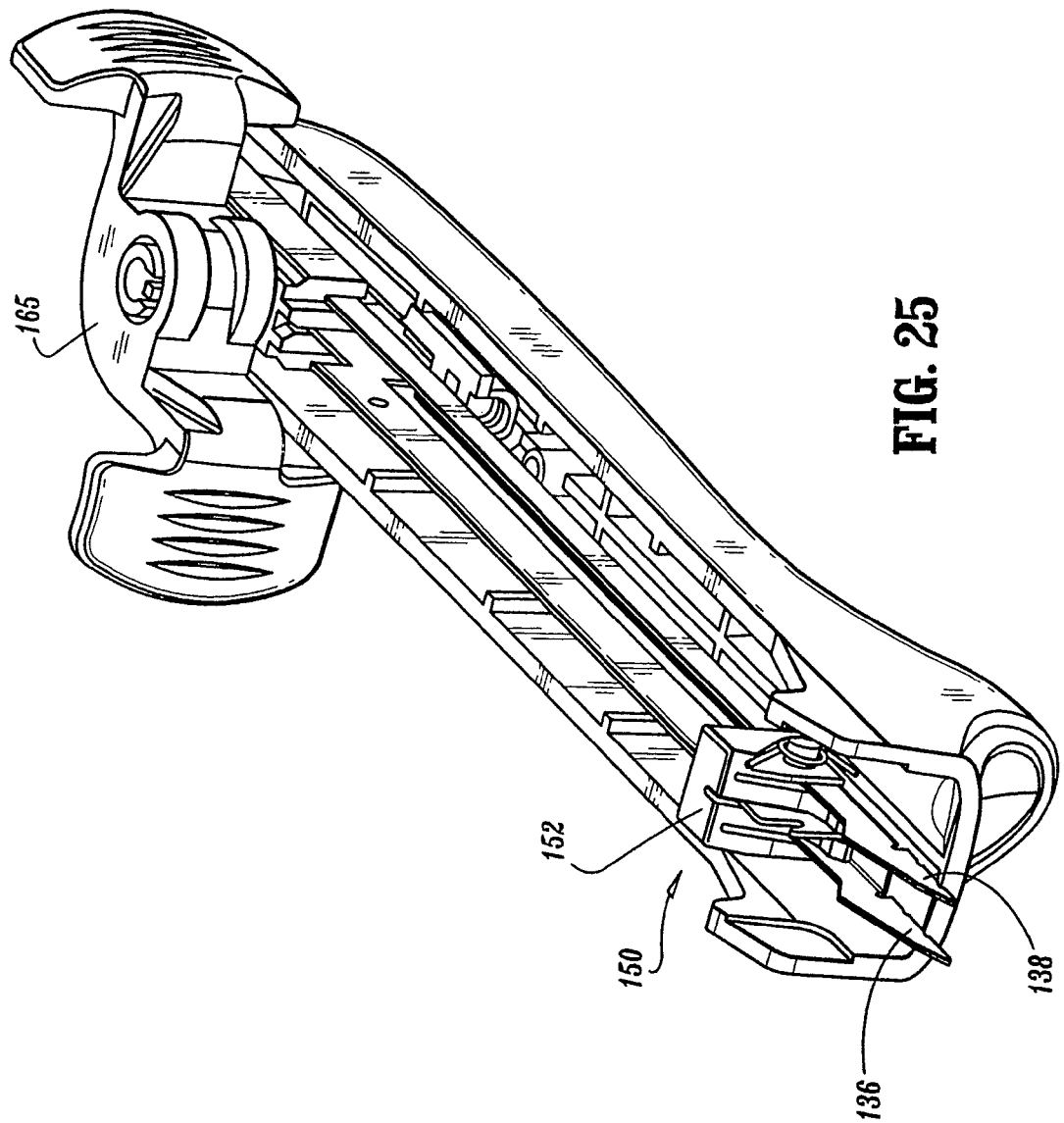
FIG. 25 is a perspective view of a proximal portion of a cartridge receiving half-section according to an alternative embodiment of the present disclosure.
Figure 27:
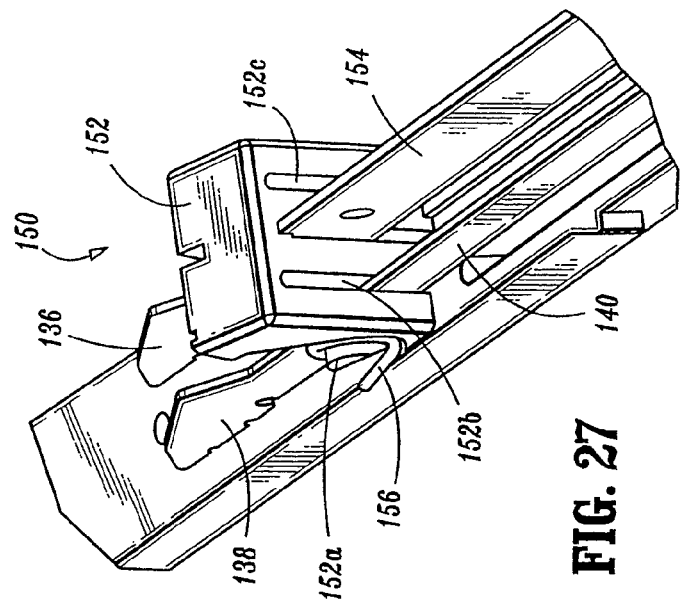
FIG. 27 is an enlarged right side proximal perspective view of the loading and lockout mechanism of FIG. 26.
Figure 26:
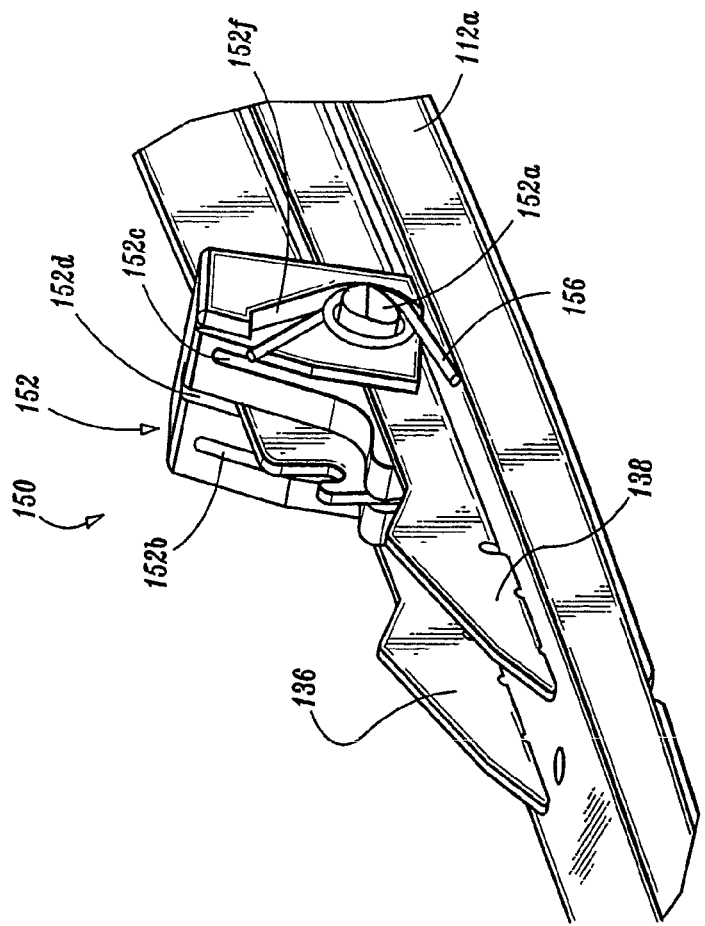
FIG. 26 is an enlarged left distal perspective view of a staple cartridge loading and lockout mechanism according to the alternative embodiment of FIG. 25.

Turning now to FIGS. 22-41, an alternative embodiment of a disposable staple cartridge assembly is generally shown as 116. As seen in FIGS. 22-24, staple cartridge assembly 116 includes a cartridge body 118, a plurality of staple pushers 120, a bottom cover 122, a knife 124 having an angled sharpened leading edge 124a and an atraumatic forward tip 124c, a plurality of staples 126, a pivotably mounted safety lockout 128 and a removable shipping wedge 130. As with known staple cartridge designs, cartridge body 118 has a plurality of rows of staple retaining slots 132 formed therein.

Alternatively, cartridge assembly 116 may be adapted such that one common surgical stapler 100 (see FIG. 33) will accept multiple different staple count cartridge assemblies 116. For example, cartridge assembly 116 may be configured such that each different staple count cartridge assembly 116 shares a common size cartridge body 118 to facilitate mounting on surgical stapler 100.

In the present illustrated embodiment, there are two staggered rows of slots 132 formed on either side of a linear slotted track 134 which guides knife 124 during its longitudinal movement. A single staple 126 is positioned in each of slots 132. The staple rows preferably extend a distance distally beyond the distal end of knife track 134 to facilitate staple formation beyond the stroke length of knife 124. Staple pushers 120 are formed such that they are attached to each other in groups of two offset oriented pusher pairs.

Staple pushers 120 are arranged in two series; one on each side of slotted track 134, such that the actuating surfaces of each series of staple pushers 120 forms a line centered between the staggered rows of staples 126. The actuating surfaces act as cam followers and interact with a pair of staggered camming surfaces 136 and 138 extending from a pair of cam bars 140 (see FIGS. 25-27) to expel the pairs of staples 126 on each side of knife track 134. As illustrated, camming surfaces 136 and 138 form a single angle relative to horizontal as each cam bar 140 is moved distally. This sequence is repeated until the distal movement of each cam bar 140 is either stopped intentionally by the user to form less than all of staples 126 or until all of staples 126 are expelled from cartridge assembly 116.

Bottom cover 122 partially encloses the bottom of a channel formed by the upper surface of the channel bottom wall and the side walls of cartridge body 118. A longitudinal ridge 122a is formed on an upper surface of bottom cover 122 and serves as a bearing surface for knife bearing channel 142, which is secured to the bottom edge of knife 124, as knife 124 travels in knife track 134. A pair of slots is formed one on either side of longitudinal ridge 122a, the outer limit of each slot being defined by the outer side wall of cartridge body 118 on a respective side of ridge 122a. These slots facilitate reciprocating longitudinal movement of the extensions of camming surfaces 136, 138 of generally U-shaped cam bar 140. Knife bearing channel member 142 which is preferably wider than knife track 134, is secured to the bottom surface of knife 124 such that knife bearing channel member 142 rides between knife track 134 and longitudinal ridge 122a of bottom cover 122. In this manner, knife 124 is prevented from undergoing substantial vertical movement during longitudinal translation in knife track 134.

Safety lockout 128 is pivotably disposed on the upper proximal end of cartridge body 118 and is movable from a locked orientation to an unlocked orientation. Preferably, safety lockout 128 is biased away from the locked orientation towards an orientation substantially perpendicular to the longitudinal axis of cartridge body 118. Any suitable bias member may be utilized such as, for example, spring 144. To overcome the bias towards the perpendicular orientation, safety lockout 128 includes a transverse horizontal surface 128a (see FIG. 35) formed on the underside thereof which engages a hook 124b formed on the upper edge surface of knife 124. This cooperative engagement serves to retain safety lockout 128 in the locked orientation when safety lockout 128 covers knife 124.

When surgical stapler 100 has been unclamped, as will be described in greater detail further herein, after either partial or complete firing, g, safety lockout 128 is biased to the perpendicular orientation (see FIG. 40), extending upwardly away from cartridge receiving half-section 112. In this manner, safety lockout 128 prevents surgical stapler 100 from being re-clamped until the partial or completely fired cartridge assembly 116 is removed and replaced with a new cartridge assembly 116. Safety lockout 128 also provides a cut-out grasping surface 128b with which cartridge assembly 116 may readily be removed from surgical stapler 100.

As previously noted, shipping wedge 130 is removably attachable to cartridge body 118. When installed on cartridge assembly 116, shipping wedge 130 covers the entire surface area of staple rows 126 and knife track 134. Shipping wedge 130 includes a post 130b extending downwardly from the underside thereof near the proximal end thereof. Post 130b fits into a complementary shaped opening 118c formed in cartridge body 118 at the proximal end of knife track 134.

With shipping wedge 130 in place, post 130b blocks potential distal movement of knife 126. Post 130b maintains knife 134 retained within safety lockout 128 thereby ensuring that the sharpened distal edge 124a of knife 124 is covered. Once again, cartridge assembly 116 may be provided without a knife in applications where it is desirable to perform stapling without transection. In such an embodiment, knife 126 is replaced with a blank element to substitute for the knife to interact with safety lockout 128.

Cartridge body 118 includes a series of finger grips 127 formed along the upper sides near a proximal end thereof. Finger grips 127 assist the user in gripping cartridge assembly 116 for both installation and removal of cartridge assembly 116 from cartridge receiving half-section 112. Cartridge body 118 also includes a pair of resilient friction fingers 129 disposed on either side near a proximal end thereof. Friction fingers 129 are configured and adapted to project outwardly from cartridge body 118 and to frictionally engage the inner surface of cartridge receiving half-section 112. In this manner, the friction fingers 129 prevent cartridge assembly 116 from falling out of the cartridge receiving half-section 112.

Referring to FIGS. 25-31, a loading and lockout mechanism 150 for cartridge assembly 116 will now be described in detail. Loading and lockout mechanism 150 facilitates loading of cartridge assembly 116 and prevents firing of surgical stapler 100 until cartridge assembly 116 is properly loaded on cartridge receiving half-section 112 and surgical stapler 100 is properly clamped shut. Loading and lockout mechanism 150 includes a rocker 152 which is pivotably mounted to a channel frame 112a (see FIG. 31) of cartridge receiving half-section 112 by way of transversely extending post portions 152a seating in openings formed through the sidewalls of channel frame 112a. Post portions 152a are provided with angled downwardly oriented surfaces to facilitate assembly of rocker 152 with channel frame 112a. Rocker 152 is preferably a molded plastic component and is provided with three slots, namely open bottomed slots 152b, 152c to permit longitudinal movement of cam bar 140 and a closed slot 152d to permit passage of a center bar 154 (see FIG. 27) therethrough.

Figure 28:
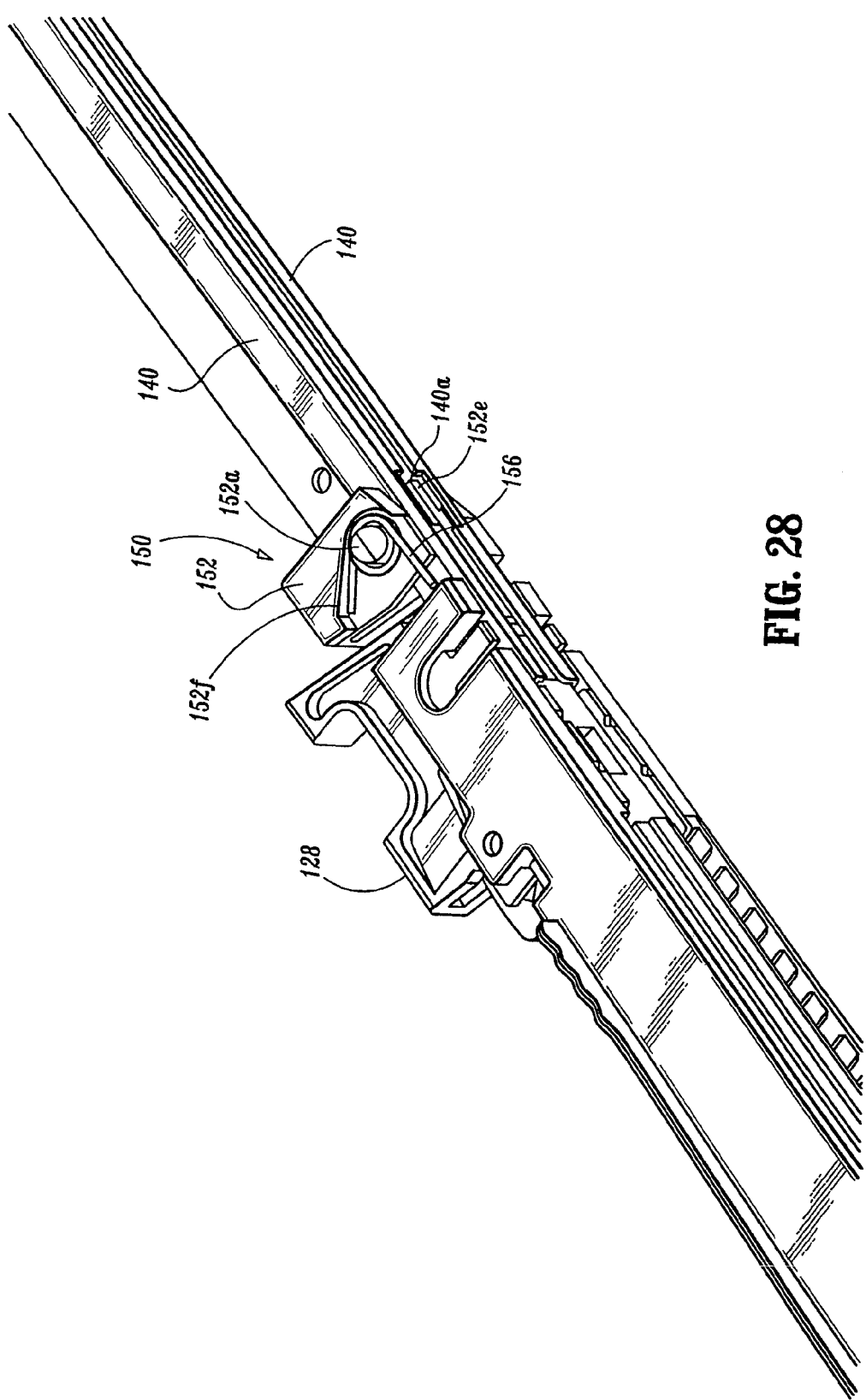
FIG. 28 is an enlarged bottom side perspective view of the loading and lock out mechanism of FIG. 26 with a staple cartridge assembly in place thereon.
Figure 29:
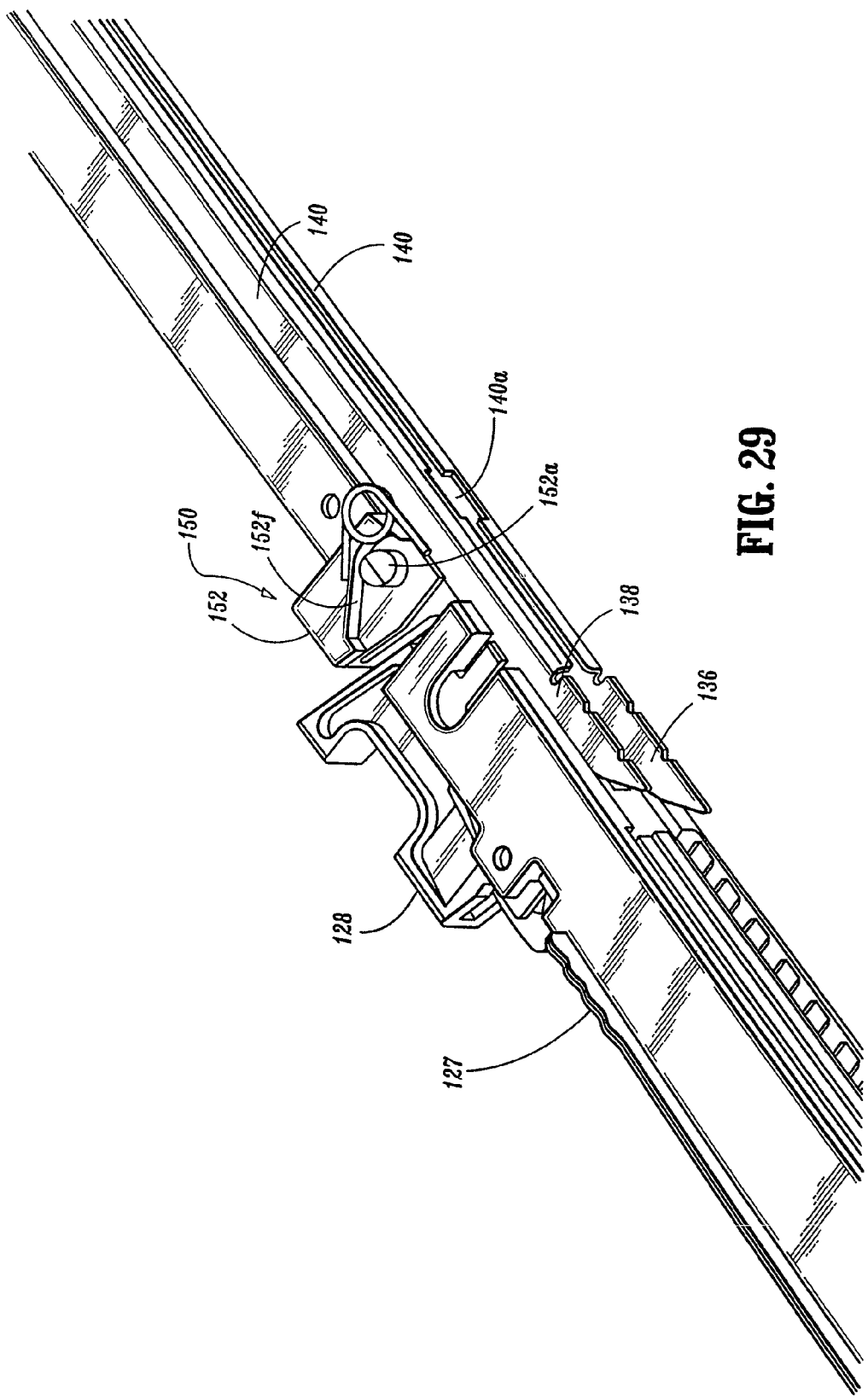
FIG. 29 is a partially exploded enlarged bottom side perspective view similar to that of the loading and lock out mechanism shown in FIG. 28.
Figure 30:
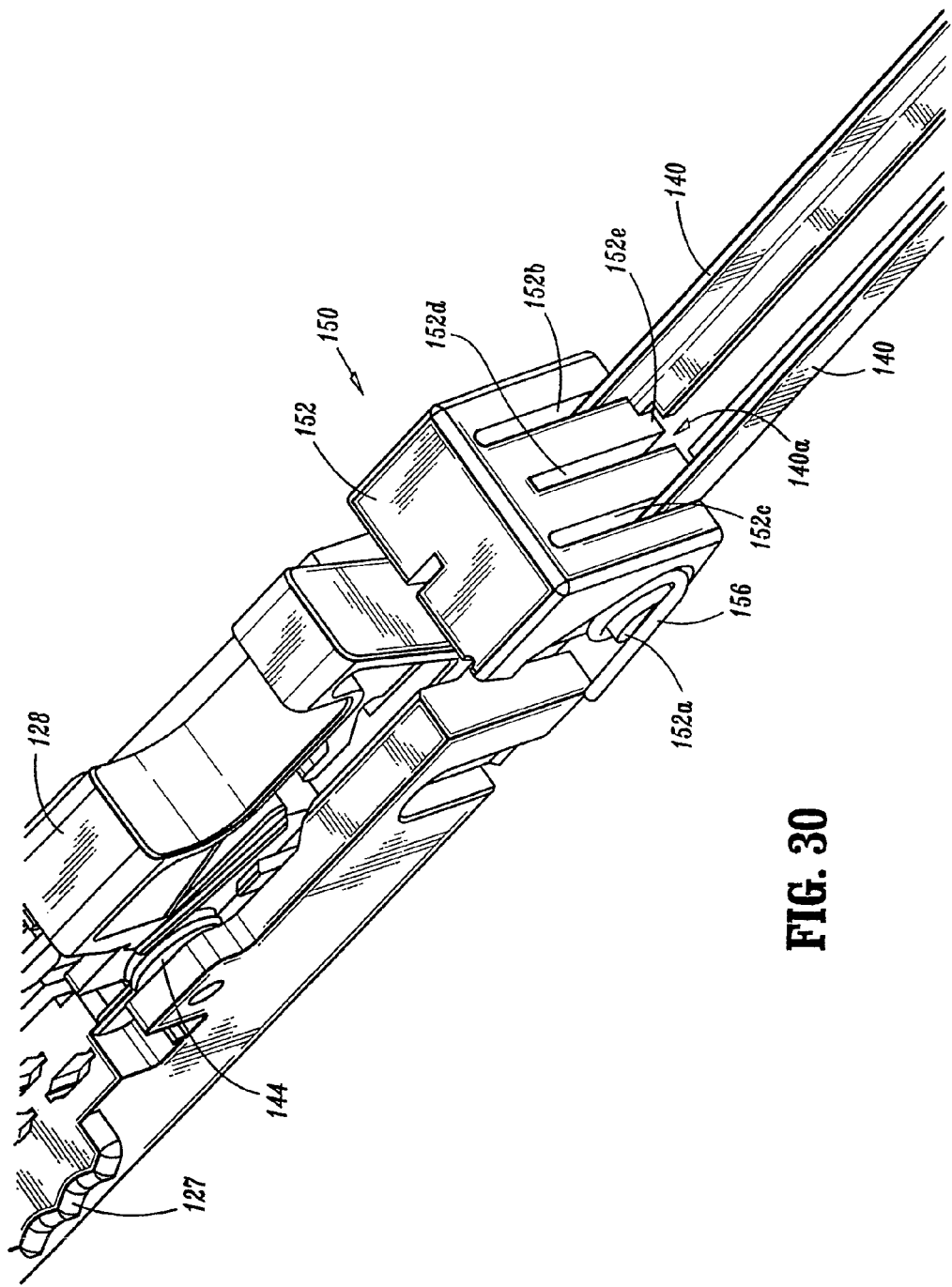
FIG. 30 is an enlarged top side perspective view similar to the loading and lock out mechanism of FIG. 27.
Figure 31:
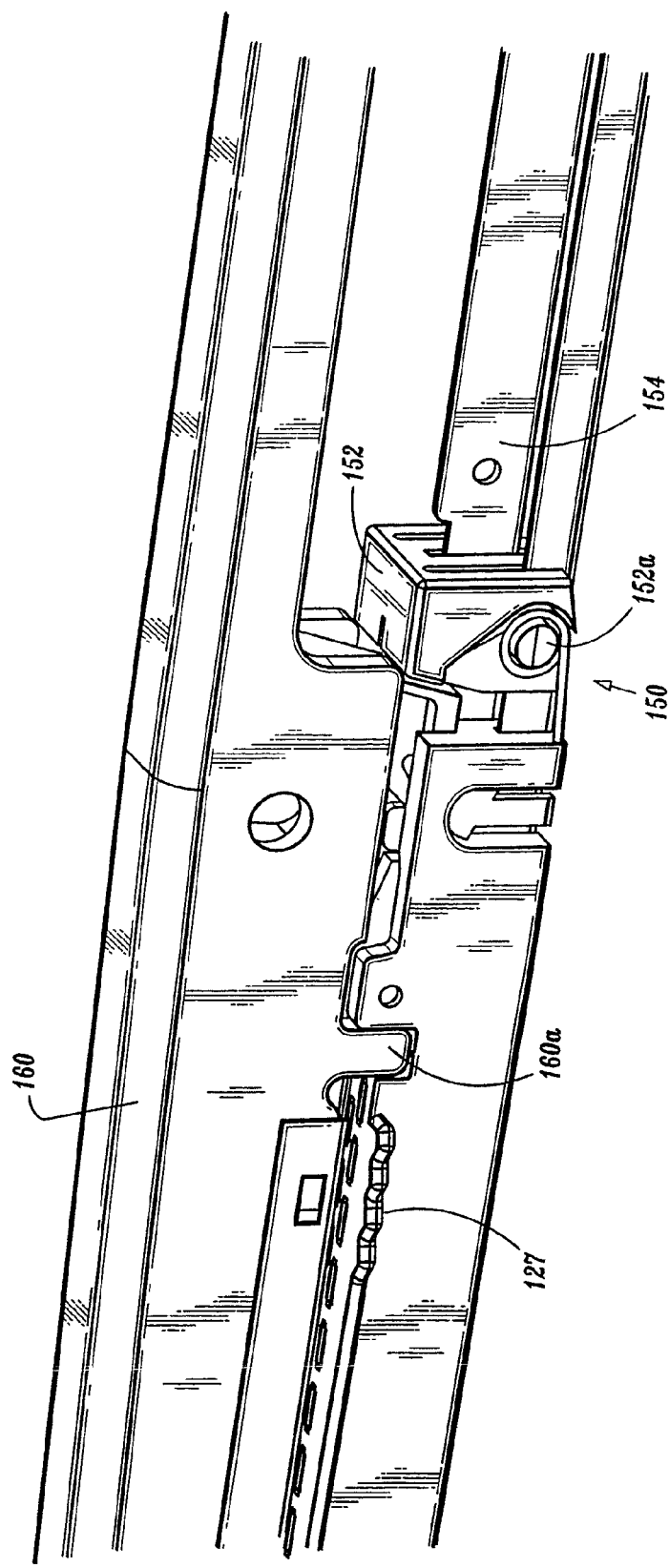
FIG. 31 is an enlarged side perspective view which shows the relative positioning of the loading and lockout mechanism with an anvil half-section in place thereon.

As best shown in FIG. 28, rocker 152 is further provided with a downwardly extending blocking surface 152e which is in vertical alignment with an opening 140a formed through the bottom surface of each cam bar 140 when each cam bar 140 is in its proximal-most position. Rocker 152 is biased, by way of a spring 156 which is disposed on transversely extending post portion 152a and between a ridge 152f formed on a side of the rocker 152 and upper surface of the cartridge half section 112 (see FIG. 26), toward a locked-out position wherein blocking surface 152e extends through opening 140a. In this manner, each cam bar 140 is prevented from distal longitudinal movement.

Upon loading cartridge assembly 116 on cartridge receiving half-section 112 as shown in FIGS. 26-31, the spring bias maintains rocker 152 in the locked-out position. It is only when anvil half-section 114 is joined with cartridge receiving half-section 112 and the half-sections clamped together, thereby causing downwardly extending leg portions 160a formed on either side of anvil half-section channel member 160 to bias against cartridge assembly 116, that rocker 152 is urged to rotate by the caroming action of proximal end surface of cartridge assembly 116 against the distal end surface of rocker 152. In this manner, blocking surface 152e is moved out of (i.e., pivoted out of) longitudinal alignment with opening 140a of each cam bar 140 thereby permitting a distal longitudinal movement of cam bar 140.

Similar to the embodiment shown in FIGS. 2-21, once surgical stapler 100 has been at least partially fired, if the instrument is opened, safety lockout 128 of cartridge assembly 116 automatically moves to the perpendicular orientation due to the spring bias mounting thereof. With safety lockout 28 in this orientation, surgical stapler 100 cannot be re-clamped. Thus, if the user desires to apply further staples, fired or partially fired cartridge assembly 116 must first be removed and replaced with a non-fired cartridge assembly 116.

Figure 32:
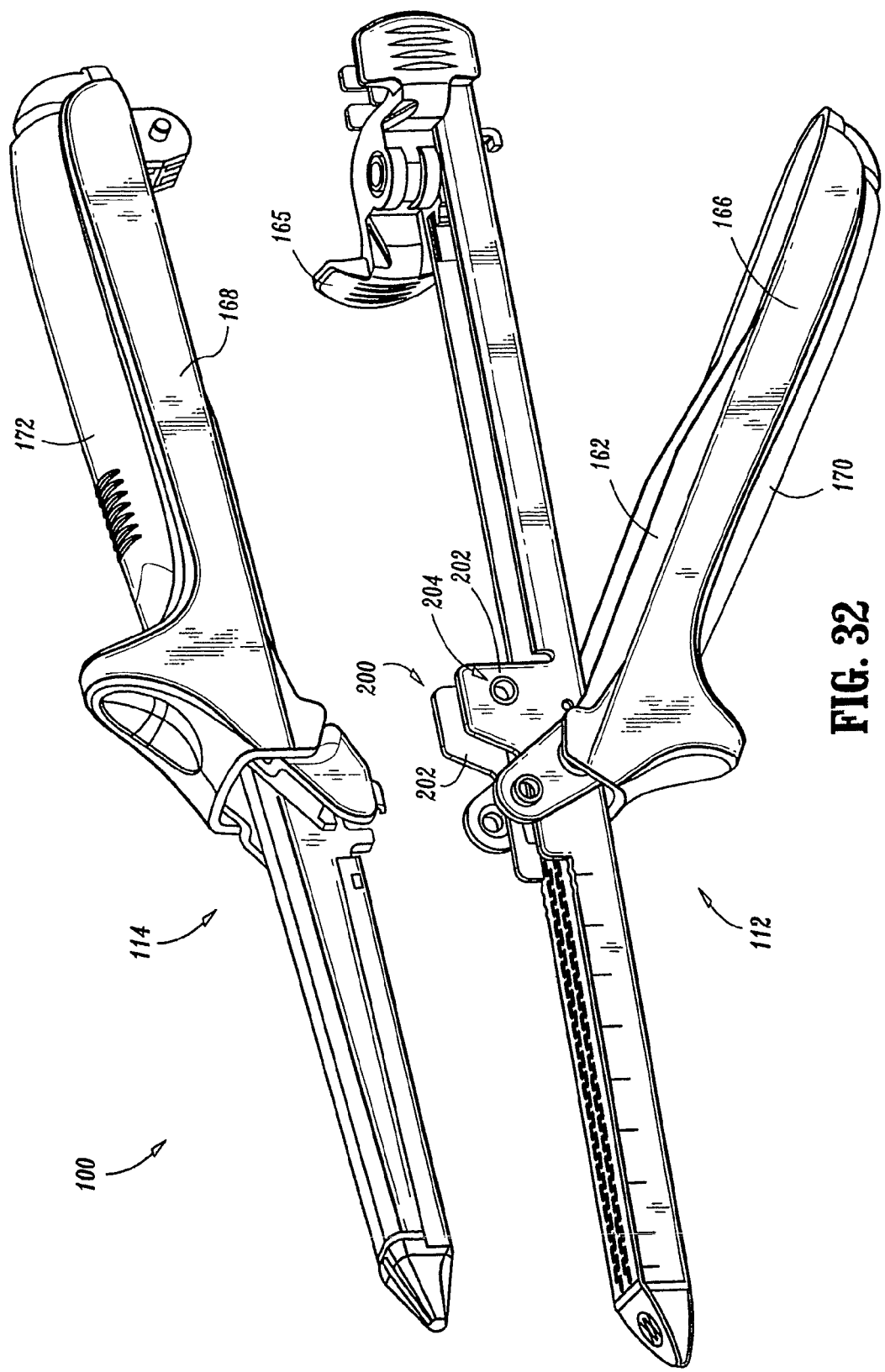
FIG. 32 is a perspective view of the surgical fastener applying apparatus of FIGS. 21-40, in an unclamped condition, with a cartridge receiving half-section clamp lever in an open position.

Referring to FIG. 32, surgical stapler 100 is provided with clamping lever 162 and a pivotably mounted firing lever 165. Like firing lever 65 of the first embodiment, firing lever 165 of the present embodiment provides the user with the ability to fire surgical stapler 100 from either the left or right side.

Clamping lever 162 is pivotably mounted to cartridge receiving half-section 112. An ergonomic contoured handle 166 is secured to clamping lever 162 to provide the user with a convenient gripping handle. To further enhance the gripping of surgical stapler 100 by the user, a friction enhancing insert 170 is secured to handle 166.

Unlike the embodiment of FIGS. 2-21, the surgical stapler 100 of FIGS. 22-41 does not include a clamp latch safety interlock mechanism. In this manner, the user can open the surgical stapler 100 after a complete or partial firing of the cartridge assembly 116. Referring now to FIGS. 33-39, a clamp latch mechanism, according to the alternative embodiment, is provided at the proximal end of surgical stapler 100 which serves to retain clamp lever 162 in a clamped orientation. Cartridge receiving half-section 112 is provided with a clamp latch mechanism which works to latch clamp lever 162 in a clamped configuration upon squeezing clamp lever 162 to the closed position. Once again, while a single clamp lever 162 is shown and described as being pivotably mounted to cartridge receiving half-section 112, it is envisioned that a clamp lever can be pivotably mounted to anvil half-section 114 or a clamp lever can be pivotably mounted to each of cartridge receiving half-section 112 and anvil half-section 114. Accordingly, the following description of the various components which make up the clamp latch mechanism will be directed to that for the cartridge receiving half-section 112.

Figure 33:
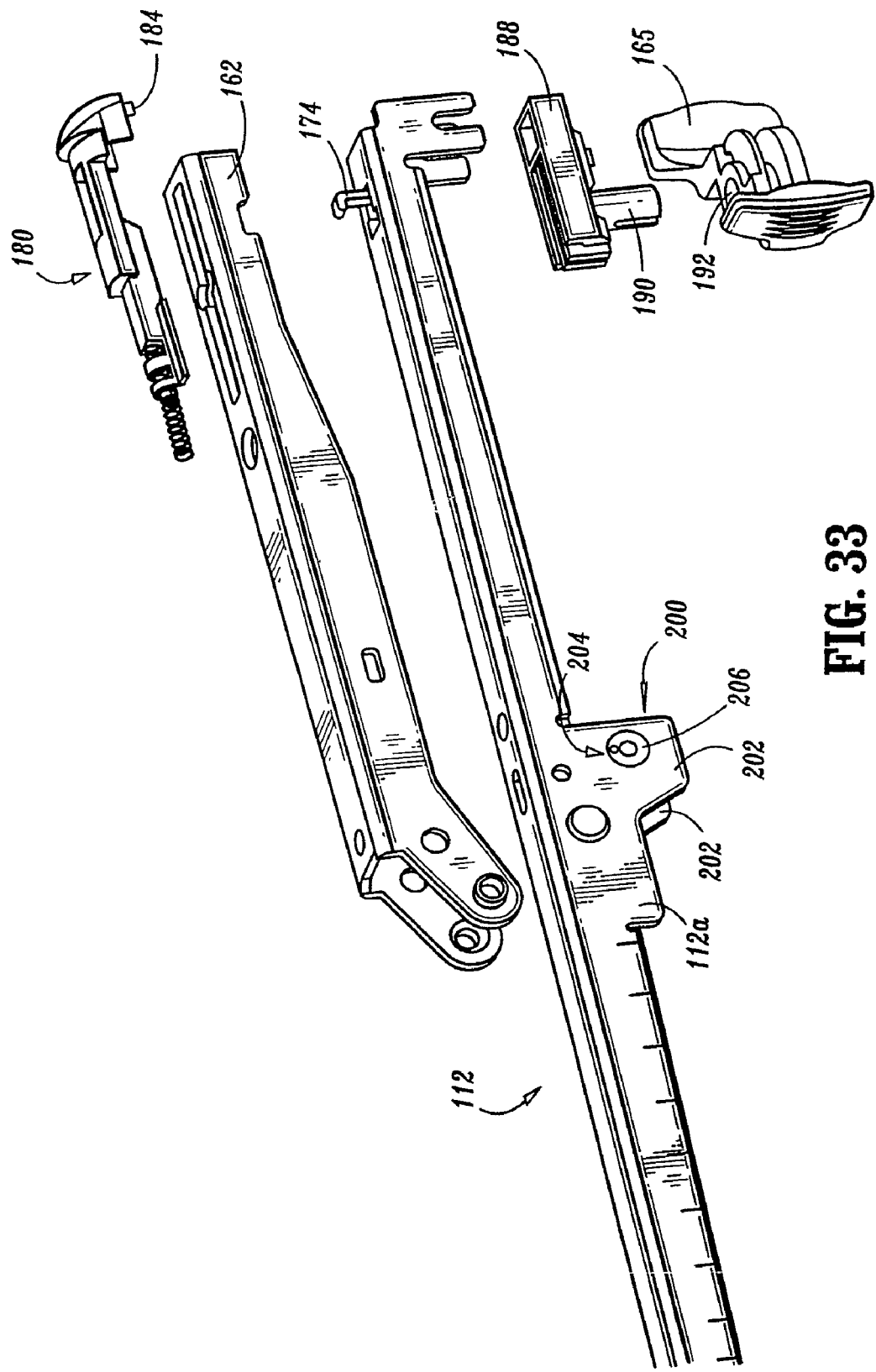
FIG. 33 is a perspective view, with parts separated, which shows the structural relationship of the various components of a clamp lever lockout and safety interlock mechanism.
Figure 40:
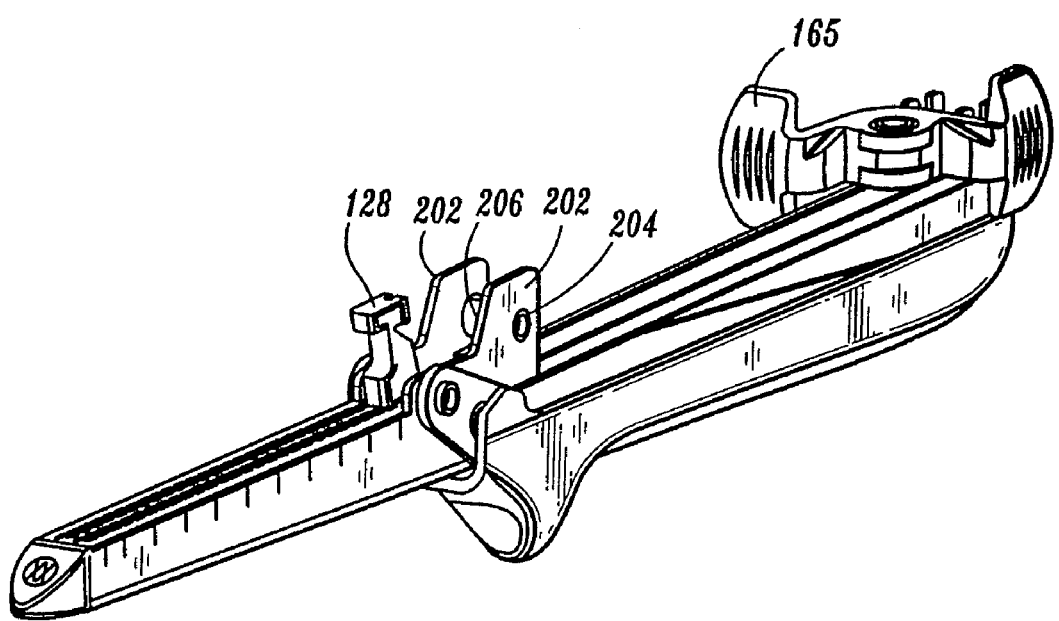
FIG. 40 is a perspective view of the cartridge receiving half-section of the surgical fastener applying apparatus of FIGS. 21-40 after partial or complete firing with a staple cartridge safety lockout in a locked out position.
Figure 41:
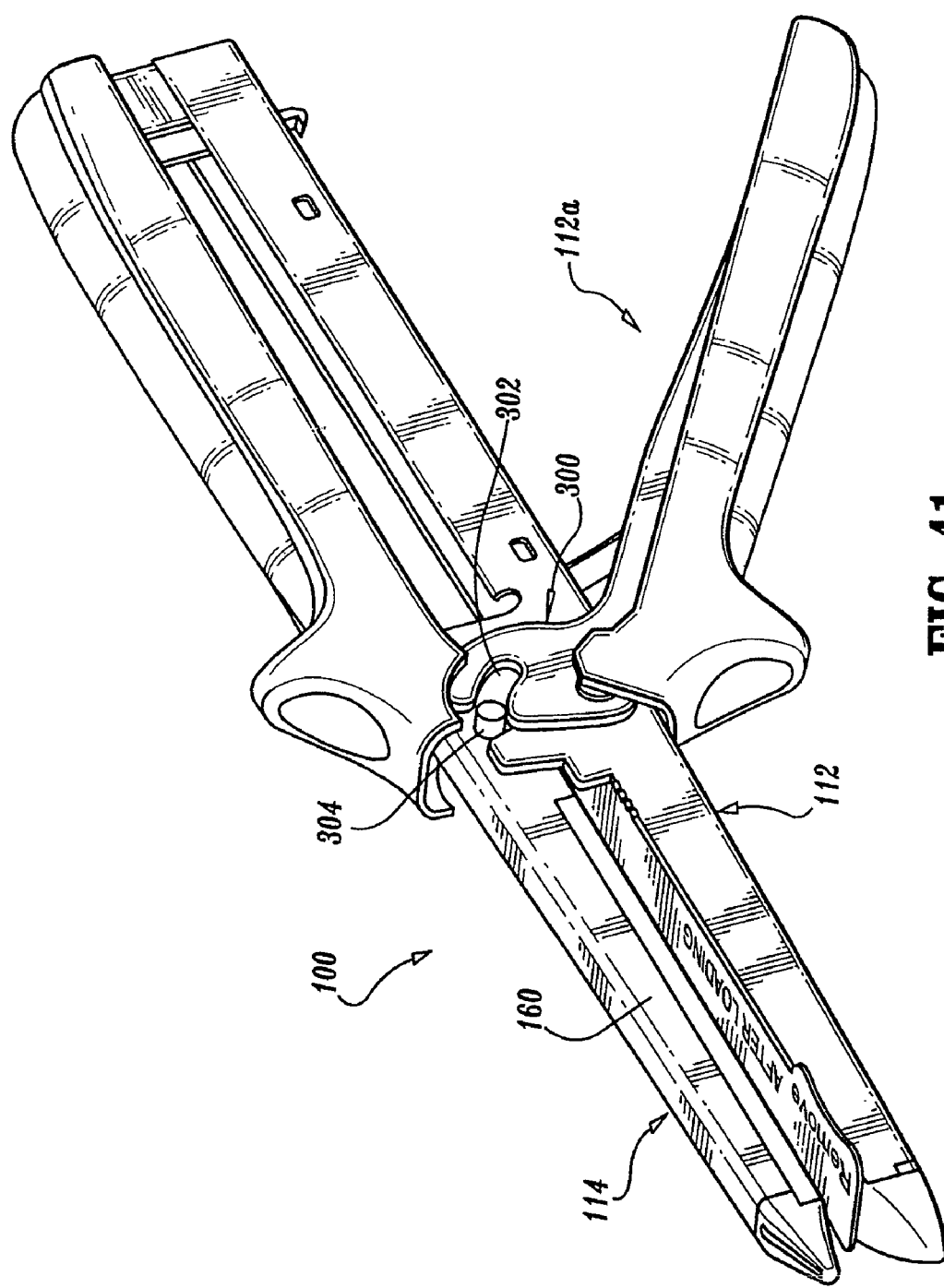
FIG. 41 is a schematic perspective view of a surgical fastener applying apparatus according to another alternative embodiment of the present disclosure, with a cartridge receiving half-section clamp lever shown in an open position.

As shown in FIG. 33, the clamp latch mechanism includes a distal clamp lever latch 174 formed at a proximal end of the cartridge receiving half-section 112 and latch handle release member 180 operatively coupled to a proximal end of clamp lever 162. Latch handle release member 180 is spring biased proximally toward a latched position and is provided with a catch 182 (see FIG. 36) for engaging clamp lever latch 174. In order to release clamp lever 162, the user presses release member 180 in the distal direction, thereby disengaging catch 182 from latch 174.

In order to prevent inadvertent opening of the clamp lever 162, release member 180 is provided with a projection 184 extending downwardly from a proximal end thereof, which projection 184 is seated within a guard 186 formed at the proximal end of the lever 162. It is envisioned that the guard 186 can be integral with the handles 166 and 168 and made of a resilient material to enable the user to more easily move the guard 186 and thereby depress the release member 180.

Further, as seen in FIG. 33, surgical stapler 100 is provided with a firing lever slide block 188. Slide block 188 includes a hub 190 projecting therefrom and configured and adapted to be received in a pivot hole 192 formed in firing lever 165. Slide block 188 is configured and adapted to be slidably received in the cartridge receiving half-section 112. In use, firing lever 165 is pivotable about hub 190 thereby providing the user with the ability to manipulate firing lever 165 from either side of the surgical stapler 100.

As seen in FIGS. 32-35, 37, 38 and 40, surgical stapler 100 is provided with a staple gap adjustment mechanism 200 which enables each stapler 100 to be manufactured and assembled with a very precise staple gap between the cartridge assembly and the anvil structure of the surgical stapler. The staple gap adjustment mechanism 200 shown in FIGS. 32-35, 37, 38 and 40 is the subject of commonly owned and co-pending International Application PCT/US02/31963 filed on Oct. 4, 2002 which claims the benefit of and priority to U.S. Provisional Application Ser. No. 60/327,369, filed on Oct. 5, 2001, entitled "Surgical Stapling Apparatus", the entire contents of which are incorporated herein by reference. According to the present embodiment, gap adjustment mechanism 200 includes a pair of upstanding hinge plates 202 formed along the sides of the cartridge receiving half-section 112, and an eccentric cam 206. Each hinge plate 202 is provided with a coaxial through hole 204 which is configured and adapted to receive the eccentric cam 206 therein. In use, as eccentric cam 206 is rotated, a central portion, for example, 474 in FIG. 58A, of eccentric cam 206 presses against portions of anvil half-section 114 while end portions, for example, 472 and 476 of FIG. 58A, of eccentric cam 206 press against a portion of cartridge receiving half-section 122 until the desired staple gap between the anvil half-section 114 and the cartridge half section 112 is achieved. Once it is achieved, eccentric cam 206 is fixedly secured in the through holes 204. This feature will be discussed in greater detail below.

Figure 42:
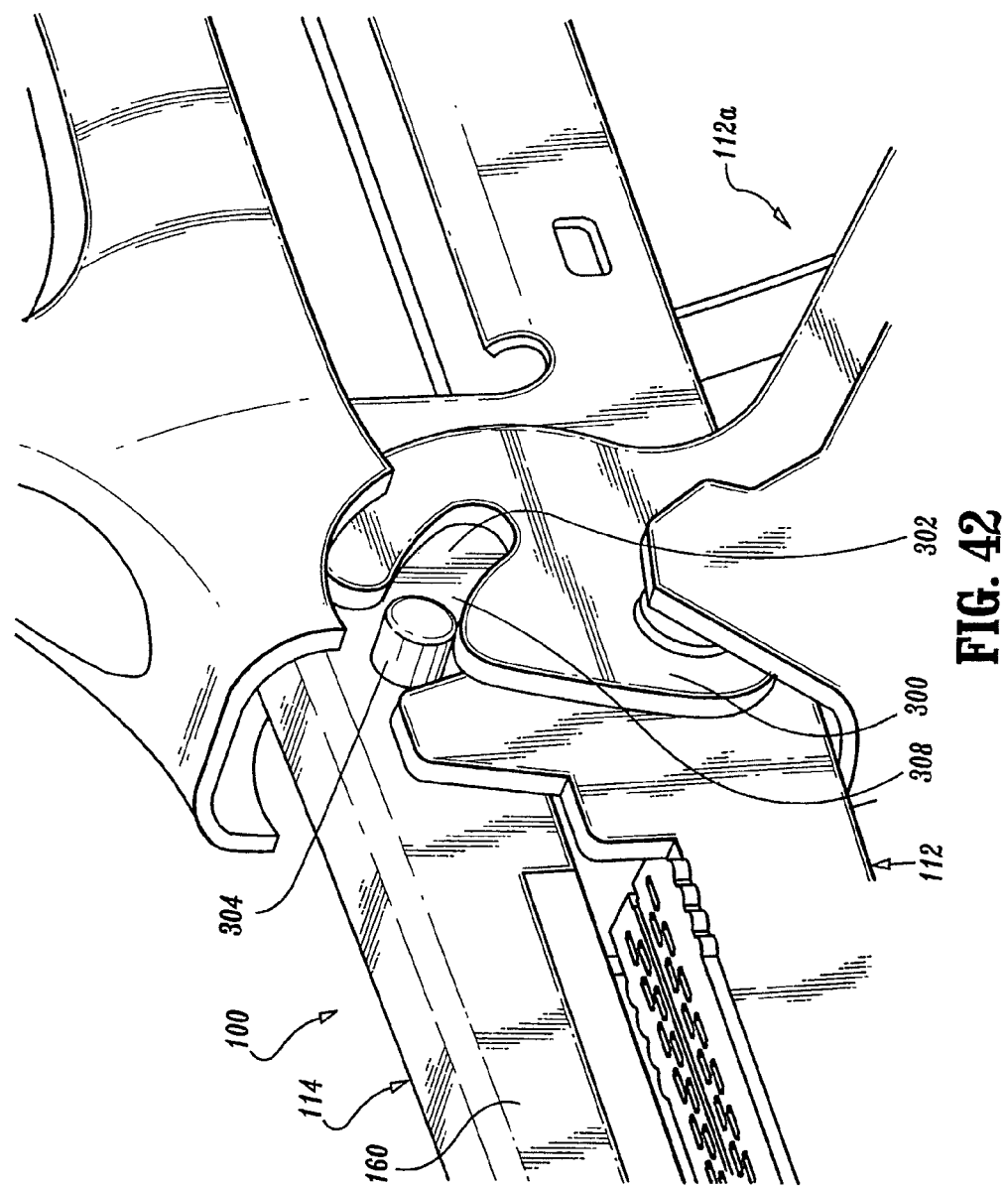
FIG. 42 is an enlarged schematic perspective view of the mounting bracket of the cartridge receiving half-section clamp lever shown in FIG. 41.
Figure 43:
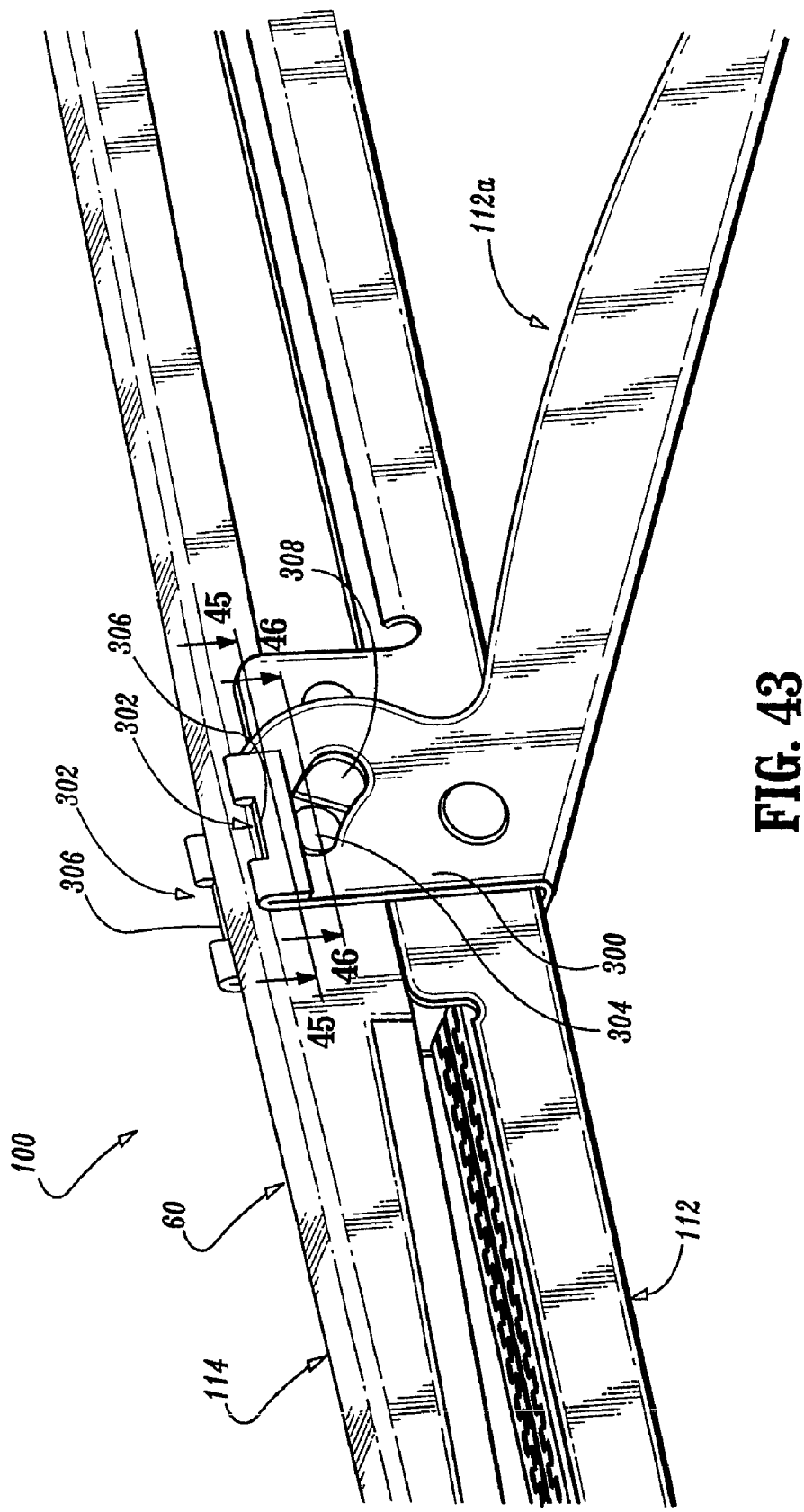
FIG. 43 is an enlarged schematic perspective view of an alternate embodiment of a mounting bracket for the cartridge receiving half-section clamp lever shown in FIG. 41 with the cartridge receiving half-section clamp lever shown in an open condition.

Turning now to FIGS. 41-49, an alternative embodiment of surgical stapler 100 is depicted in which surgical stapler 100 includes a cartridge receiving half-section clamp lever 112a having a pair of juxtaposed mounting brackets 300 formed at a distal end thereof. Each mounting bracket 300 is provided with an access slot 302 formed therein. Preferably, each access slot 302 is oriented or accessible substantially vertically (i.e., oriented substantially orthogonally with respect to a longitudinal axis of surgical stapler 100) when cartridge receiving half-section clamp lever 112a is in an open position (as seen in FIGS. 42 and 43). More preferably, each access slot is oriented to face mounting pins 304 when clamp lever 112a is in the open position. Each access slot 302 is configured and adapted to slidably receive a terminal end of a mounting pin 304 which extends and projects from the lateral surfaces of anvil receiving half-section 114 a distance sufficient to engage each access slot 302 and has a cross-sectional dimension enabling it to be received within each access slot 302 (see FIGS. 45 and 46).

It is envisioned that each mounting bracket 300 can be provided with a reinforcing member 306 (see FIGS. 42-44) extending across each access slot 302 for strengthening, supporting and reinforcing the distal end of each access slot 302. Preferably, each reinforcing member 306 can be formed by stamping out an elongated slot in each mounting bracket 300 and folding or doubling over a distal end of mounting bracket 300, over or across the elongated slot, to thereby provide an open distal end of each access slot 302 and to create reinforcing member 306. Alternatively, each reinforcing member 306 can be formed by terminating each mounting bracket 300 at a point along the access slot 302 and fixedly attaching a crossbar across access slot 302, or by any other suitable method known by those skilled in the art. Each access slot 302 extends into and interconnects with a cam slot 308 also formed in each mounting bracket 300.

Figure 44:
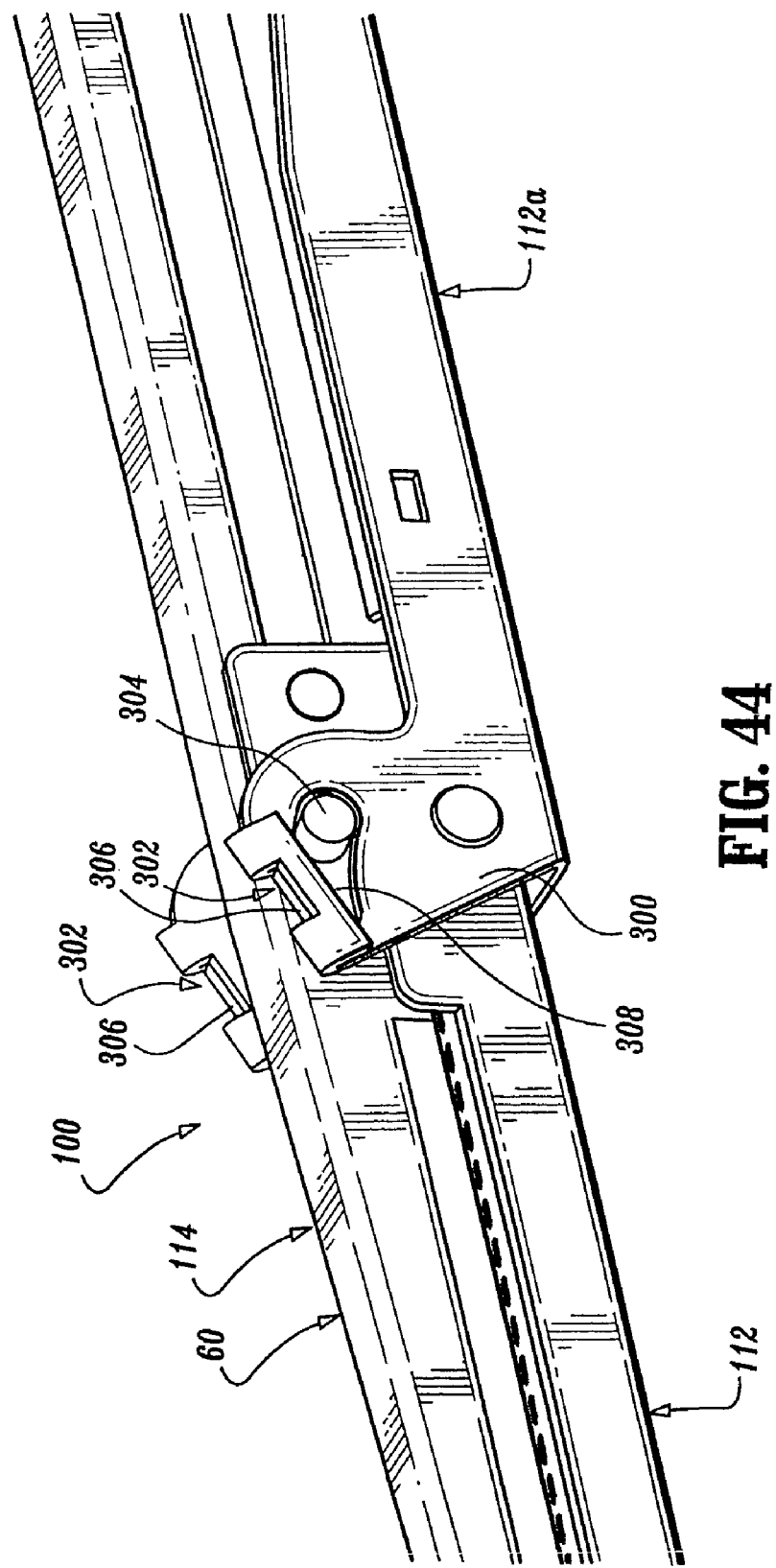
FIG. 44 is an enlarged perspective view of the mounting bracket of FIG. 43 with the cartridge receiving half-section clamp lever shown in a closed condition.
Figure 45:
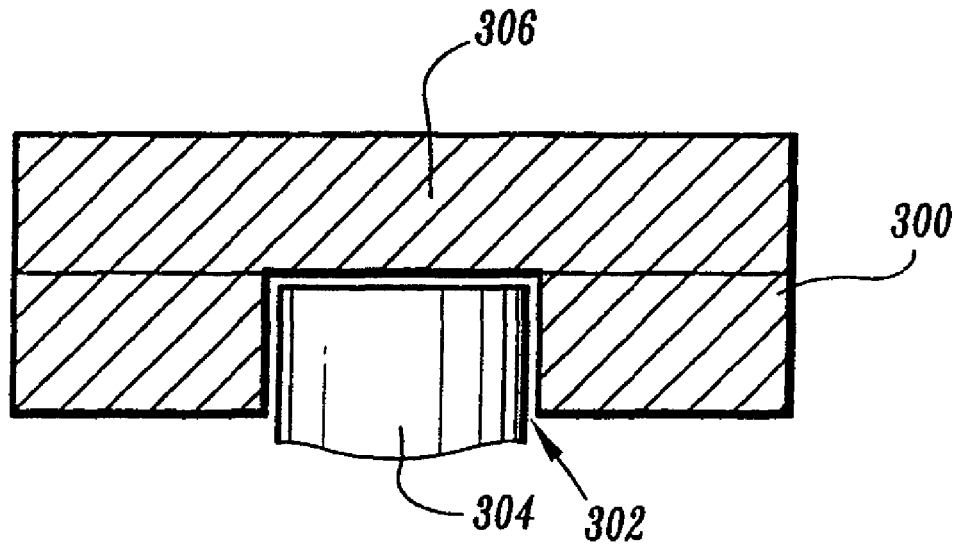
FIG. 45 is a cross-sectional view of the mounting bracket of FIG. 43 taken along section line 45-45.
Figure 46:
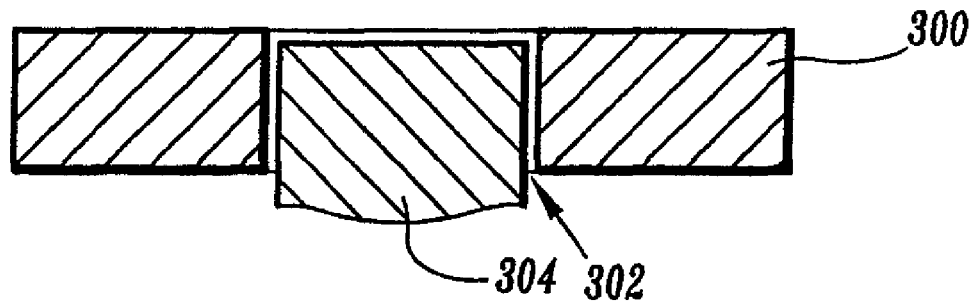
FIG. 46 is a cross-sectional view of the mounting bracket of FIG. 43 taken along section line 46-46.
Figure 47:
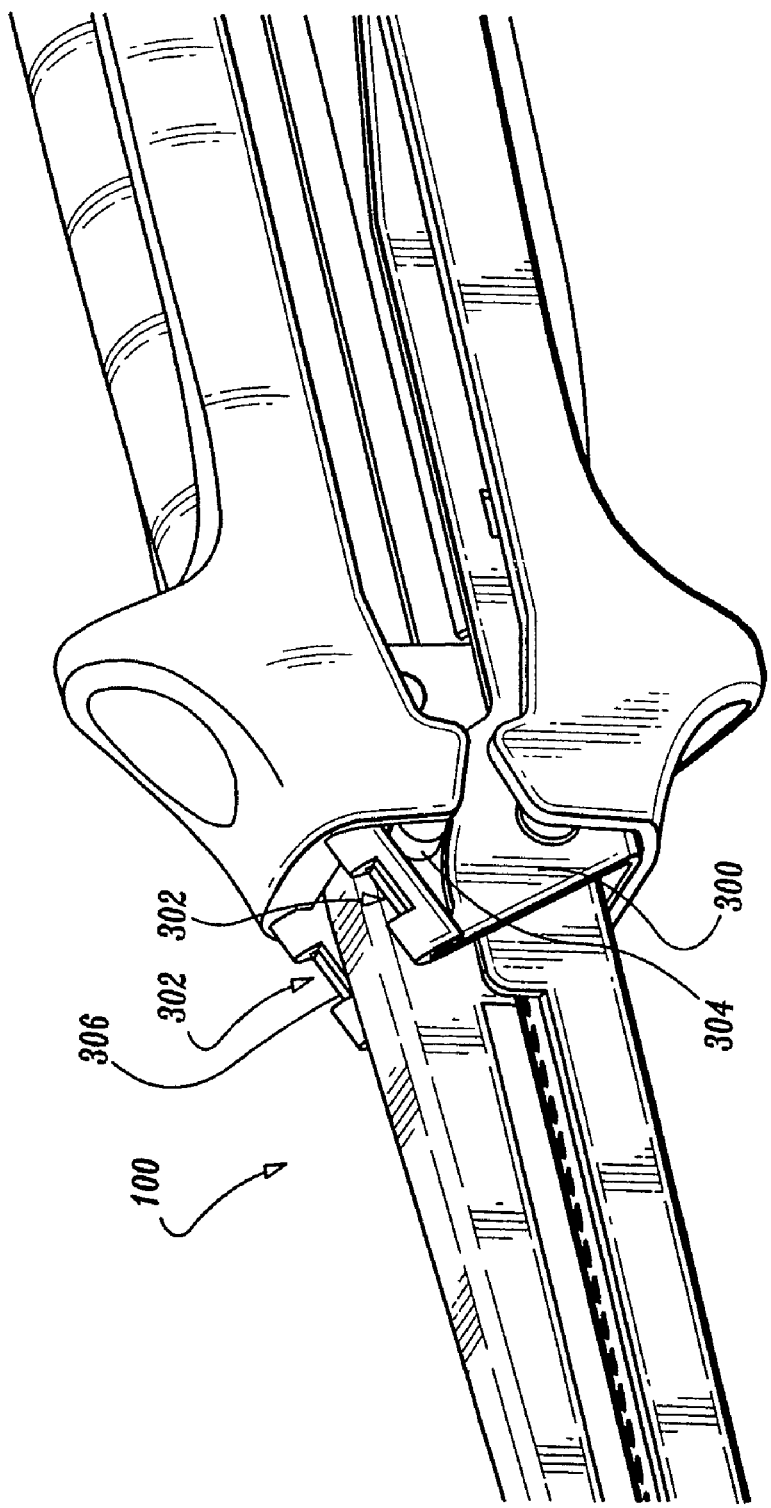
FIG. 47 is an enlarged schematic perspective view of the mounting bracket of FIG. 43 with a handle cover covering each of the cartridge and the anvil half-section clamp levers.

Mounting of anvil half-section 114 to cartridge receiving half-section 112 will now be described in connection with FIGS. 43, 44 and 47. With cartridge receiving half-section clamp lever 112a in an open position, anvil half-section 114 is united with cartridge receiving half-section 112 by aligning each opposed mounting pin 304 with a respective access slot 302 and advancing (i.e., moved forward, dropped-in, etc.) cartridge receiving and anvil half-section 112, 114 toward one another until mounting pins 304 are completely seated within access slots 302. Access slots 302 ensure that half-sections 112, 114 are juxtaposed and in proper alignment with one another. Once mounting pin 304 is properly and completely seated within access slot 302, cartridge receiving half-section clamp lever 112a is manipulated (i.e., pivoted) to a closed position (as seen in FIGS. 44 and 47) whereby each end of mounting pin 304 is advanced through cam slots 308 thereby closing surgical stapler 100 as a result of the camming action taking place therebetween.

Preferably, when the anvil receiving half-section 114 is oriented in the horizontal plane and the clamp lever 112a is in the first position, the opening to each access slot 302 can be vertically accessed. It is envisioned that each access channel 302 is generally orthogonal to the cartridge receiving half-section 112. As seen in FIG. 42, it is further envisioned that each access channel 302 faces angularly relative to the cartridge receiving half-section 112. It is contemplated that each access slot 302 can be generally L-shaped.

As seen throughout the figures the distal end of the anvil half-sections preferably taper downwardly in height from a proximal end portion toward the distal end portion thereof. By way of example only, the proximal end portion of the anvil half-sections preferably have a height of about 11.7 mm while the distal end portions of the anvil half-sections preferably have a height of about 10.2 mm, when the anvil half-sections have a length of about 100 mm.

In order to reinforce and strengthen the distal end of the anvil half-sections and to reduce a tendency of the distal end of the anvil half sections to deflect as a result of the stapling forces acting thereon, it is envisioned that at least one vertically oriented longitudinally running reinforcing strip (not shown in the present embodiment) is provided therewithin. The reinforcing strip is preferably made of a substantially rigid non-flexible material, such as, for example, stainless steel. It is contemplated that the reinforcing strip can be either welded, crimped and/or snapped or otherwise friction fit into place. It is further envisioned that the distal end of the anvil half-sections are provided with at least one transverse and/or longitudinal reinforcing wall (not shown) in order to reduce the tendency of the distal end of the anvil half-sections from deforming due to torsional forces.

Figure 48:
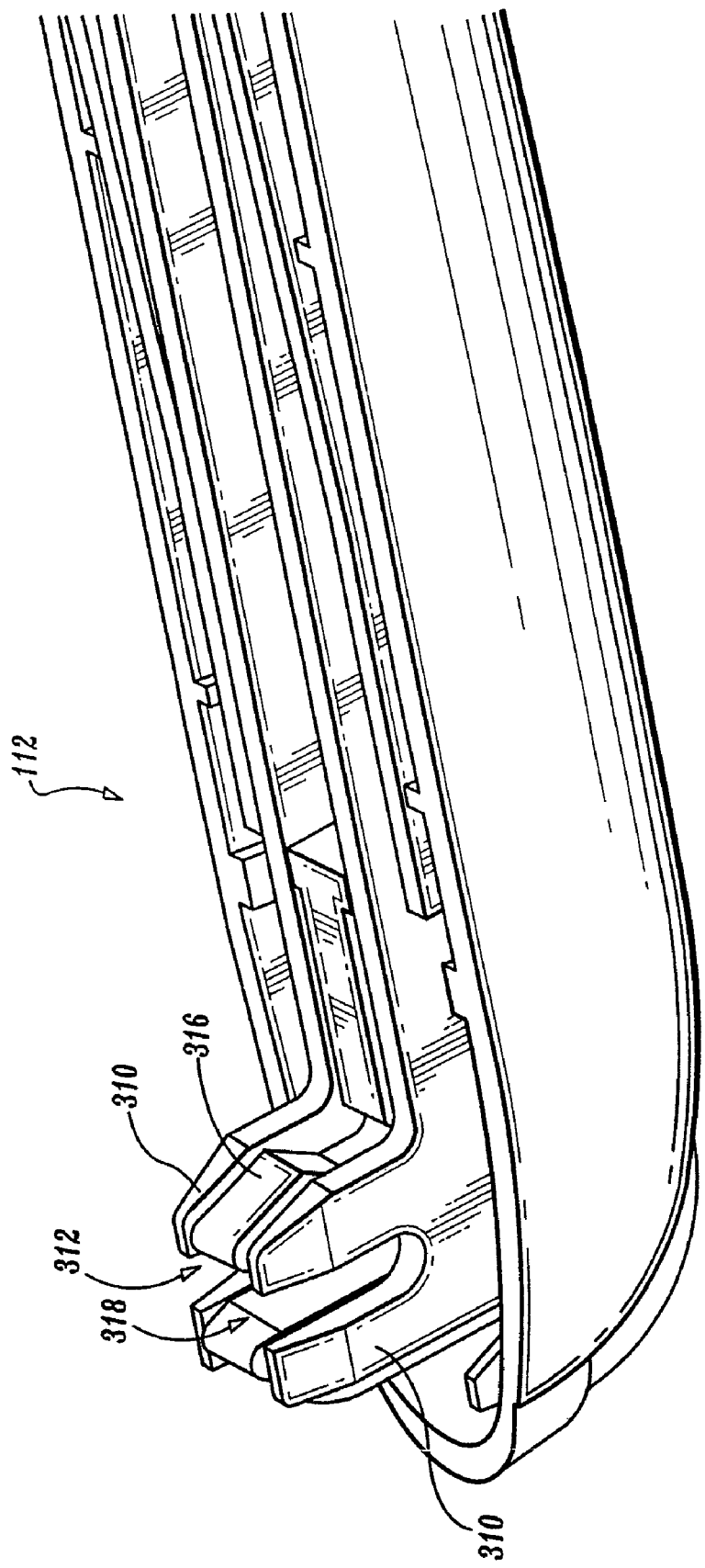
FIG. 48 is an enlarged perspective view of the underneath of a proximal end of an anvil frame side with the anvil half-section clamp lever in the closed position.
Figure 49:
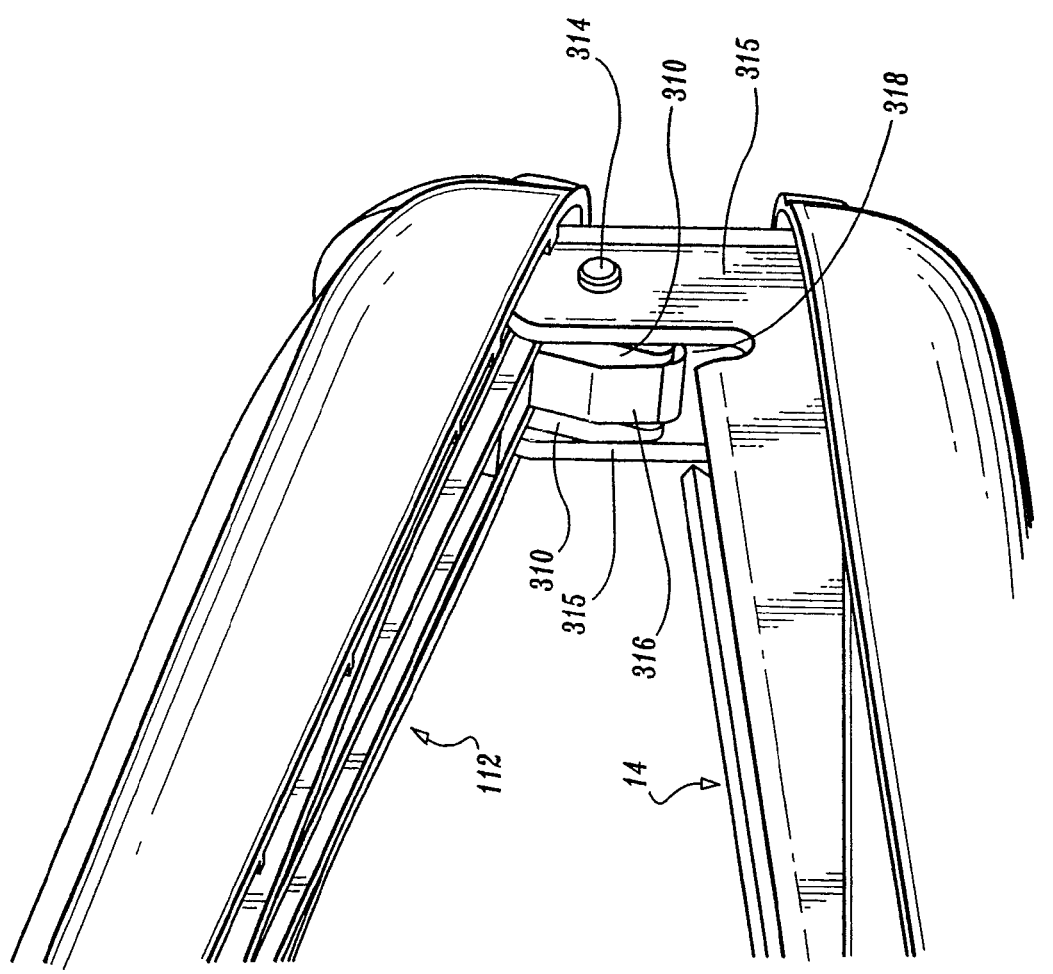
FIG. 49 is a perspective view of the proximal end of the surgical fastener applying apparatus depicting the engagement of the proximal ends of the cartridge and anvil half-section clamp levers.

Turning now to FIGS. 48 and 49, the proximal end of cartridge receiving half-section 112 is provided with a pair of juxtaposed pivot plates 310 extending upwardly therefrom. Each pivot plate 310 is provided with a pivot pin receiving slot 312 for receiving a pivot pin 314 (See FIG. 49) extending between and through a pair of end plates 315 located at a proximal end of anvil half-section 114. It is contemplated that a reinforcing member 316 is provided between pivot plates 310 and is provided with a slot 318 corresponding to pivot pin receiving slots 312. It is contemplated that reinforcing member 316 can be a separate member or members secured between, or unitarily or integrally formed with pivot plates 310.

Figure 50:
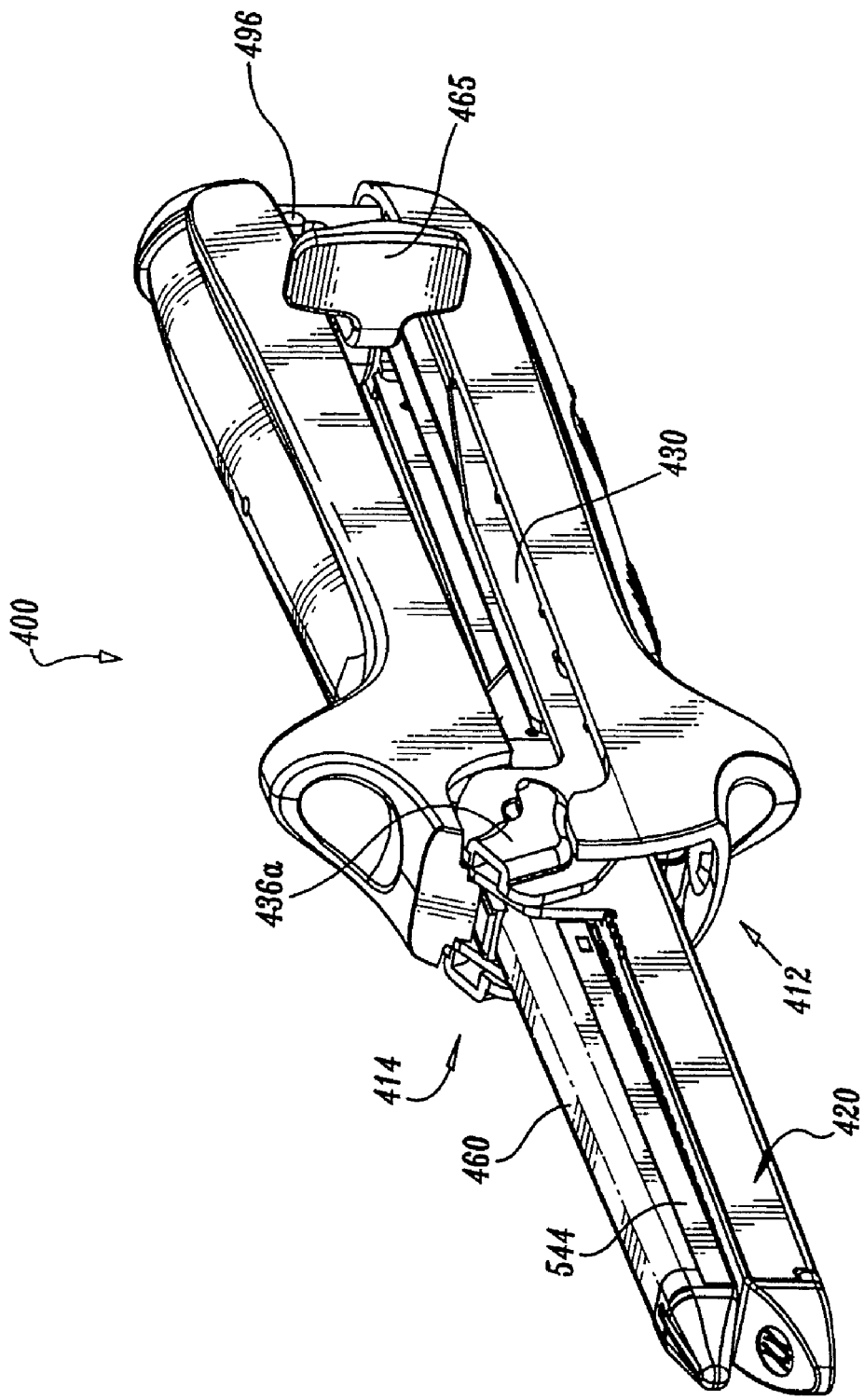
FIG. 50 is a perspective view of still another embodiment of a surgical fastener applying apparatus constructed in accordance with the present disclosure.
Figure 51:
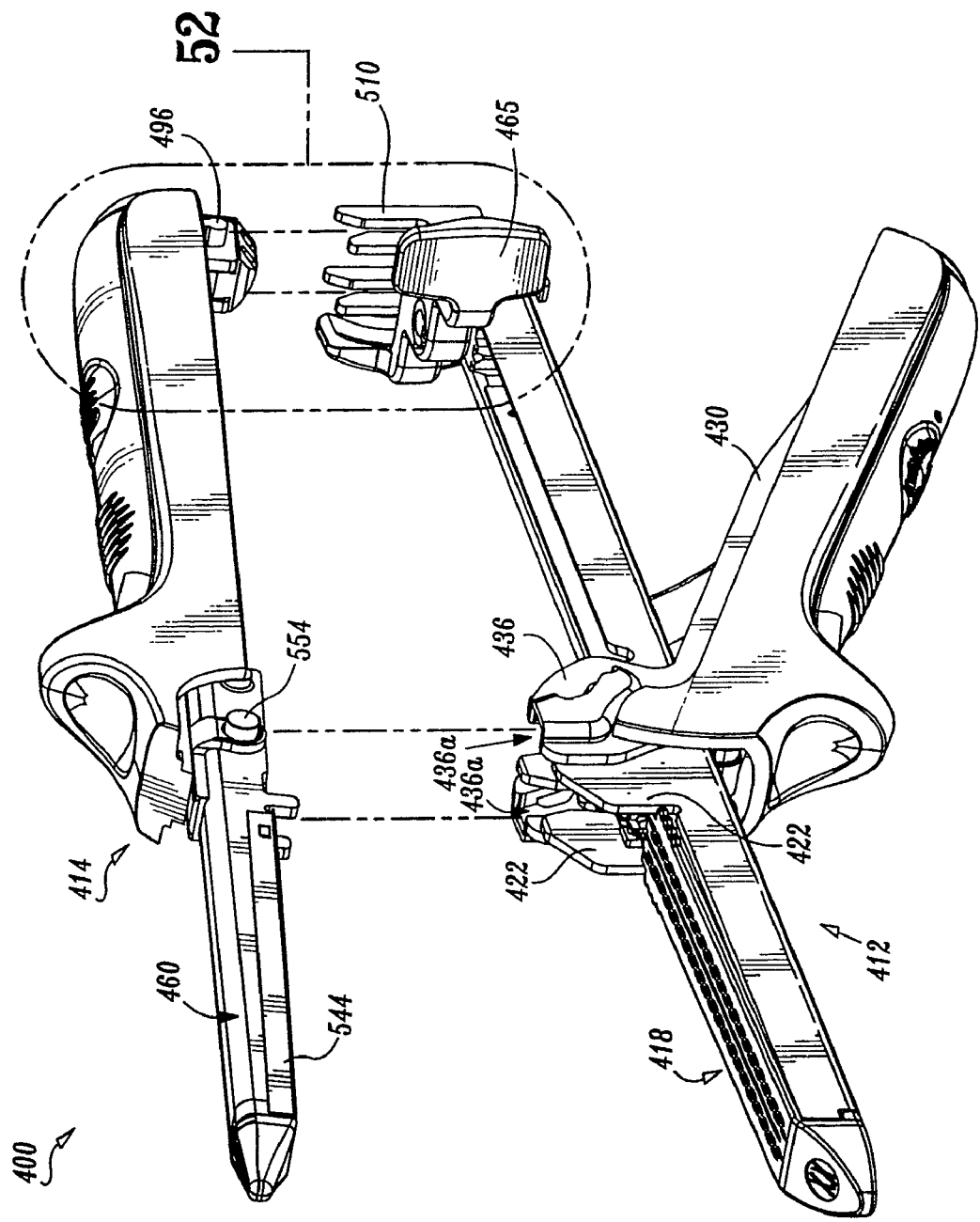
FIG. 51 is a perspective view of the surgical fastener applying apparatus of FIG. 50 opened from a cartridge receiving half-section side with a cartridge receiving half-section clamp lever opened.
Figure 52:
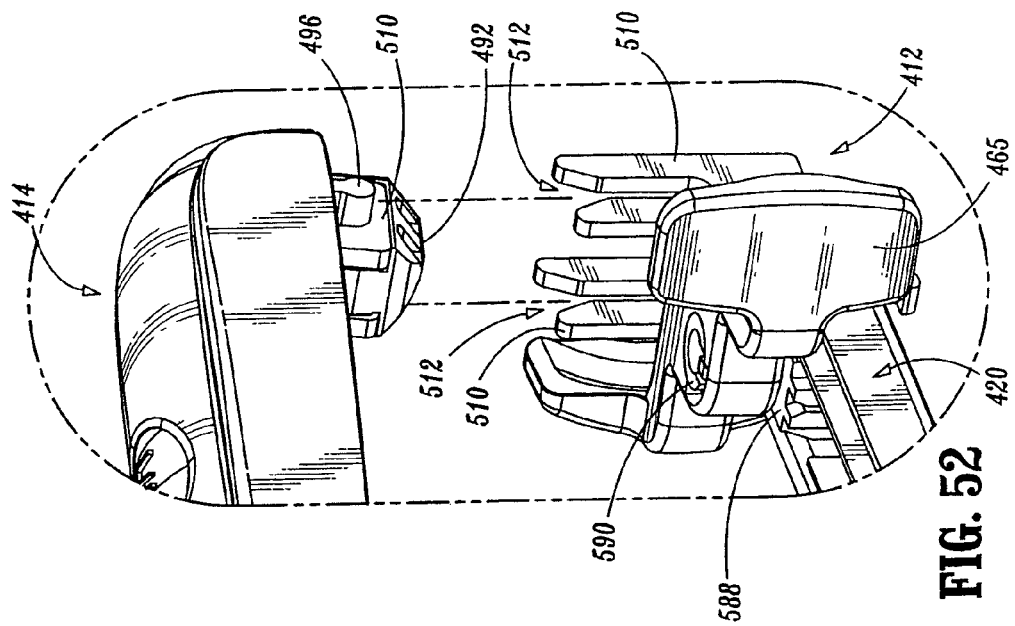
FIG. 52 is an enlarged perspective view of the indicated area of FIG. 51.
Figure 53:
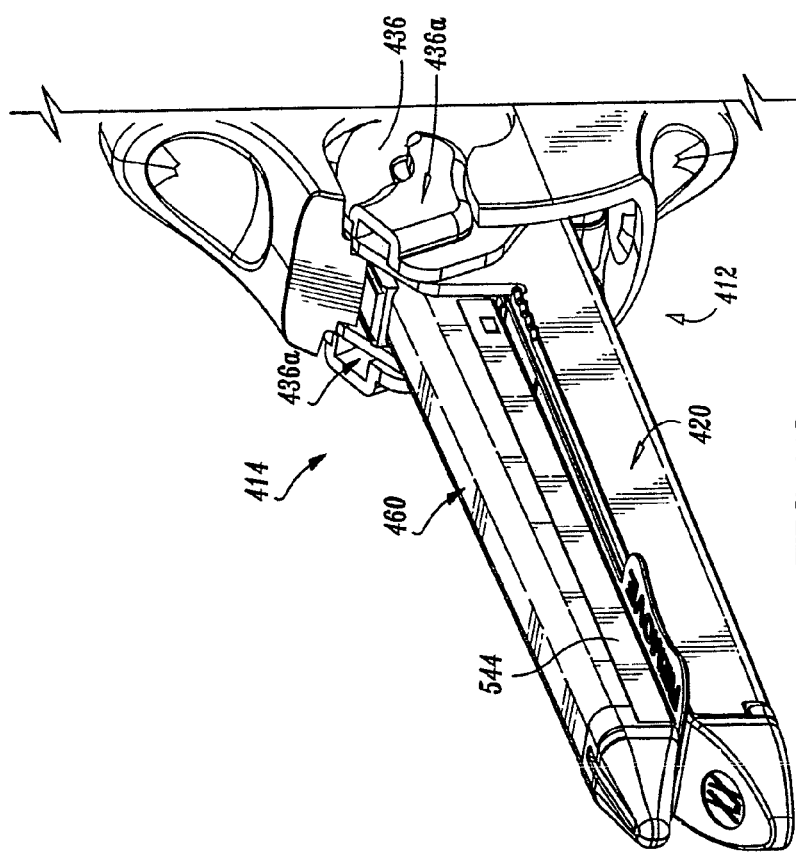
FIG. 53 is an enlarged perspective view of a distal end of the surgical fastener applying apparatus of FIG. 50.
Figures 101, 102:
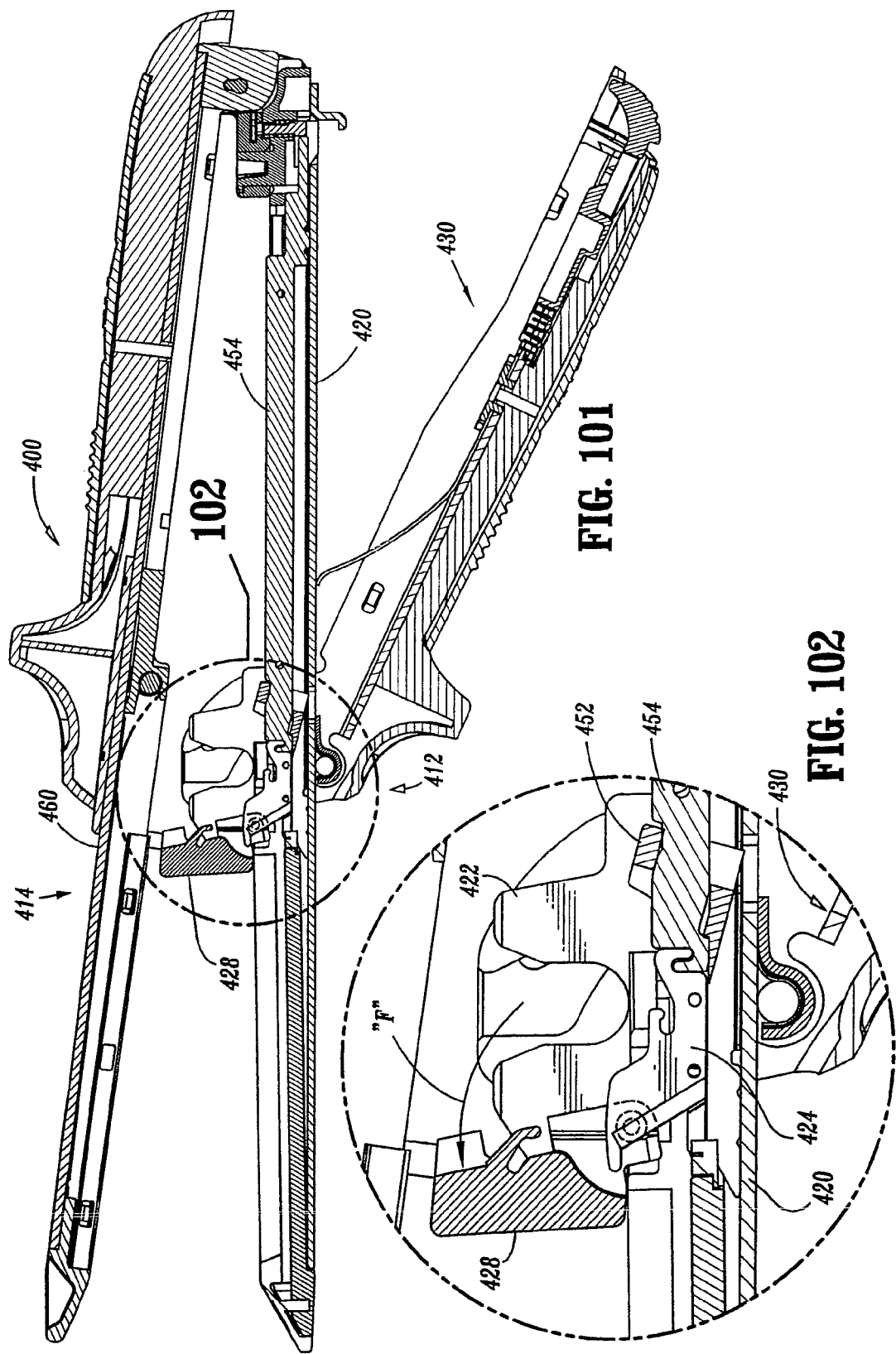
FIG. 101 is a cross-sectional view of the surgical fastener applying apparatus of FIG. 50, in an open post-firing condition, taken along the longitudinal axis.
FIG. 102 is an enlarged view of the individual area of detail of FIG. 101.

Turning now to FIGS. 50-102, another alternative embodiment of a surgical fastener applying apparatus is shown generally as 400. Apparatus 400 includes a cartridge receiving half-section 412, an anvil half-section 414 operatively coupled to cartridge receiving half-section 412, a cartridge assembly 416 configured and adapted to be removably mounted within a distal end of cartridge receiving half-section 412 and a firing slide 410 configured and adapted to be slidably received within cartridge receiving half-section 412. As seen in FIGS. 51-53, and as will be described in greater detail below, with cartridge receiving half-section clamping lever 430 in an open position, a proximal end of anvil half-section 414 is slidably and pivotably receivable at a proximal end of cartridge receiving half-section 412. Mounting bosses 554, projecting from anvil half-section 414, are slidably and pivotably receivable within an access channel 436a of or defined by cartridge receiving half-section clamping lever 430 in order to approximate a distal end of the cartridge receiving and anvil half-sections 412, 414.

Figure 56:
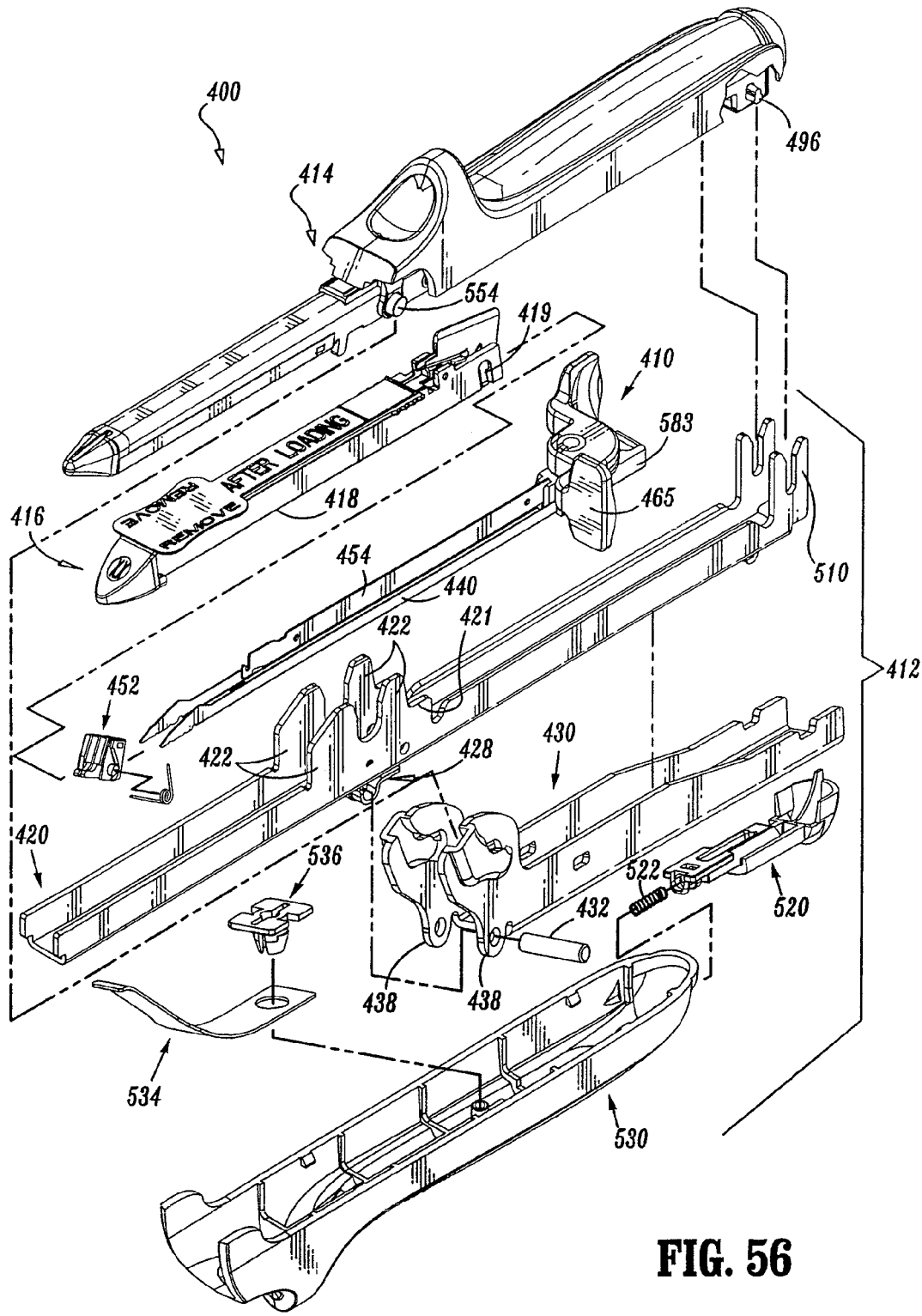
FIG. 56 is a perspective view, with parts separated, of the surgical fastener applying apparatus of FIG. 50.
Figure 66:
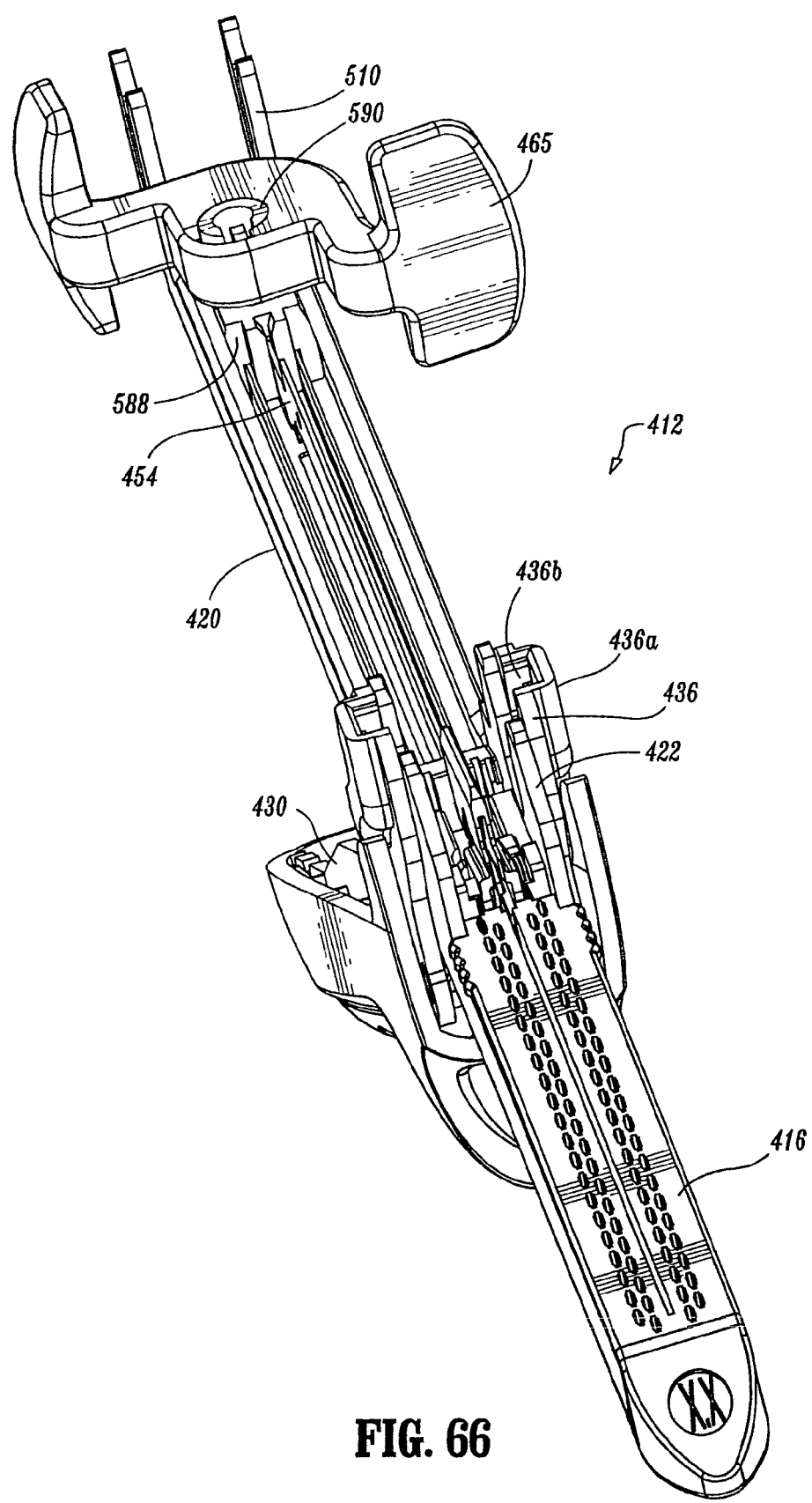
FIG. 66 is a top perspective view of the cartridge receiving half-section shown with the clamp lever in the open position.

Referring to FIGS. 56-65, and initially to FIGS. 56 and 57, anvil half-section 414 includes an anvil half-section channel member 460 having a distal end 460a and a proximal end 460b. Channel member 460 is substantially U-shaped and includes a pair of substantially parallel wall portions 462. Wall portions 462 preferably have a distal portion 462a having a height which is greater than a height of a proximal portion 462b thereof. Wall portions 462 preferably are provided with apertures 464 formed preferably near or at a mid portion of channel member 460, here shown as near the proximal end of distal portion 462a thereof, near the change in height from distal portion 462a to proximal portion 462b. Apertures 464 are configured and dimensioned to rotatably receive a gap adjustment cam 470 therein, as will be discussed in greater detail below.

Anvil half-section 414 is provided with an anvil plate 544 configured and dimensioned to be fit over wall portions 462 of distal portion 460a of anvil half-section 414. Anvil plate 544 includes a pair of anvil surfaces 546 having a plurality of anvil pockets 548 formed therein (see FIG. 61). Preferably, anvil pockets 548 are arranged in two pairs of longitudinal rows. Anvil plate 544 includes an anvil knife track 547 formed longitudinally therealong. Anvil knife track 547 interconnects and separates the pair of anvil surfaces 546 from one another. Anvil plate 544 includes a pair of upstanding side walls 549 extending upwardly from outside edges of anvil surfaces 546 (see FIGS. 57 and 61). Accordingly, when anvil plate 544 is mounted to distal portion 460a of anvil half-section 414, side walls 549 of anvil plate 544 are preferably disposed along the outside surface of distal wall portions 462a (see FIG. 61).

Anvil half-section 414 is further provided with a pair of longitudinally running anvil reinforcing ribs 540 disposed between wall portions 462 of distal portion 460a. It is envisioned that each reinforcing rib 540 is welded, along an upper edge 540a thereof, to a lower inside surface of distal portion 460a of channel member 460. Reinforcing ribs 540 are preferably welded within channel member 460 at a position such that reinforcing ribs 540 are disposed on either side of anvil knife track 547 (see FIG. 61). Reinforcing ribs 540 strengthen distal portion 460a of anvil half-section 414 thus reducing the tendency for distal portion 460a to deflect as a result of the stapling forces acting thereon. Reinforcing ribs 540 preferably have a length substantially equal to a length of distal portion 460a of anvil half-section 414. Each rib 540 is provided with an aperture 542 formed near a proximal end thereof. Preferably, apertures 542 of ribs 540 are in axial and transverse registration with apertures 464 formed in the distal portion 462a of wall portions 462.

Anvil half-section 414 includes a saddle element 550 fixedly secured thereon by welding, gluing, tacking, pinning or the like. Saddle element 550 includes a body portion 552 having a pair of proximal legs 552a and a pair of distal legs 552b extending therefrom. Preferably, each distal leg 552b includes a mounting boss 554 extending outwardly therefrom. Accordingly, when saddle element 550 is mounted onto anvil half-section 414, mounting bosses 554 are disposed or extend and/or project outwardly from the lateral surfaces of channel member 460. As will be described in greater detail below, mounting bosses 554 assist in the proper and complete operative coupling of cartridge receiving half-section 412 with anvil half-section 414.

Anvil half-section 414 includes a gap adjustment cam 470, (see FIG. 58), operatively disposed in apertures 464 formed in wall portions 462 of channel member 460. A cam is herein understood to be a structure having a periphery with at least two different points or areas along the periphery, with each point or area having a different radius from the rotational axis. Cams utilizable in accordance with the present disclosure can be any suitable shape (e.g., triangular, oblong, tear drop and the like).

As best seen in FIGS. 58, 58A and 58B, gap adjustment cam 470 preferably includes a cylindrical forward portion 472, cylindrical body portions 474 and a cylindrical rearward portion 476. Cylindrical body portions 474 of gap adjustment cam 470 have a central rotational axis "A" about which gap adjustment cam 470 rotates. Forward portion 472 and rearward portion 476 preferably share a common axis "B", spaced a distance "X" from central rotational axis "A" of body portions 474. Accordingly, as body portions 474 rotate about central rotational axis "A", forward and rearward portions 472, 476 act like cams to move one or more objects placed on or engaging forward and rearward portions 472, 476 through a maximum distance "2X". While rotation of gap adjustment cam 470 results in a maximum distance of displacement of "2X" it is envisioned that gap adjustment cam 470 can be dimensioned to cause a displacement of any distance upon full or partial rotation thereof.

While forward and rearward portions 472, 476 have been shown and described as cylinders, it is envisioned that forward and rearward portions 472, 476 can take on any other shape (e.g., an oval) which could define a camming surface and which other shape would determine the distance "X" through which the one or more objects placed on or engaging forward and rearward portions 472, 476 would move. For example, if the camming surface is not a cylinder, e.g., a teardrop shape, then the enlarged or cup portion of the teardrop shape would not be eccentric to axis "A".

As seen in FIGS. 58 and 58A, gap adjustment cam 470 includes a toothed annular channel 478 formed between body portions 474. Annular channel 478 preferably has a common central axis which is aligned with central axis "A" of body portions 474. Preferably, annular channel 478 has a diameter which is less than a diameter of body portions 474 such that teeth 480 of annular channel 478 lie below the surface of body portions 474. Preferably, at least one of forward and rearward portions 472, 476 is provided with a recess 482 formed in an end surface thereof. Recess 482 is preferably configured and adapted to complementarily receive a distal end of a rotational tool (not shown) therein. Accordingly, gap adjustment cam 470 can be rotated by a rotation of a rotational tool which is operatively received within recess 482.

Referring again to FIG. 57 and as seen in greater detail in FIGS. 59 and 61, forward portion 472 and rearward portion 476 of gap adjustment cam 470 are configured and dimensioned to project outwardly from apertures 464 formed in distal portion 462a of wall portions 462 of channel member 460. Preferably, body portion 474 of gap adjustment cam 470 is configured and dimensioned to be rotatably disposed within apertures 464. Accordingly, as will be described in greater detail below as seen in FIGS. 54, 55, 64 and 65, when surgical fastener applying apparatus 400 is assembled, forward portion 472 and rearward portion 476 of gap adjustment cam 470 rest atop a shoulder 421 of a respective hinge plate 422 extending from cartridge receiving half-section 412. In this manner, as gap adjustment cam 470 is rotated about common central axis "A" of body portions 474, forward and rearward portions 472, 476 press against shoulder 421 of hinge plate 422 as body portions 474 press against an upper surface of each aperture 464 formed in distal portion 462a of wall portions 462 thereby altering a relative spatial distance between a distal end portion of anvil half-section 414 and a distal end portion of cartridge receiving half-section 412.

Gap adjustment cam 470 provides surgical fastener applying apparatus 400 with a simple adjustment member whereby a spatial distance or gap "G" (see FIGS. 64 and 65), between a distal end of anvil half-section 414 and a distal end of cartridge receiving half-section 412, can be adjusted and set to an accurate predetermined distance regardless of the incoming tolerances or variations resulting from the manufacturing and/or assembly process of the individual components of surgical fastener applying apparatus 400. In other words, gap "G" can be set to a narrow tolerance due to the adjustability provided by gap adjustment cam 470 irrespective of whether the individual components of surgical fastener applying apparatus 400 are manufactured with a wide tolerance.

Gap "G" is measured between the upper face of the distal end portion of cartridge receiving half-section 412 and the lower face of the distal end portion of anvil half-section 414, preferably with cartridge assembly 416 and anvil plate 544 in place. By way of reference, the distal end portion is considered that portion of cartridge receiving half-section 412 and anvil half-section 414 which is distal of the hinge plates and that encompasses or includes the working longitudinal extent or portion of cartridge receiving half-section 412 and anvil half-section 414.

As shown in FIG. 57, anvil half-section 414 includes a gap adjustment cam lock 484. Gap adjustment cam lock 484 includes a body portion 486 configured and adapted to be mounted to or otherwise secured between wall portions 462 of anvil half-section channel member 460 and a distal end portion 488 configured and adapted to engage teeth 480 of toothed annular channel 478 of gap adjustment cam 470. Preferably, gap adjustment cam 470, including teeth 480, is made from a hard metal, such as, for example, stainless steel, while cam lock 484 is made from a pliable material, such as, for example, plastic. Accordingly, when cam lock 484 is pressed against teeth 480 of gap adjustment cam 470, teeth 480 dig into distal end portion 488 of cam lock 484 and prevent further rotation of gap adjustment cam 470. Alternately, distal end portion 488 includes at least one tooth 490 configured and dimensioned to snap-fit engage teeth 480 of toothed annular channel 478 of gap adjustment cam 470. Accordingly, tooth 490 of distal end portion 488 of cam lock 484 prevents gap adjustment cam 470 from freely rotating about common central axis "A". As such, gap adjustment cam 470 can be rotated to a plurality of discrete fixed positions corresponding to the positions of teeth 480 of toothed annular channel 478. Moreover, a toothed cam lock allows gap adjustment cam 470 to be readjusted after the assembly of surgical fastener applying apparatus 400.

Referring back to FIG. 57, anvil half-section 414 includes a proximal end cap 492 configured and dimensioned to be received between a pair of flanges 494 provided at proximal end 460b of anvil half-section 414 (see FIGS. 59 and 60). A shaped pivot-limiting pin 496 is provided therein which extends through elongated slots 498 formed in flanges 494 and through a correspondingly shaped hole 500 formed through distal end cap 492. As will be described in greater detail below, shaped pivot limiting pin 496 is substantially "pear or tear-drop shaped" and has a body portion 502, having a diameter, about which pin 496 rotates and an eccentric head portion 504, having a diameter less than the diameter of body portion 502, which extends radially outwardly from body portion 502 and which, when in slots 498 and hole 500, limits the range of rotation of pin 496 about a central axis of body portion 502.

Anvil half-section 414 further includes a distal end cap 506 configured and adapted to be snap-fit into the terminal end 509 of distal end 460*a* of anvil half-section 414. Preferably, distal end cap 506 is tapered in shape in order to facilitate insertion of distal end 460*a* of anvil half-section 414 into the target surgical site.

Figure 67:
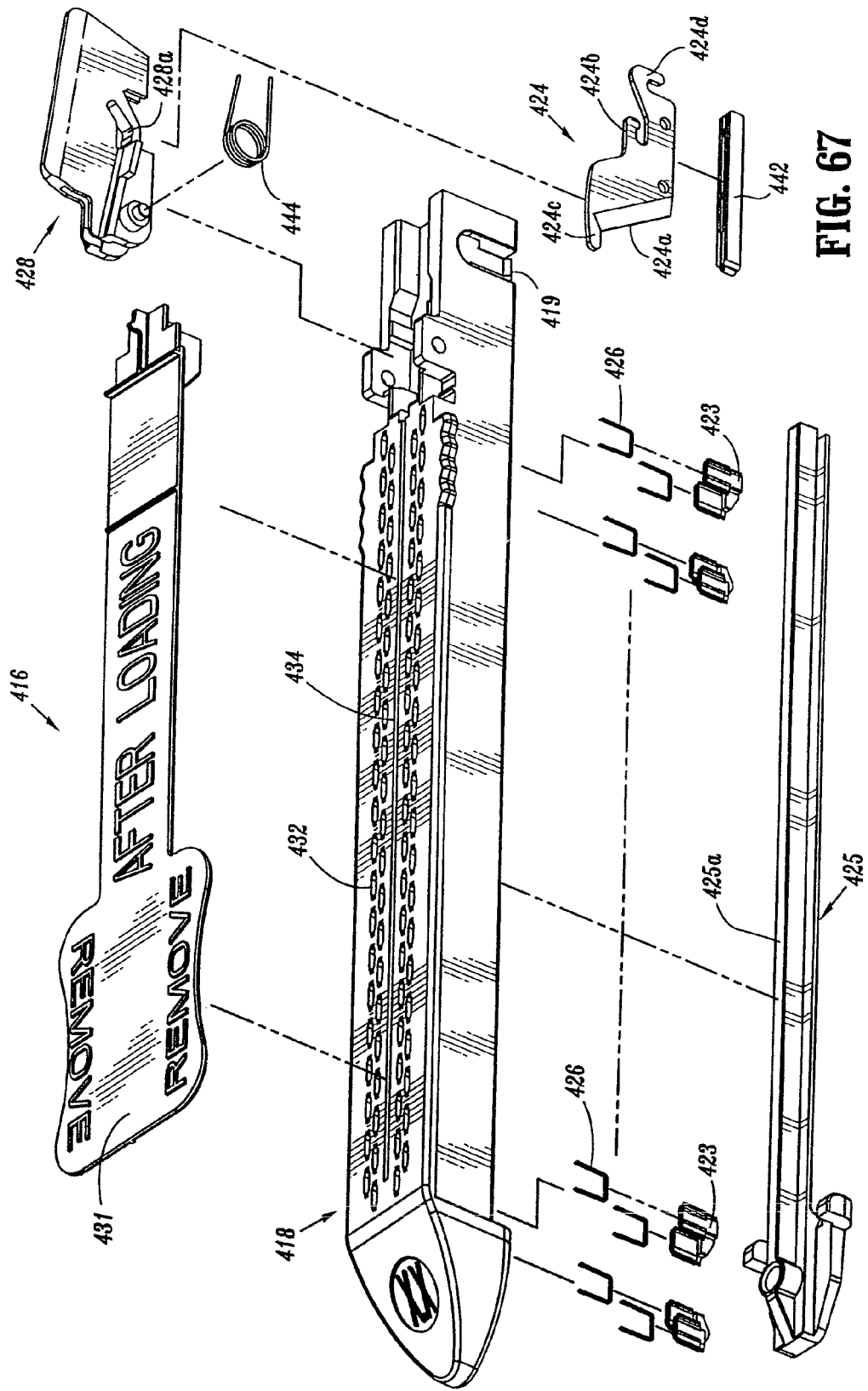
FIG. 67 is a perspective view, with parts separated, of the disposable staple cartridge assembly of the surgical stapler applying apparatus of FIG. 50.

With reference to FIG. 56 and also particularly to FIGS. 66-86, cartridge receiving half-section 412 of surgical fastener applying apparatus is shown and described. Cartridge receiving half-section 412 includes a removable and disposable staple cartridge assembly 416. Staple cartridge assembly 416 includes a cartridge body 418, a plurality of staple pushers attached to each other in groups of two offset oriented pusher pairs 423, a bottom cover 422, a knife 424, having an angled sharpened leading edge 424*a* and an atraumatic forward tip 424*c*, a plurality of staples 426, a pivotably mounted safety lockout 428 and a removable shipping wedge 431. As with known staple cartridge designs, cartridge body 418 has a plurality of rows of staple retaining slots 432 formed therein. As seen in FIG. 67, in this embodiment, there are two staggered rows of slots 432 formed on either side of a linear slotted track 434 which guides knife 424 during its longitudinal movement. A single staple 426 is positioned in each of slots 432.

As seen in FIG. 67, pusher pairs 423 are arranged in two series, one series on each side of slotted track 434, such that the center line of pusher pairs 423 of each series of pusher pairs 423 forms a line centered between the staggered rows of staples 426. The actuating surfaces of pusher pairs 423 act as cam followers and interact with a pair of staggered caroming surfaces 436 and 438 extending from a pair of cam bars 440 (see FIGS. 56, 69-70) to expel the pairs of staples 426 on each side of knife track 434. As illustrated, camming surfaces 436 and 438 form a single angle relative to horizontal as each cam bar 440 is moved distally. Cam bars 440 are moved distally until they are either stopped intentionally by the user to form less than all of staples 426, or until all of staples 426 are expelled from cartridge assembly 416.

As seen in FIG. 67, bottom cover 425 partially encloses the bottom of a channel formed by the upper surface and side walls of cartridge body 418. A longitudinal ridge 425*a* is formed on an upper surface of bottom cover 425 and serves as a bearing surface for knife bearing channel 442, which channel is secured to the bottom edge of knife 424, as knife travels in knife track 434. Knife bearing channel 442 which is preferably wider than knife track 434, is secured to the bottom surface of knife 424 such that knife bearing channel member 442 rides between knife track 434 and longitudinal ridge 425*a* of bottom cover 425. In this manner, knife 424 is prevented from undergoing substantial vertical movement during longitudinal translation in knife track 434.

Figure 68:
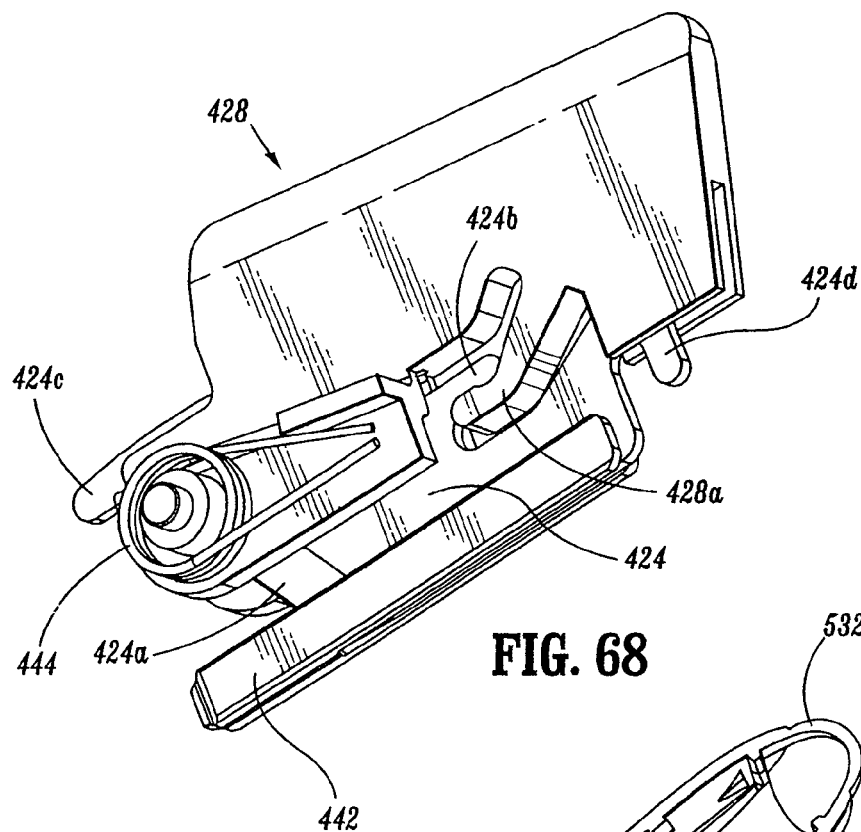
FIG. 68 is a perspective view, as seen from the bottom, of a safety lock out of an embodiment of the present disclosure.
Figure 82:
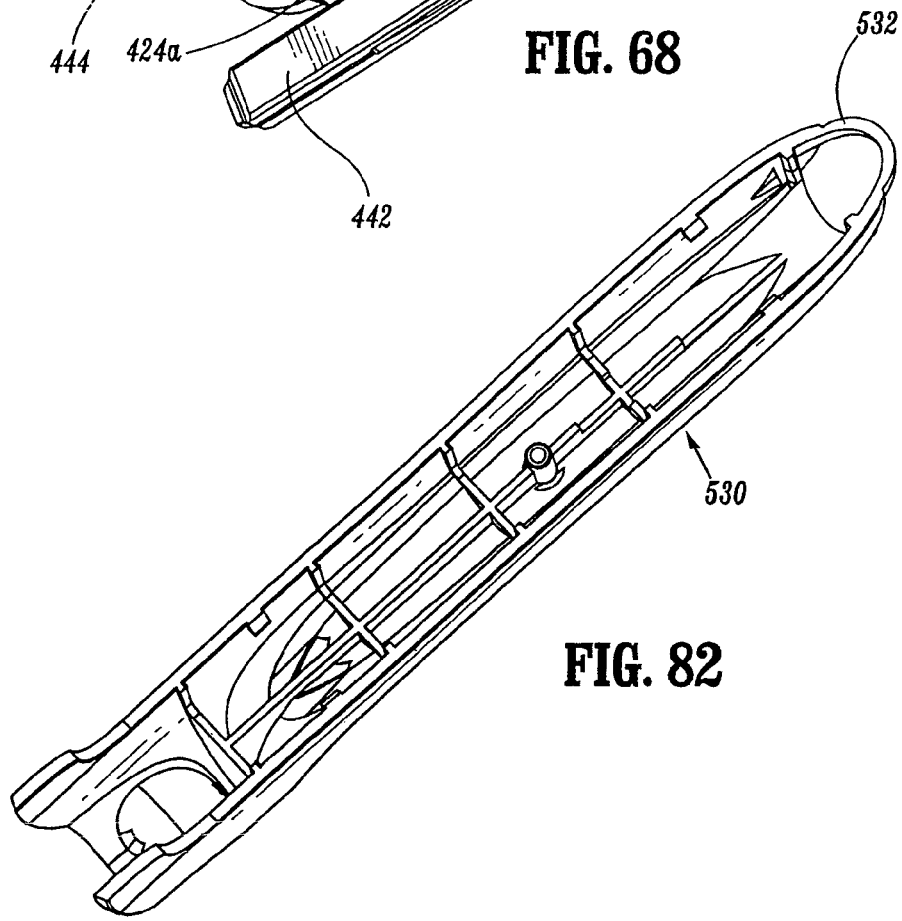
FIG. 82 is a perspective view of a handle cover for the cartridge lever of the surgical fastener applying apparatus of FIG. 50.

As seen in FIGS. 67 and 68, safety lockout 428 is pivotably disposed on the upper proximal end of cartridge body 418 and is movable from a locked orientation to an unlocked orientation. Preferably, safety lockout 428 is biased away from the locked orientation towards an orientation substantially perpendicular to the longitudinal axis of cartridge body 418. Any suitable biasing member may be utilized such as, for example, spring 444. To overcome the bias towards the perpendicular orientation, safety lockout 428 includes an upper transverse horizontal surface 428*a* (see FIGS. 67, 68, 76, 88, 93 and 98-102) extending from the underside thereof which engages the undersurface of a hook 424*b* formed on the upper edge surface of knife 424. This cooperative engagement serves to retain safety lockout 428 in the locked orientation when safety lockout 428 covers knife 424.

When surgical stapler 400 has been unclamped, as will be described in greater detail further herein, after either partial or complete firing, safety lockout 428 is biased to the perpendicular orientation (see FIGS. 99-102), extending upwardly away from cartridge receiving half-section 412. In this manner, safety lockout 428 prevents surgical stapler 400 from being re-clamped until the partial or completely fired cartridge assembly 416 is removed and replaced with a new cartridge assembly 416.

Similar to surgical stapler 100 of FIGS. 2-21, once surgical stapler 400 has been at least partially fired, and if the instrument is opened, safety lockout 428 of cartridge assembly 416 automatically moves to the perpendicular orientation due to the spring bias mounting thereof. With safety lockout 428 in this orientation, surgical stapler 400 cannot be re-clamped in order to continue or to complete the firing. Thus, if the user desires to apply further staples, the partially fired cartridge assembly 416 must first be removed and replaced with a new or non-fired cartridge assembly 416.

As previously described with reference to surgical fastener applying apparatus 100, shipping wedge 431 is removably attachable to cartridge body 418 and is configured and dimensioned to cover the entire surface area of staple rows 426 and knife track 434.

Referring to FIG. 76, a loading and lockout mechanism 451 for cartridge assembly 416 will now be described in detail. Loading and lockout mechanism 451 facilitates loading of cartridge assembly 416 and prevents firing of surgical stapler 400 until cartridge assembly 416 is properly loaded on cartridge receiving half-section 412 and surgical stapler 400 is properly clamped shut. Loading and lockout mechanism 451 includes a rocker 452 which rests atop cartridge receiving half-section 412. As seen in FIG. 76, rocker 452 preferably includes three slots, namely, open bottom slots 452*b*, 452*c* to permit longitudinal movement of cam bar channel 440 of firing slide 410 and a closed central slot 452*d* to permit passage of a knife actuating bar 454 therethrough.

Figures 88, 89:
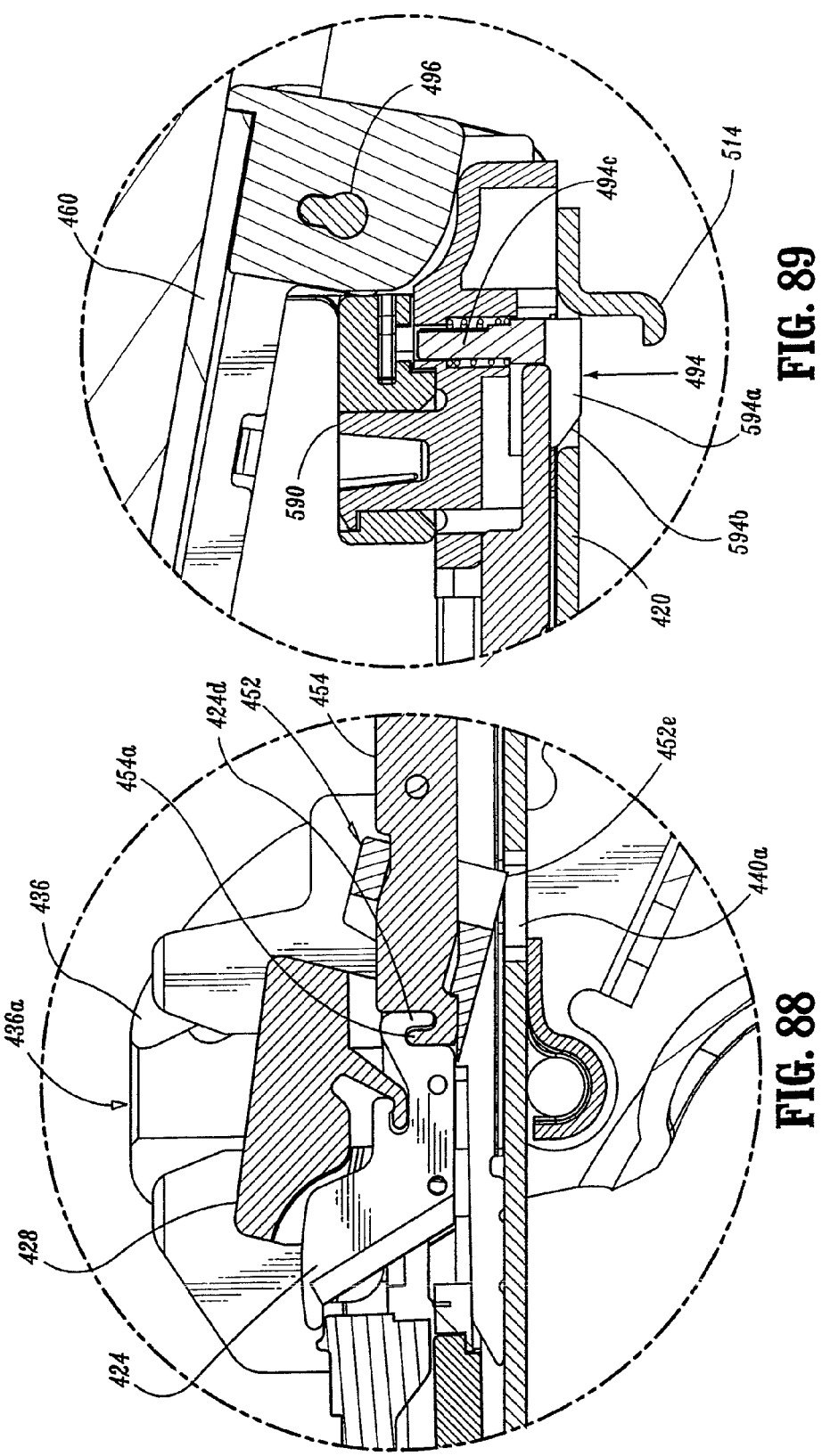
FIG. 88 is an enlarged view of the indicated area of detail of FIG. 87.
FIG. 89 is an enlarged view of the indicated area of detail of FIG. 87.

Rocker 452 of surgical fastener applying apparatus functions in the same manner as rocker 152 of surgical fastener applying apparatus 100. Rocker 452 is biased, by way of a spring 456 which is disposed on transversely extending post portions 452*a* and between a ridge 452*f* formed on a side of the rocker 452 and an upper surface of cartridge receiving half section 412, downwardly toward a locked-out position. When in the locked-out position, rocker 452 prevents cam bars 440 from distal longitudinal movement. In addition, when in the locked-out position, as seen in FIG. 88, a proximal edge surface 452*g* of rocker 452 engages a notch 454*a* formed in an upper edge of knife actuating bar 454 in order to prevent distal longitudinal movement of knife actuating bar 454. As best shown in FIG. 88, rocker 452 is further provided with a downwardly extending blocking surface 452*e* which is in vertical alignment with an opening 440*a* formed through the bottom surface of each cam bar 440 when each cam bar 440 is in its proximal-rest position Upon joining anvil half-section 414 with cartridge receiving half-section 412, as seen in FIGS. 76, 87, 88 and 93, rocker 452 is urged to rotate as indicated by arrow "D" in FIG.

93 by the lower surface of anvil half-section 414, and in particular cam lock 484, pressing against the upper surface of rocker 452. In this manner, proximal upper edge blocking surface 452g is moved out of (i.e., pivoted out of) engagement with notch 454a of knife actuating bar 454 thereby permitting a distal longitudinal movement of knife actuating bar 454 through slot 452d.

As seen in FIGS. 67 and 76, one of a pair of resilient friction fingers 419 is provided on either side of cartridge body 418 near a proximal end thereof. Friction fingers 419 are configured and adapted to project outwardly from cartridge body 418 and to frictionally engage the inner surface of distal side walls 420a (see FIG. 77) of cartridge receiving half-section channel member 420. In this manner, friction fingers 419 prevent cartridge assembly 416 from falling out of cartridge receiving half-section 412.

As seen in FIGS. 56 and 69-71, firing slide 410 includes a pair of camming surfaces 436, 438 extending from a pair of cam bars 440 which are joined to one another at a proximal end thereof, a knife actuating bar 454 positioned between the pair of cam bars 440, a slide block 588 operatively associated with the proximal end of the pair of cam bars 440, and a firing lever 465 pivotably coupled to slide block 588. Firing lever 465 provides the user with the ability to fire surgical fastener applying apparatus 400 from either the left or the right side. As seen in FIG. 70 and in greater detail in FIG. 88, knife actuating bar 454 includes a hook 454a formed at a distal end thereof. Hook 454a of knife actuating bar 454 is configured and adapted to engage a hook 424d formed at the proximal end of knife 424. In this manner, as knife actuating bar 454 is displaced proximally and distally, so to is knife 424.

Slide block 588 includes a hub 590 projecting therefrom and configured and adapted to be snap-fit into a pivot hole 592 formed in lever 465. Slide block 588 further includes a pedal 594 reciprocally received with a hole 596 formed in slide block 588. As seen in FIG. 71, pedal 594 includes a split body portion 594a, configured and adapted to straddle a proximal end of knife actuating bar 454, and a pin 594c extending upwardly therefrom. Preferably, body portion 594a includes an angled distal surface 594b. Preferably, pin 594c is configured and dimensioned to extend completely through hole 596 of slide block 588. As seen in FIG. 70, a compression spring 598 is disposed about pin 594c and between split body portion 594a of pedal 594 and slide block 588. In this manner, pedal 594 is biased away from slide block 588.

As seen in FIGS. 74 and 75, firing lever 465 includes an arcuate recess 465a formed in a bottom surface thereof. Arcuate recess 465a defines the range of rotation through which firing slide 465 can pivot about hub 590 of slide block 588. Firing lever 465 further includes a stop recess 465b formed at each end of arcuate recess 465a. As will be described in greater detail below, stop recesses 465b are configured and dimensioned to receive a distal end of pin 594c of pedal 594 therein in order to prevent firing lever 465 from pivoting about hub 590 during a firing stroke of surgical fastener applying apparatus 400.

Turning to FIGS. 56 and 76-86, cartridge receiving half-section 412 of surgical fastener applying apparatus 400 includes a cartridge receiving half-section channel member 420, a cartridge receiving half-section lever 430 pivotably coupled to channel 420, a cartridge lever release member 520 (see FIG. 85) operatively coupled to a proximal end of cartridge lever 430, and a contoured cartridge lever cover 530 configured and adapted to snap-fit over cartridge lever 430.

As seen in FIGS. 77 and 78, cartridge receiving half-section channel member 420 includes a pair of juxtaposed hinge plates 422 extending upwardly from the sides thereof. Preferably, hinge plates 422 are spaced a distance apart sufficient to permit anvil half-section channel member 460 to be received therebetween. Turning momentarily back to FIG. 51, each hinge plate 422 includes a substantially U-shaped slot 424 formed through an upper edge thereof for permitting receipt of a respective mounting nub or boss 554 of saddle element 550 therein. Each hinge plate 422 further includes a shoulder 426 formed at a proximal end thereof. Shoulders 426 define a substantially planar horizontal surface 426a on which forward and rearward portions 472, 476 of gap adjustment cam 470 rests (see FIGS. 64 and 65).

A pivot bracket 428 is secured to a bottom surface of cartridge receiving half-section channel member 420. Pivot bracket 428 includes an annular portion 428a configured and adapted to receive a pivot pin 432 therethrough (see FIG. 56).

Cartridge receiving half-section channel member 420 further includes a pair of juxtaposed pivot plates 510 extending upwardly from a proximal end thereof. Each pivot plate 510 is provided with a pivot pin receiving slot 512 for receiving shaped pivot limiting pin 496 of anvil half-section 414 therein (see FIG. 52). As seen in FIG. 78, cartridge receiving half-section channel member 420 further includes a cartridge lever latch 514 formed at a proximal end thereof.

Turning now to FIGS. 83 and 84, clamping lever 430 includes a body portion 434 having a pair of juxtaposed hinge plates 436 extending upwardly from a distal end thereof and a pair of juxtaposed pin receiving brackets 438 extending downwardly from a, distal end thereof. Each pin receiving bracket 438 is provided with a pin receiving hole 438a formed therein for receiving the ends of pivot pin 432 (see FIG. 56) therein.

Each hinge plate 436 is provided with an access channel 436a formed therein. A portion of one channel cover for an access channel 436a is shown broken away. Preferably, each access channel 436a has a first portion 436b which is oriented substantially vertically when clamping lever 430 is in an open position (see FIG. 51) and a second portion 436c which is oriented substantially horizontally when clamping lever 430 is being moved to and is in a closed position (see FIGS. 64 and 65). Each access channel 436a is configured and adapted to slidably receive a respective mounting boss 554 of saddle 550 therein, which mounting bosses 554 extend and project from the lateral surface of anvil half-section channel member 460 a distance sufficient to engage each access channel 436a and have a cross-sectional dimension enabling it to be received within each access channel 436a. Preferably, access channels 436a are covered in order to prevent tissue from being trapped within access channels 436a and in order to provide additional strength to each hinge plate 436.

As seen in FIGS. 56 and 81, cartridge lever release member 520 is spring biased proximally toward a lateral position via a spring member 522 and is provided with a catch 524 (see FIGS. 81 and 90) for engaging cartridge lever latch 514 (see FIG. 94) formed at the proximal end of cartridge receiving half-section channel member 420. In order to release cartridge lever latch 514, the user presses release member 520 in a distal direction, thereby disengaging catch 524 from latch 514.

Figure 85:
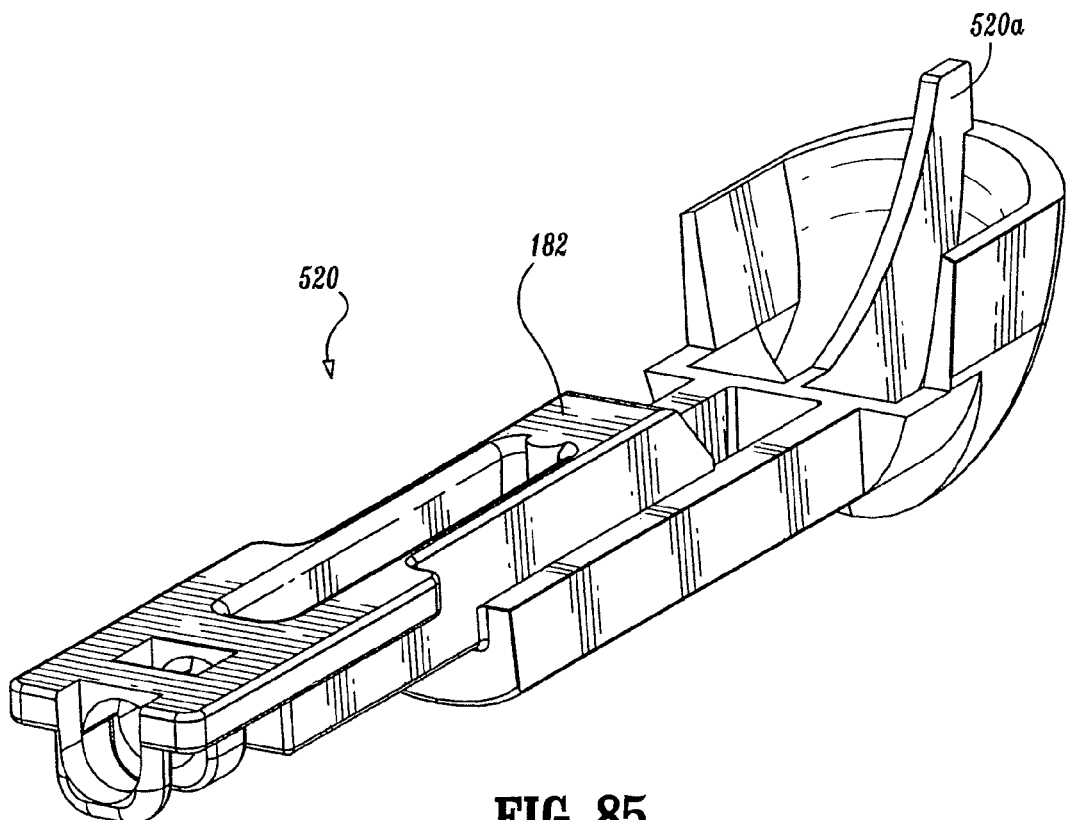
FIG. 85 is a perspective view of a cartridge lever release member.
Figure 86:
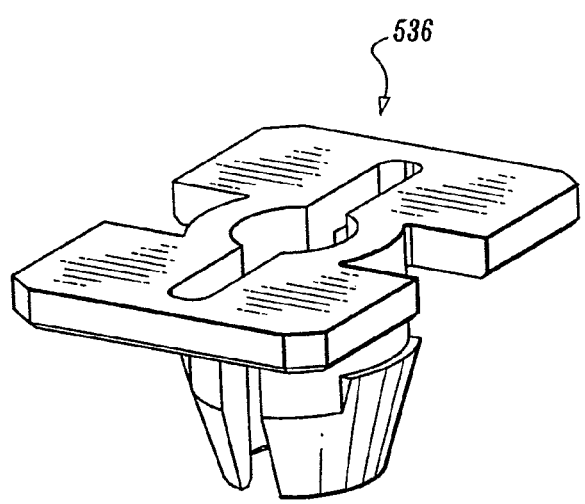
FIG. 86 is a perspective view of a leaf spring mounting plug of the surgical fastener applying apparatus of FIG. 50.

In order to prevent inadvertent opening of clamping lever 430, as seen in FIGS. 81 and 85, release member 520 is provided with a projection 520a extending downwardly from a proximal end thereof, which projection 520a is seated within a guard 532 formed at a proximal end of cartridge lever cover 530.

Cartridge receiving half-section 412 is further provided with a leaf spring 534 as seen in FIGS. 56 and 79, having a proximal end 534a secured to an inside of clamping lever 430, via a post member 536, and a free distal end 534*b* contacting a bottom surface of cartridge receiving half-section channel member 420. In this manner, clamping lever 430 is spring biased away from cartridge receiving half-section channel member 420.

With reference to FIGS. 64-65 and 87-102, use and operation of surgical fastener applying apparatus 400 is shown and described. Initially, with reference to FIGS. 64 and 65, after assembly of most, if not at all of the individual components of surgical fastener applying apparatus 400, gap "G" can be set (see FIG. 65). According to one method of setting gap "G", a gauging element, such as, for example, a feeler gauge, (not shown) having a predetermined fixed thickness is inserted into gap "G" between the distal ends of cartridge receiving half-section 412 and anvil half-section 414, preferably between tissue contacting surfaces of cartridge assembly 416 and of anvil 544. Gap adjustment cam 470 is fixed or rotated and fixed, causing cartridge receiving half-section 412 and/or anvil half-section 414 to displace relative to one another, until gap "G" is set to the predetermined thickness of the gauging element. Gap adjustment cam 470 is adjusted until cartridge receiving half-section 412 and anvil half-section 414 contact the gauging element. As seen in FIG. 65, rotation of gap adjustment cam 470, as indicated by arrow "C" results in rotation of, for example, anvil receiving half-section 414, about pivot point "Y" (i.e., mounting bosses 554), in the direction indicated by arrow "$C_l$". Accordingly, gap "G" will be narrower at the distal tip and will become progressively wider from the distal tip towards hinge plates 422, such that in the loaded condition, with tissue present, deflection will occur at the tip to create a more uniform gap along the overall distal portion of surgical fastener applying apparatus 400.

Once the position of gap adjustment cam 470 is fixed or set, gap adjustment cam 470 is fixedly held in position by cam lock 484 such that further rotation of gap adjustment cam 470 is prevented. While the adjustment and the setting of gap "G" is a step which preferably takes place during the manufacture and assembly of surgical fastener applying apparatus 400, it is envisioned that the adjustment and setting of gap "G" can take place post manufacturing and assembly, including by a user, but preferably prior to packaging or use of the stapler. Other suitable means and methods for adjusting gap "G" can be employed at the same time or other times during or as part of the manufacturing or assembly process. It is envisioned that adjustment of the size of gap "G", such as, for example, during the manufacturing and assembly process, allows for the manufacture of surgical fastener applying apparatus which can be set to varying predetermined gap sizes in order to accommodate cartridge assemblies having different length staples therein. In other words, if a cartridge assembly having relatively shorter length staples is to be used, the gap can be set to a narrower dimension. Alternatively, if a cartridge assembly having relatively longer length staples is to be used, the gap can be set to a larger dimension.

Figure 87:
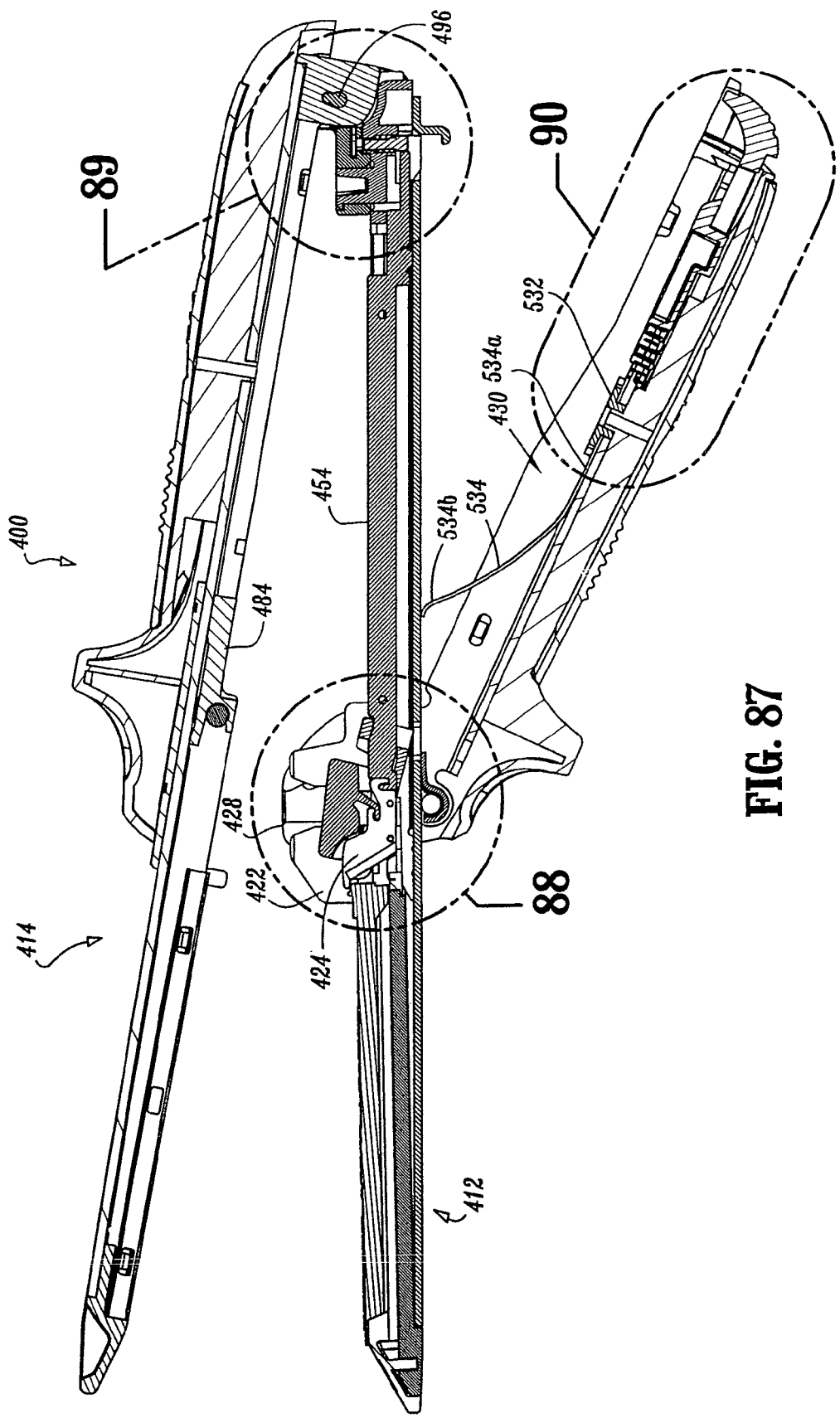
FIG. 87 is a cross-sectional view of the surgical fastener applying apparatus, taken along the longitudinal axis, depicting the coupling of the cartridge receiving half-section to the anvil half-section.

One method or sequence of coupling and closure of cartridge receiving half-section 412 with anvil half-section 414 is best seen in FIGS. 87-91. With cartridge lever 430 in an open position, as seen in FIGS. 51, 52 and 87, the proximal ends of half-section 412, 414 are approximated toward one another such that pivot limiting pin 496 of anvil half-section 414 rests within pivot pin receiving slots 512 of pivot plates 510 of cartridge receiving half-section 412. As best seen in FIG. 91, the shape of pivot limiting pin 496 limits the longitudinal angle (i.e., the angle between cartridge receiving half-section 412 and anvil half-section 414) at which anvil half-section 414 can be coupled with cartridge receiving half-section 412 to an angle "α". Preferably, angle "α" is about 15°. With the proximal ends of half-section 412, 414 coupled to one another, the distal ends of half-section 412, 414 are approximated towards one another until mounting bosses 554, projecting from anvil half-section 414, are received within first portion 436*b* of access channels 436*a* formed on clamping lever 430. Alternatively, the distal ends or mid portions of half-sections 412, 414 can be coupled to one another before the proximal ends are joined to one another. It is also further envisioned that the proximal and distal ends of half-sections 412, 414 can be simultaneously coupled to one another.

With mounting bosses 554 positioned within access channels 436*a* of cartridge lever 430 (see FIGS. 51, 64 and 65), the proximal end of clamping lever 430 is approximated toward cartridge receiving half-section 412 until catch 524 of release member 520 engages latch 514 of cartridge receiving half-section channel member 420 (see FIG. 94). By approximating clamping lever 430 toward cartridge receiving half-section 412, mounting bosses 554 are advanced through access channels 436*a* (i.e., from first portion 436*b* to second portion 436*c*, as seen in FIG. 64) thereby completing the approximation of cartridge receiving half-section 412 with anvil half-section 414, as a result of the caroming action taking place therebetween.

Figure 92:
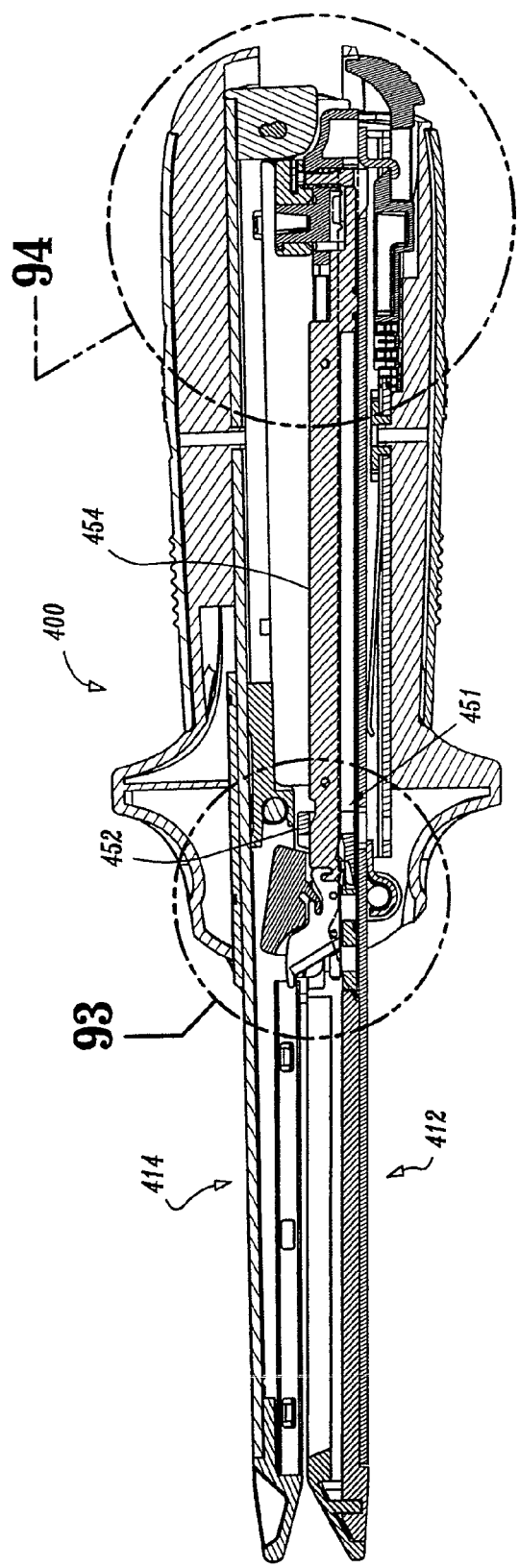
FIG. 92 is a cross-sectional view, taken along the longitudinal axis, of the surgical fastener applying apparatus of FIG. 50, in a closed pre-firing condition.

As seen in FIGS. 92-94, complete approximation of half-sections 412, 414 to one another results in the disengagement of rocker 452 from firing slide 410, including cam bar 440 and knife actuating bar 454, as evidenced by arrow "D" in FIG. 93. In particular, proximal edge surface 452*g* of rocker 452 disengages notch 454*a* of knife actuating bar 454 and blocking surface 452*e* disengages opening 440*a* formed in cam bar 440. With rocker 452 disengaged from knife actuating bar 454 and cam bar 440, the user is now able to fire surgical fastener applying apparatus 400 by driving firing slide 410 distally.

Figure 98:
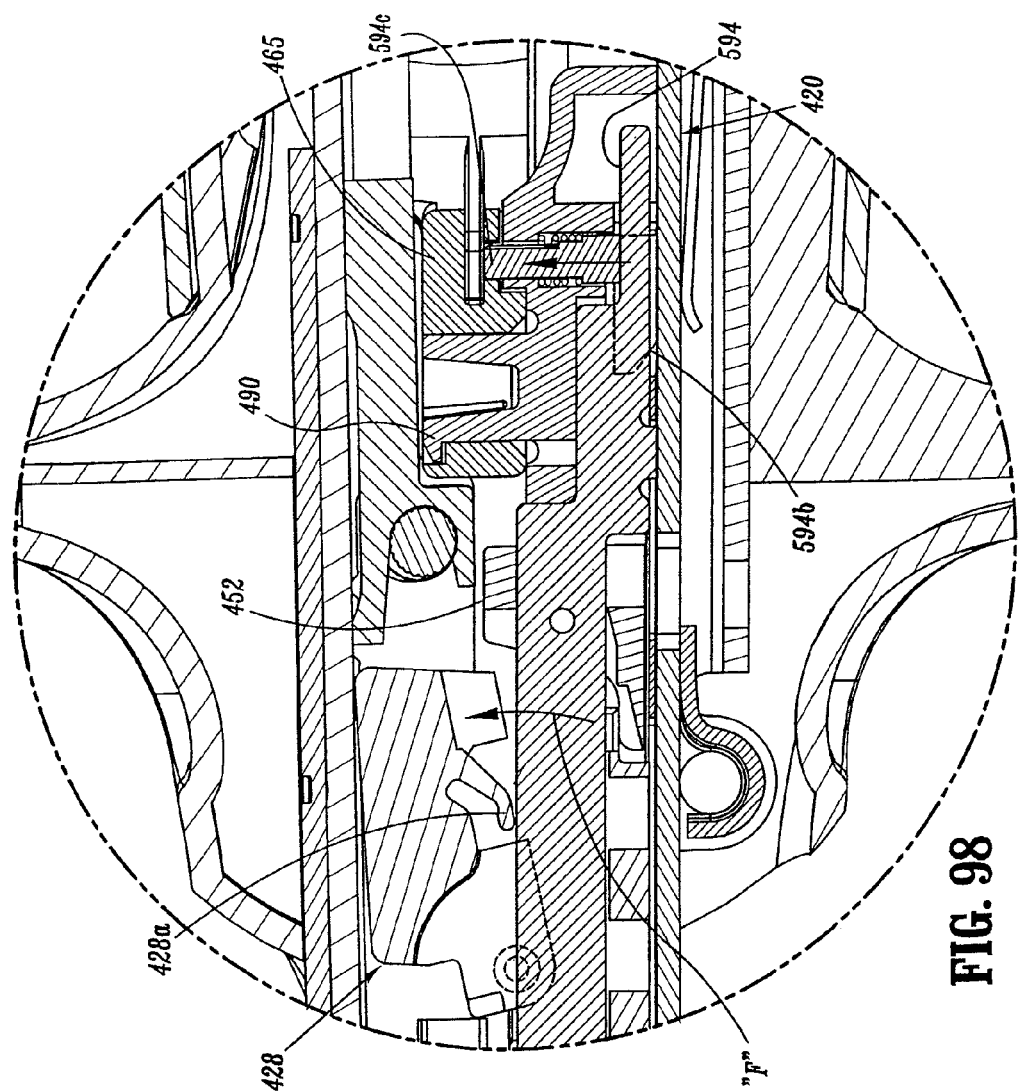
FIG. 98 is an enlarged view of the indicated area of detail of FIG. 96.
Figure 97:
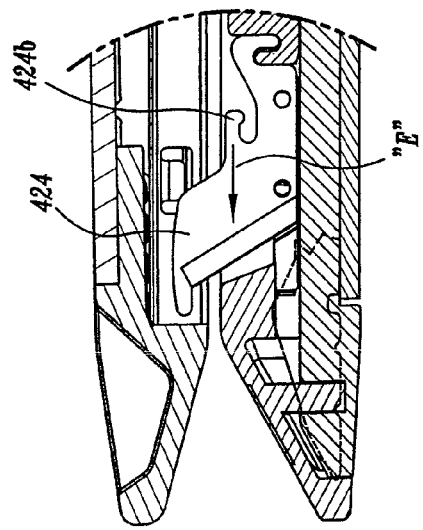
FIG. 97 is an enlarged view of the indicated area of detail of FIG. 96.

Firing slide 410 is driven distally by advancing firing lever 465 in a distal direction, as indicated by arrow "E" of FIG. 95. As seen in FIGS. 94 and 98, distal advancement of firing lever 465 results in pedal 594 rising up due to the camming action of angled distal surface 594*b* of body portion 594*a* against cartridge receiving half-section channel member 420. In so doing, the distal end of pin 594*c* is received in a stop recess 465*b* (see FIGS. 74 and 75) of firing lever 465 in order to prevent firing lever 465 from rotating about hub 590 of slide block 588.

As seen in FIGS. 93 and 98, distal advancement of firing slide 410 also results in the disengagement of transverse horizontal surface 428*a* of safety lockout 428 from hook 424*b* formed on the upper edge surface of knife 424. Accordingly, when surgical fastener applying apparatus 400 is unclamped, after either partial or complete firing, safety lockout 428 is biased to the perpendicular orientation (see FIGS. 99-102), extending upwardly away from cartridge receiving half-section 412. In this manner, safety lockout 428 prevents surgical fastener applying apparatus 400 from being re-clamped until partial or completely fired cartridge assembly 416 is removed and replaced with a new cartridge assembly 416.

It is envisioned that any of the surgical fastener applying apparatus disclosed herein can be configured and adapted to receive a staple cartridge loaded with a plurality of directionally biased staples and/or specially configured axial pockets as disclosed in commonly assigned U.S. patent application Ser. No. 09/972,594, filed Oct. 5, 2001 which is a Continuation-in-Part application of U.S. Ser. No. 09/693,379, field Oct. 20, 2000, both of which are entitled "Directionally Biased Staple and Method of Manufacture", the entire contents of each of which are incorporated herein by reference.

It will be understood that various modifications may be made to the embodiments of the surgical fastener applying apparatus disclosed herein. Therefore, the above description should not be construed as limiting, but merely as exemplifications of preferred embodiments. Those skilled in the art will envision other modifications within the scope and spirit of the present disclosure.

What is claimed is:

1. A surgical fastener applying apparatus comprising:
   an anvil half-section having a proximal end portion and a distal end portion including an anvil which defines a fastener forming surface against which surgical fasteners are driven;
   a cartridge receiving half-section having a proximal end portion and a distal end portion, the cartridge receiving half-section being configured and adapted to releasably mate with the anvil half-section, the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position, the anvil half-section and the cartridge half-section defining a gap between their respective distal ends when in the fully clamped position;
   a gap adjustment mechanism disposed between the anvil half-section and the cartridge receiving half-section and configured and adapted to vary the size of the gap between the distal end portions of the anvil half-section and the cartridge receiving half-section, wherein the gap adjustment mechanism defines an axis of rotation that is transverse to a longitudinal axis of surgical fastener applying apparatus, and wherein the gap adjustment mechanism is rotated to adjust the gap; and
   a cam lock configured and adapted to engage the gap adjustment mechanism and to prevent movement of the gap adjustment mechanism after adjustment of the gap.

2. The surgical fastener applying apparatus according to claim 1, wherein the gap adjustment mechanism includes a cam positioned between the anvil half-section and the cartridge receiving half-section when in the assembled condition, wherein manipulation of the cam results in the variation of the size of the gap between the distal ends of the anvil half-section and the cartridge receiving half-section.

3. The surgical fastener applying apparatus according to claim 1, further comprising:
   a clamp latch configured and adapted to retain said clamping lever in a clamped orientation; and
   a safety interlock assembly configured and adapted to prevent opening of said clamping lever after said firing lever has been moved distally.

4. A surgical fastener applying apparatus comprising:
   an anvil half-section having a proximal end portion and a distal end portion including an anvil which defines a fastener forming surface against which surgical fasteners are driven;
   a cartridge receiving half-section having a proximal end portion and a distal end portion, the cartridge receiving half-section being configured and adapted to releasably mate with the anvil half-section, the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position. the anvil half-section and the cartridge half-section defining a gap between their respective distal ends when in the fully clamped position;
   a gap adjustment mechanism disposed between the anvil half-section and the cartridge receiving half-section and configured and adapted to vary the size of the gap between the distal end portions of the anvil half-section and the cartridge receiving half-section, wherein the gap adjustment mechanism includes a cam with a forward portion, a body portion and a rearward portion, wherein the body portion of the cam defines a central rotational axis and wherein the forward and rearward portions share a common axis which is spaced a distance from the central rotational axis; and
   a cam lock configured and adapted to engage the gap adjustment mechanism and to prevent movement of the gap adjustment mechanism after adjustment of the gap.

5. The surgical fastener applying apparatus according to claim 4, wherein the body portion of the gap adjustment mechanism is rotationally disposed within apertures formed in the anvil half section.

6. The surgical fastener applying apparatus according to claim 5, wherein the forward and rearward portions rest against respective surfaces of the cartridge receiving half-section.

7. A surgical fastener applying apparatus comprising:
   an anvil half-section having a proximal end portion and a distal end portion including an anvil which defines a fastener forming surface against which surgical fasteners are driven, the anvil half-section including a clamping lever;
   a cartridge receiving half-section having a proximal end portion and a distal end portion, the cartridge receiving half-section being configured and adapted to releasably mate with the anvil half-section. the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position, the anvil half-section and the cartridge half-section defining a gap between their respective distal ends when in the fully clamped position;
   a gap adjustment mechanism disposed between the anvil half-section and the cartridge receiving half-section and configured and adapted to vary the size of the gap between the distal end portions of the anvil half-section and the cartridge receiving half-section; and
   a cam lock configured and adapted to engage the gap adjustment mechanism and to prevent movement of the gap adjustment mechanism after adjustment of the gap;
   the cartridge half-section clamping lever and the anvil half-section clamping lever being configured and adapted for operative movement to enable opening of the applying apparatus on either said cartridge half-section side or said anvil half-section side.

8. A surgical fastener applying apparatus comprising:
   an anvil half-section having a proximal end portion and a distal end portion including an anvil which defines a fastener forming surface against which surgical fasteners are driven;
   a cartridge receiving half-section having a proximal end portion and a distal end portion, the cartridge receiving half-section being configured and adapted to releasably mate with the anvil half-section, the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position, the anvil half-section and the cartridge half-section defining a gap between their respective distal ends when in the fully clamped position;

a gap adjustment mechanism disposed between the anvil half-section and the cartridge receiving half-section and configured and adapted to vary the size of the gap between the distal end portions of the anvil half-section and the cartridge receiving half-section;

a cam lock configured and adapted to engage the gap adjustment mechanism and to prevent movement of the gap adjustment mechanism after adjustment of the gap; and a loading unit having staples and being receivable in the cartridge half-section and wherein the cartridge half-section includes a member longitudinally movable through the loading unit to fire staples from the loading unit, and a lockout mechanism arranged to prevent advancement of the member in a locked-out position of the lockout mechanism, the lockout mechanism including a rocker pivotably mounted to the cartridge half-section.

9. A surgical fastener applying apparatus comprising:

an anvil half-section having a proximal end portion and a distal end portion including an anvil which defines a fastener forming surface against which surgical fasteners are driven;

a cartridge receiving half-section having a proximal end portion and a distal end portion, the cartridge receiving half-section being configured and adapted to releasably mate with the anvil half-section, the anvil half-section and the cartridge receiving half-section being relatively movable from an unclamped position to a fully clamped position to clamp tissue therebetween, the cartridge half-section including a pivotable clamping lever, wherein movement of the clamping lever from a first position to a second position moves the cartridge receiving and anvil half-sections to the fully clamped position, the anvil half-section and the cartridge half-section defining a gap between their respective distal ends when in the fully clamped position;

a gap adjustment mechanism disposed between the anvil half-section and the cartridge receiving half-section and configured and adapted to vary the size of the gap between the distal end portions of the anvil half-section and the cartridge receiving half-section;

a cam lock configured and adapted to engage the gap adjustment mechanism and to prevent movement of the gap adjustment mechanism after adjustment of the gap; and a loading unit having staples and being receivable in the cartridge half-section, the loading unit having a lockout movable from a initial substantially horizontal position to a vertical blocking position, the blocking position preventing re-clamping of the cartridge half-section and anvil half-section after at least a partial firing of the loading unit.

* * * * *